US008473313B2

(12) United States Patent
Abreu

(10) Patent No.: US 8,473,313 B2
(45) Date of Patent: Jun. 25, 2013

(54) SYSTEM AND METHOD FOR COMMUNICATING PRODUCT RECALL INFORMATION, PRODUCT WARNINGS OR OTHER PRODUCT-RELATED INFORMATION TO USERS OF PRODUCTS

(75) Inventor: Marcio Marc Abreu, North Haven, CT (US)

(73) Assignee: GeeLux Holdings, Ltd. (VG)

( * ) Notice: Subject to any disclaimer, the term of this patent is extended or adjusted under 35 U.S.C. 154(b) by 518 days.

(21) Appl. No.: 12/591,779

(22) Filed: Dec. 1, 2009

(65) Prior Publication Data

US 2010/0145730 A1 Jun. 10, 2010

Related U.S. Application Data

(63) Continuation of application No. 09/778,762, filed on Feb. 8, 2001, now abandoned.

(60) Provisional application No. 60/182,000, filed on Feb. 11, 2000.

(51) Int. Cl.
*G06Q 50/00* (2012.01)

(52) U.S. Cl.
USPC .............................................. 705/3; 600/300

(58) Field of Classification Search
USPC .......................................................... 705/2–3
See application file for complete search history.

(56) References Cited

U.S. PATENT DOCUMENTS

| 4,707,592 | A | 11/1987 | Ware ............................ 235/379 |
| 4,803,625 | A | 2/1989 | Fu et al. ........................ 600/483 |
| 4,839,822 | A | 6/1989 | Dormond et al. |
| 5,301,105 | A | 4/1994 | Cummings, Jr. |
| 5,367,555 | A | 11/1994 | Isoyama |
| 5,471,382 | A | 11/1995 | Tallman et al. |
| 5,478,990 | A * | 12/1995 | Montanari et al. ............ 235/375 |
| 5,486,999 | A | 1/1996 | Mebane |
| 5,517,405 | A | 5/1996 | McAndrew et al. |
| 5,544,649 | A | 8/1996 | David et al. ................... 600/301 |
| 5,619,991 | A | 4/1997 | Sloane |
| 5,640,002 | A | 6/1997 | Ruppert et al. .......... 235/462.46 |
| 5,644,778 | A | 7/1997 | Burks et al. |
| 5,672,154 | A | 9/1997 | Sillen et al. |
| 5,765,144 | A | 6/1998 | Larche et al. |
| 5,810,747 | A | 9/1998 | Brudny et al. |
| 5,819,029 | A | 10/1998 | Edwards et al. |
| 5,833,599 | A | 11/1998 | Schrier et al. ................. 600/300 |
| 5,839,438 | A | 11/1998 | Graettinger et al. |
| 5,845,255 | A | 12/1998 | Mayaud ............................. 705/3 |
| 5,853,377 | A | 12/1998 | Madsen et al. ................ 600/587 |
| 5,867,821 | A | 2/1999 | Ballantyne et al. |
| 5,978,774 | A | 11/1999 | Rogers et al. |
| 5,999,908 | A | 12/1999 | Abelow |
| 6,014,634 | A | 1/2000 | Scroggie et al. ................ 705/14 |
| 6,018,713 | A | 1/2000 | Coli et al. ......................... 705/2 |
| 6,021,392 | A * | 2/2000 | Lester et al. ...................... 705/2 |
| 6,219,674 | B1 * | 4/2001 | Classen .............................. 1/1 |

(Continued)

*Primary Examiner* — Lena Najarian
(74) *Attorney, Agent, or Firm* — Jacobson Holman PLLC

(57) ABSTRACT

An automated system and method for communicating product information to consumers through a central computer using a distributed computer network. The system acquires and stores data including product identification data and consumer biological variables and, using a processor, determines if the data received interacts with products being stored in memory. Interactions that are determined include product-to-product interactions and biological variable-to-product interactions. The system is also configured to transmit information to a user about an alternative product to a harmful or recalled product.

6 Claims, 56 Drawing Sheets

U.S. PATENT DOCUMENTS

| | | | |
|---|---|---|---|
| 6,233,564 B1 | 5/2001 | Schulze, Jr. | 705/14 |
| 6,406,426 B1 * | 6/2002 | Reuss et al. | 600/300 |
| 6,680,999 B1 * | 1/2004 | Garcia | 379/88.22 |
| 6,886,748 B1 | 5/2005 | Moore | 235/435 |
| 2001/0001144 A1 | 5/2001 | Kapp | 705/3 |
| 2001/0027401 A1 | 10/2001 | Klein | 705/1 |
| 2001/0042022 A1 | 11/2001 | Kirkpatrick et al. | 705/26 |
| 2001/0053980 A1 | 12/2001 | Suliman et al. | 705/1 |

* cited by examiner

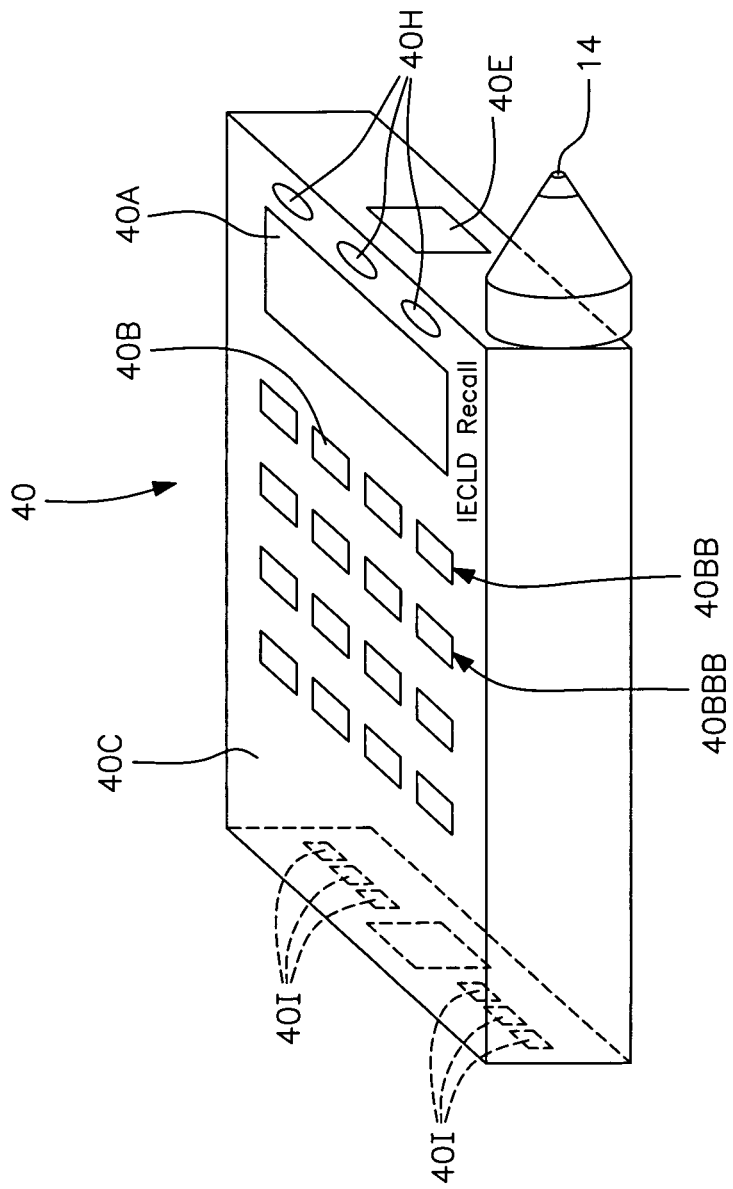

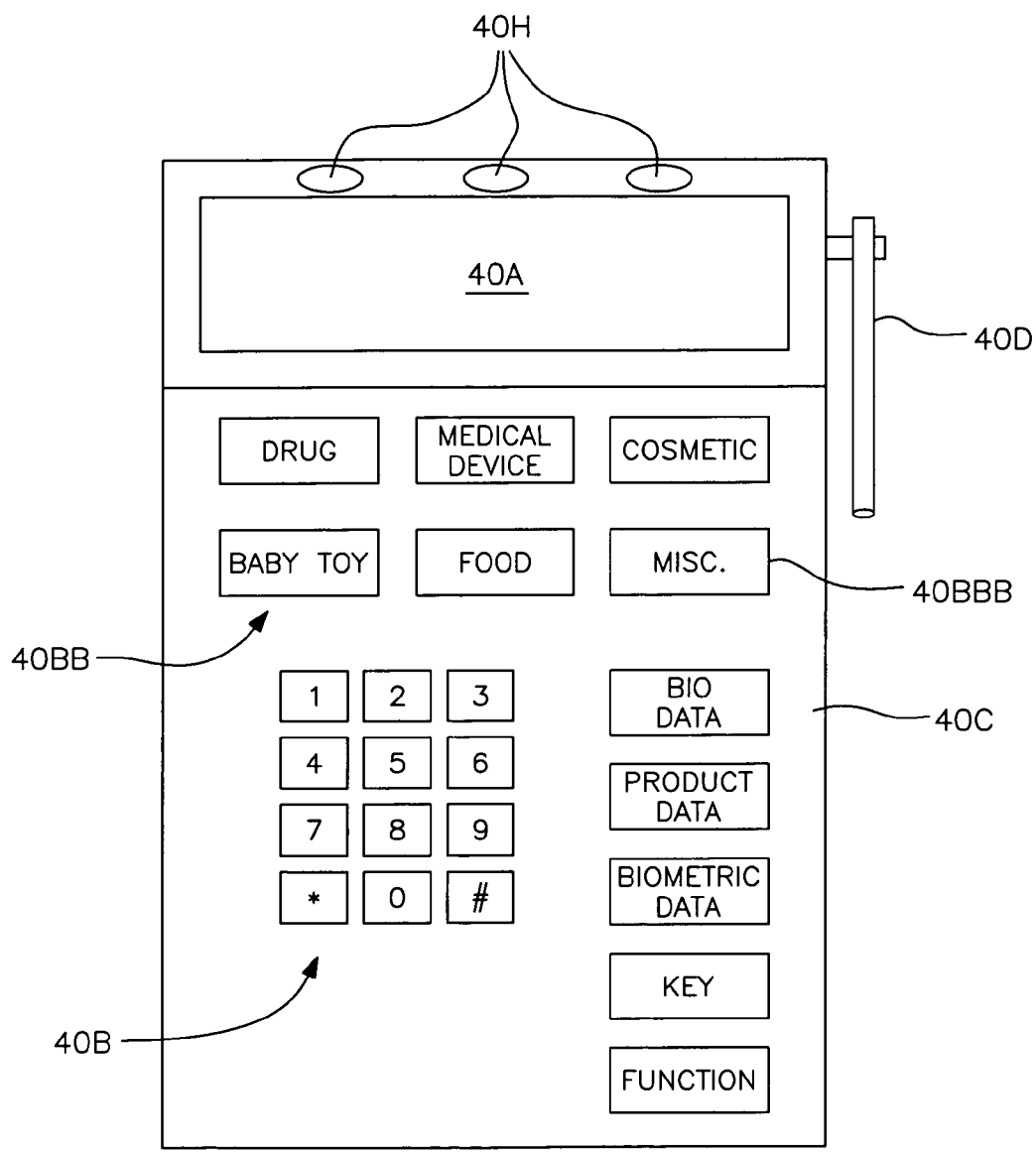

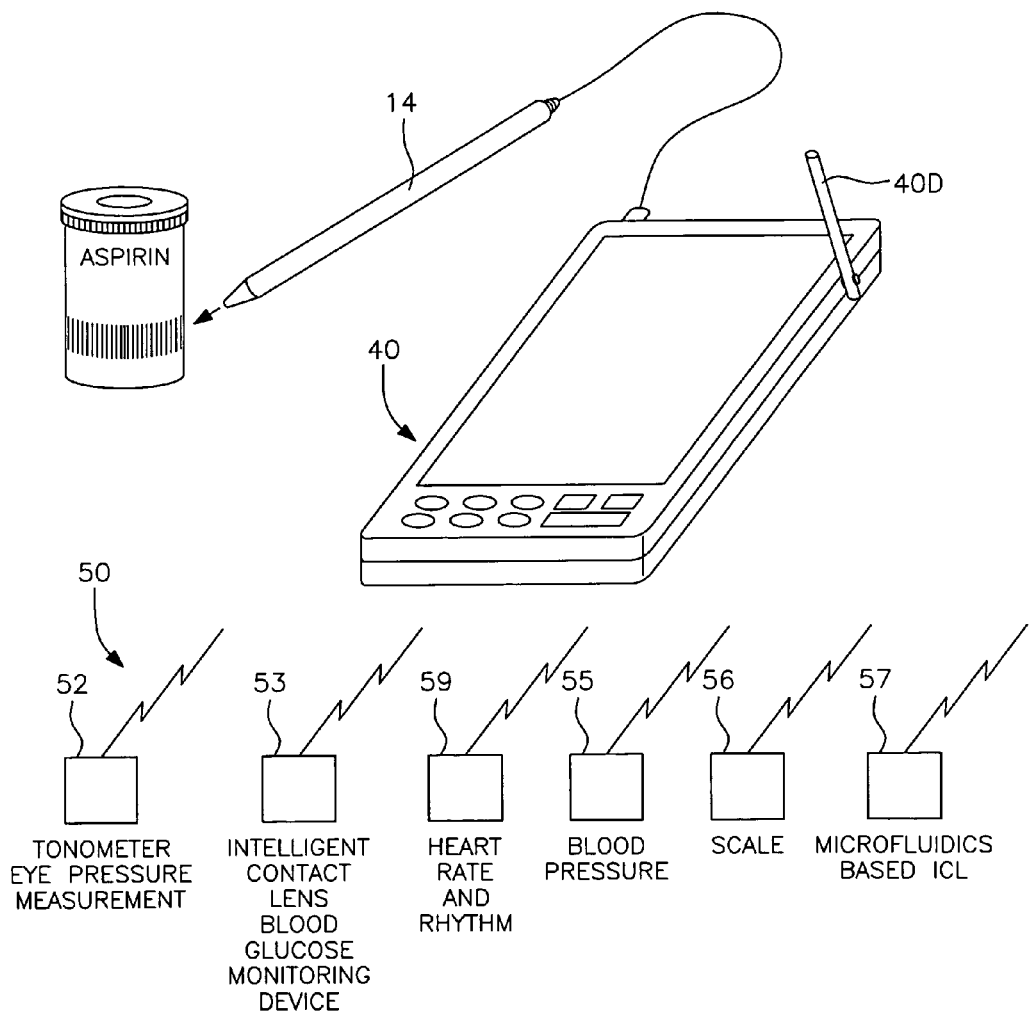

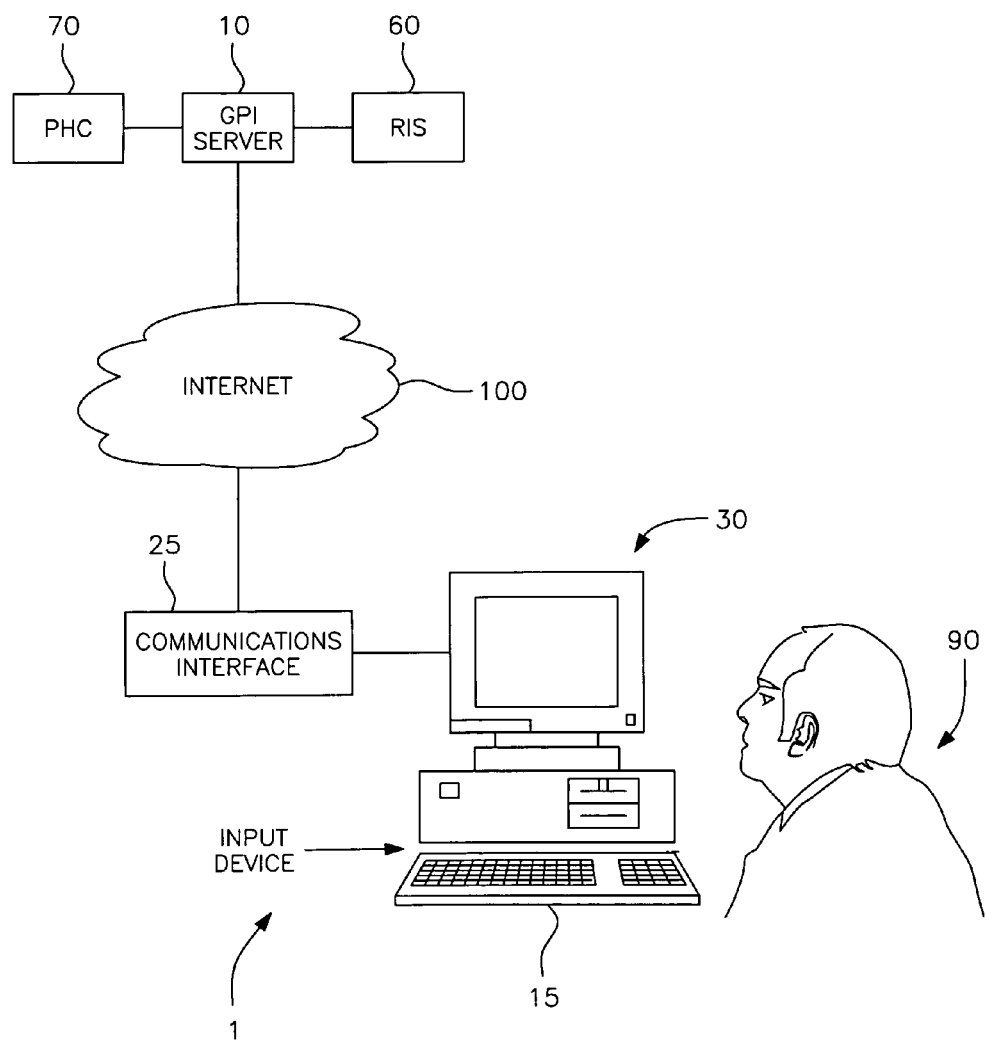

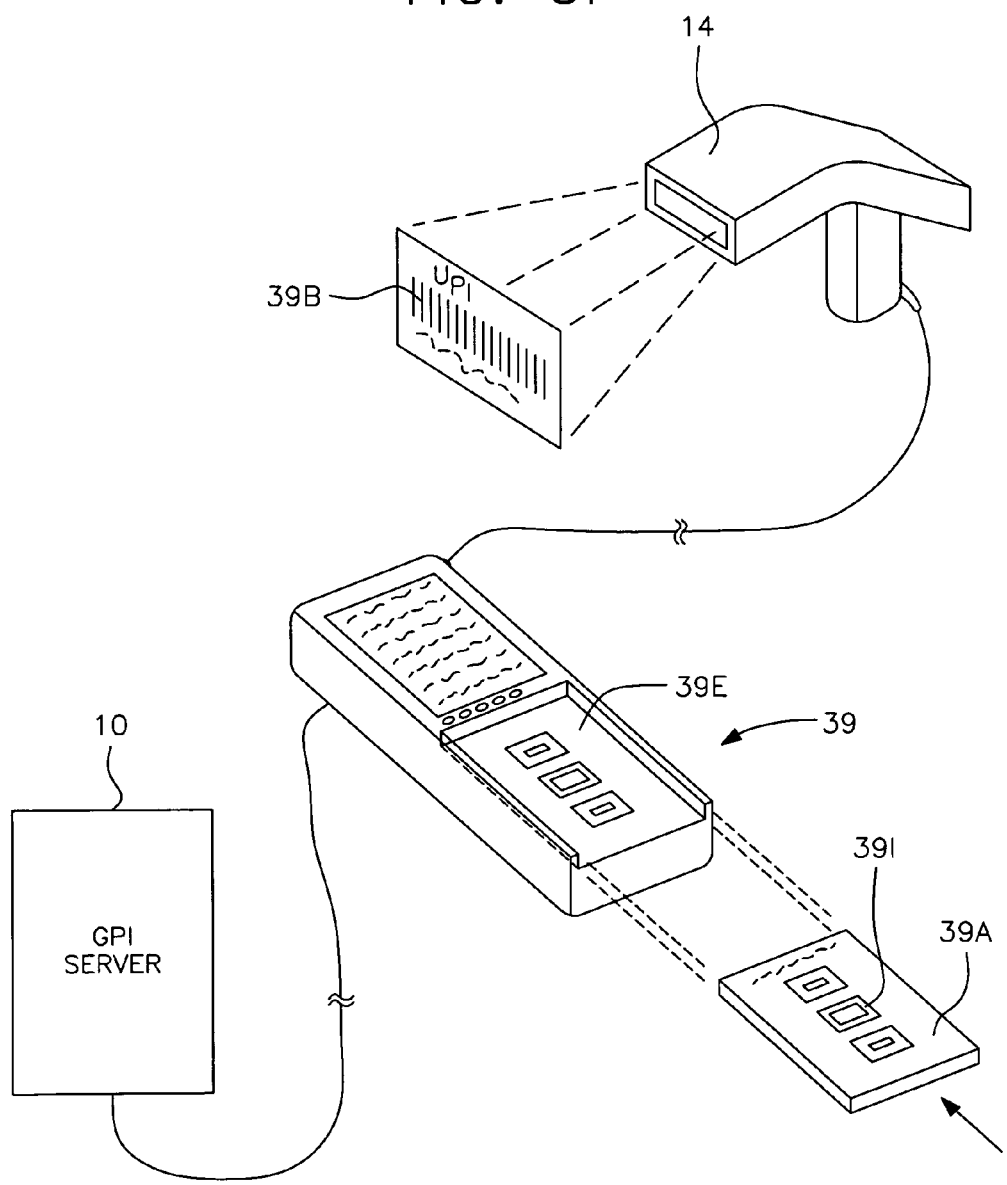

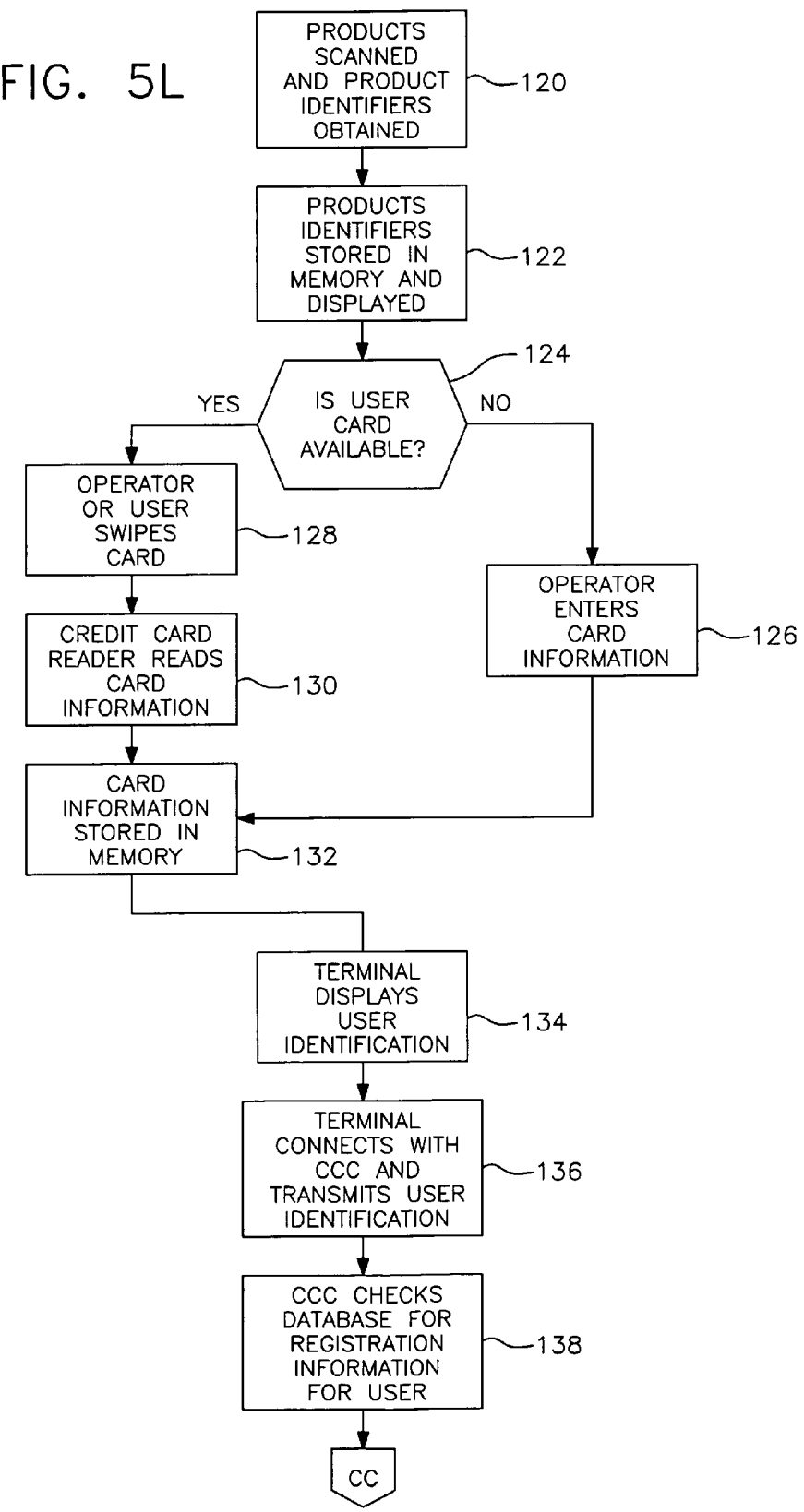

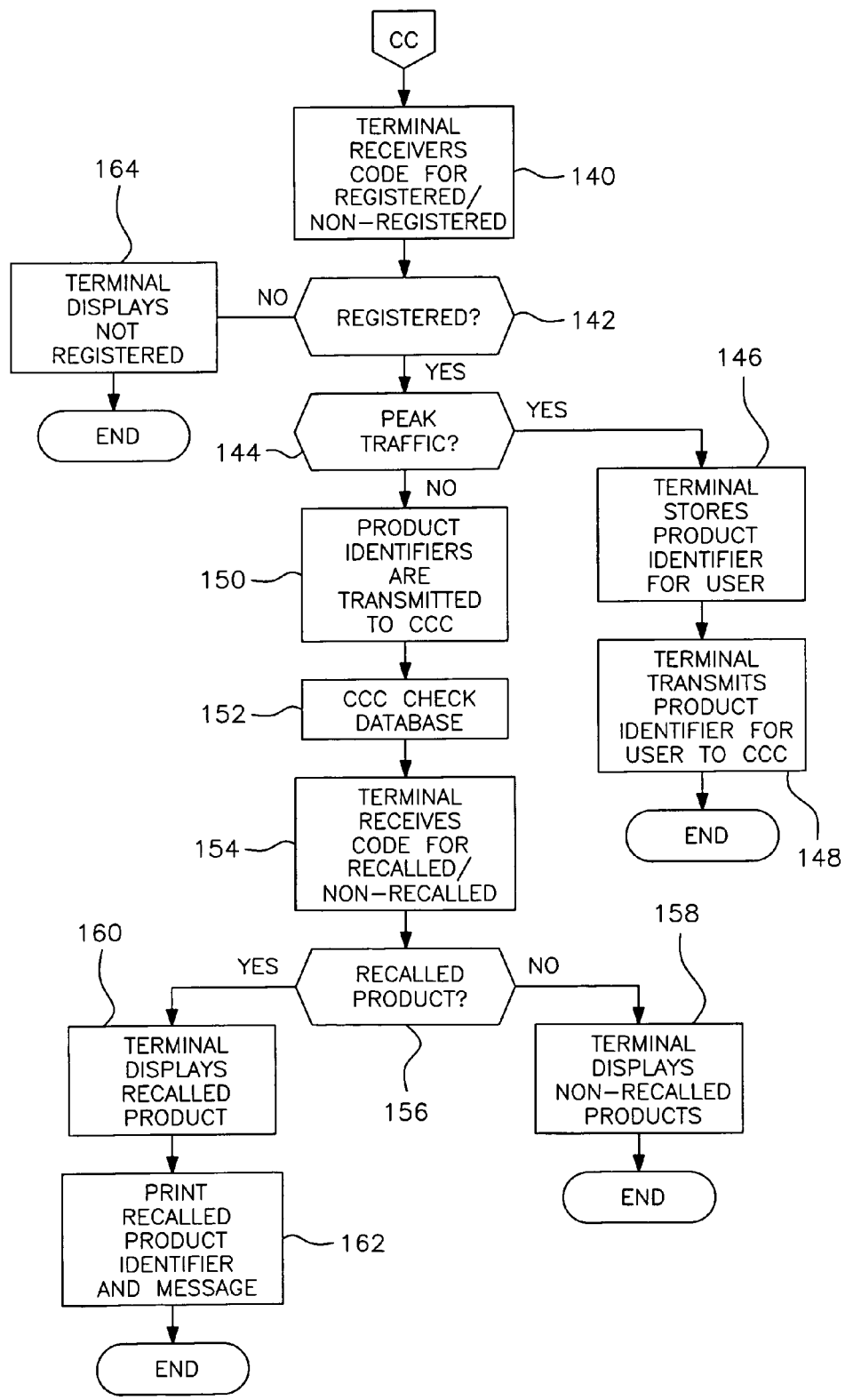

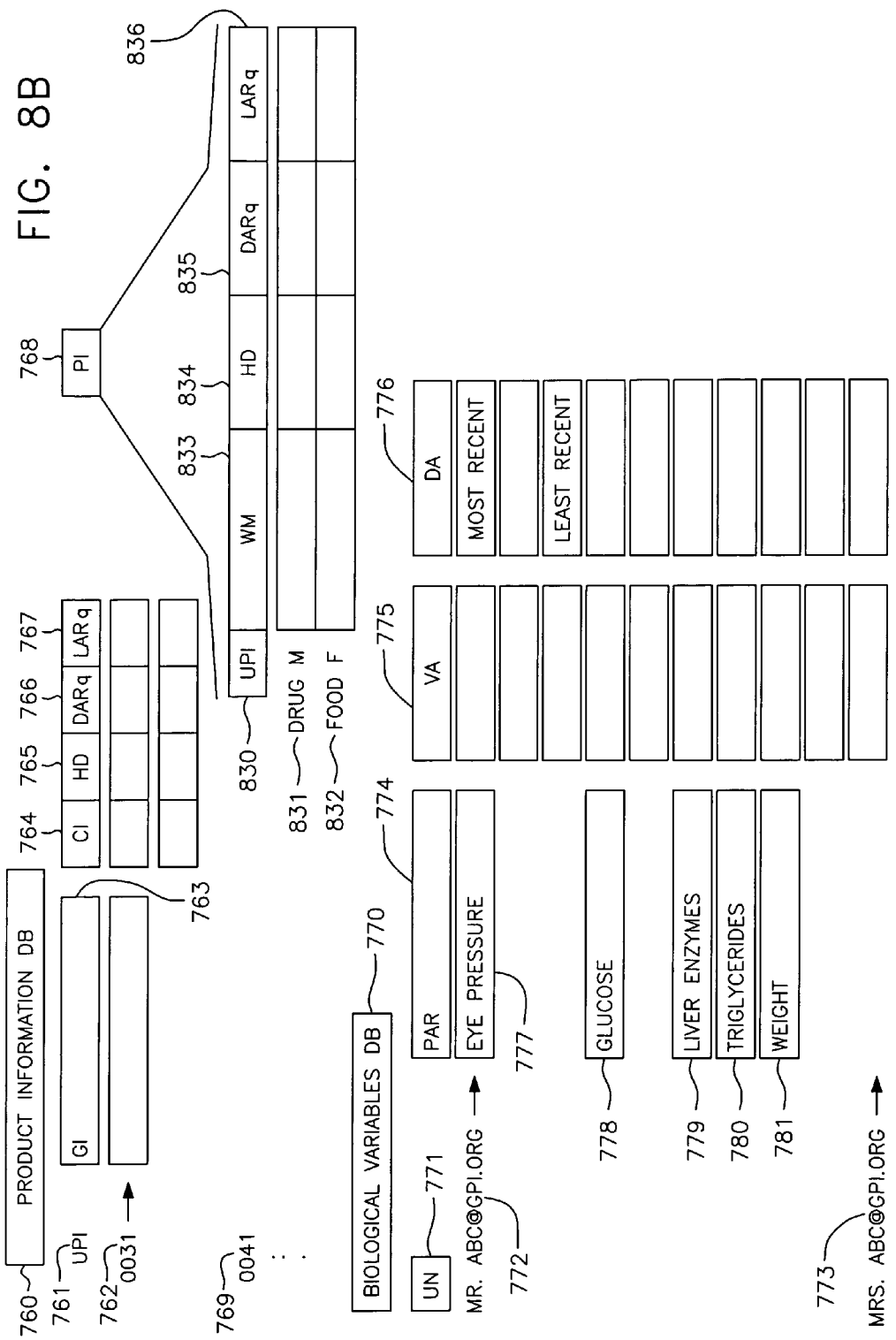

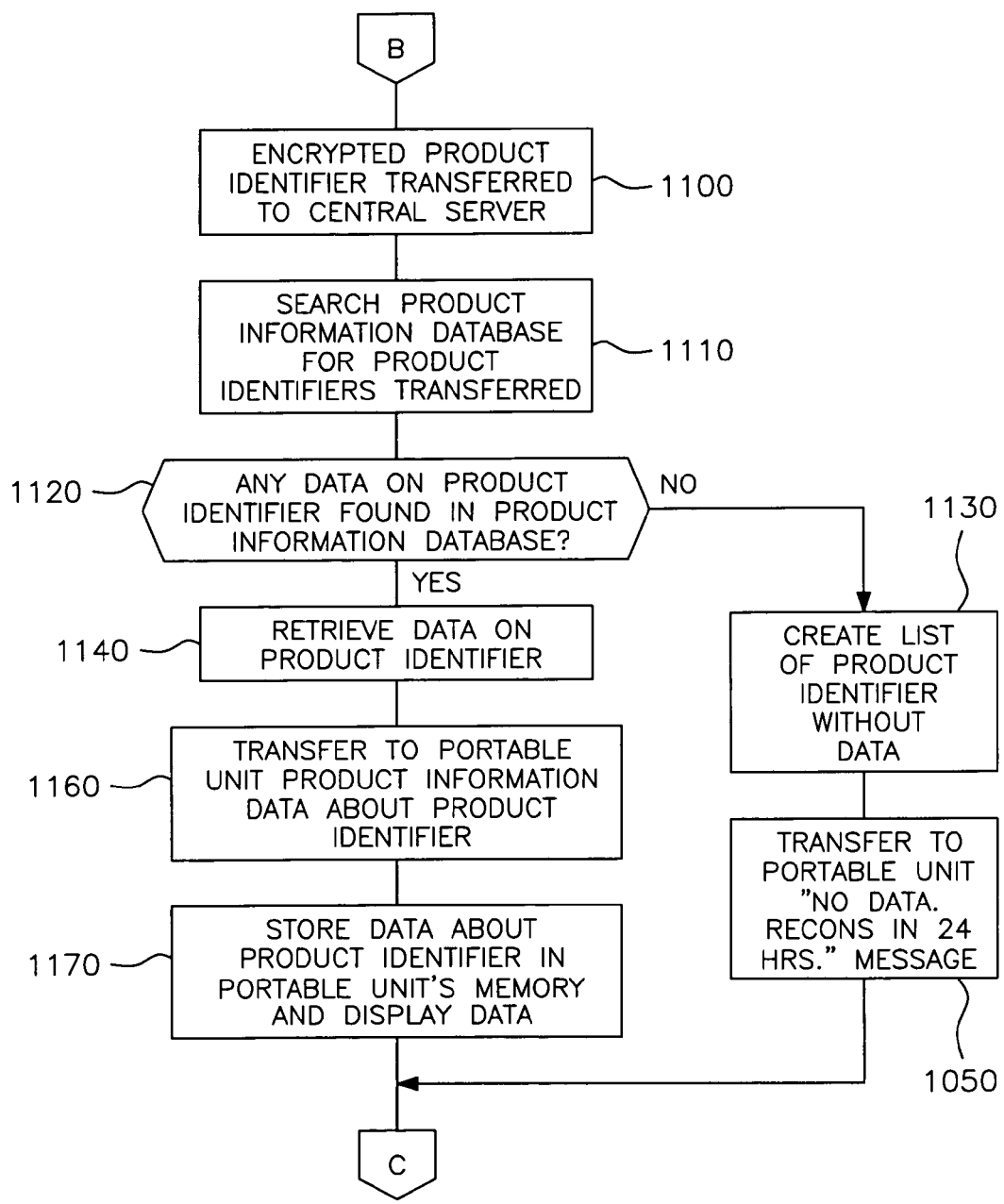

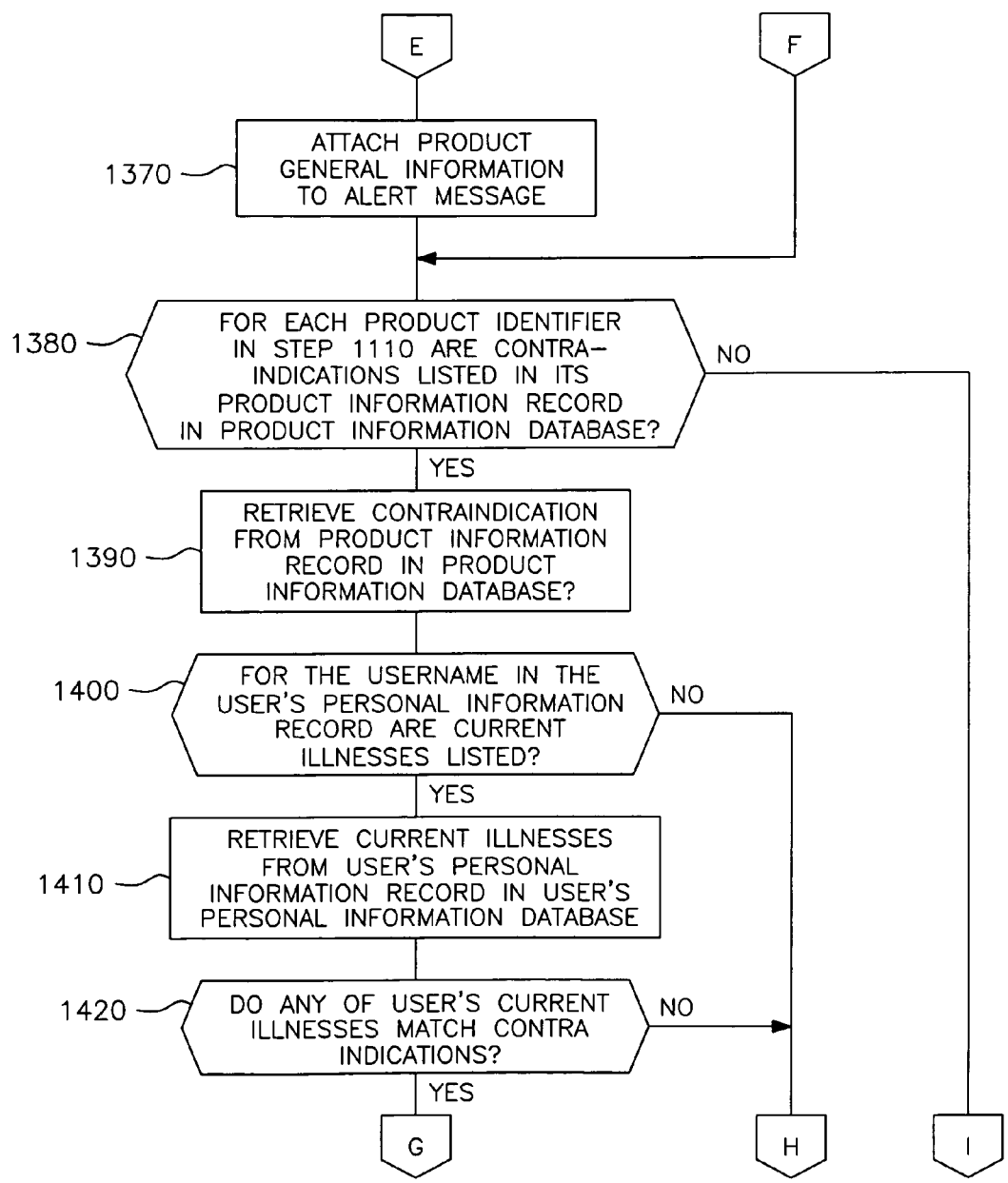

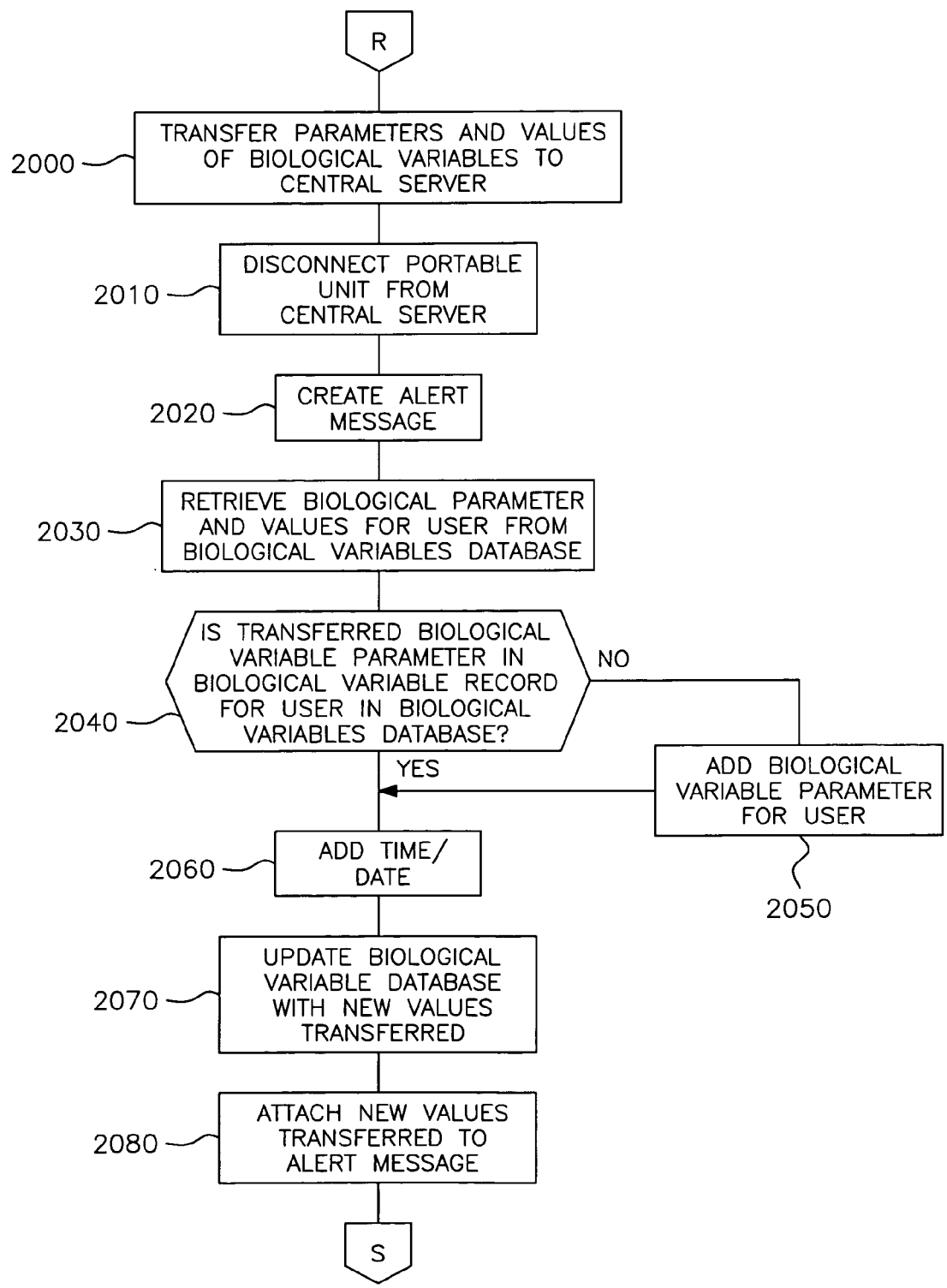

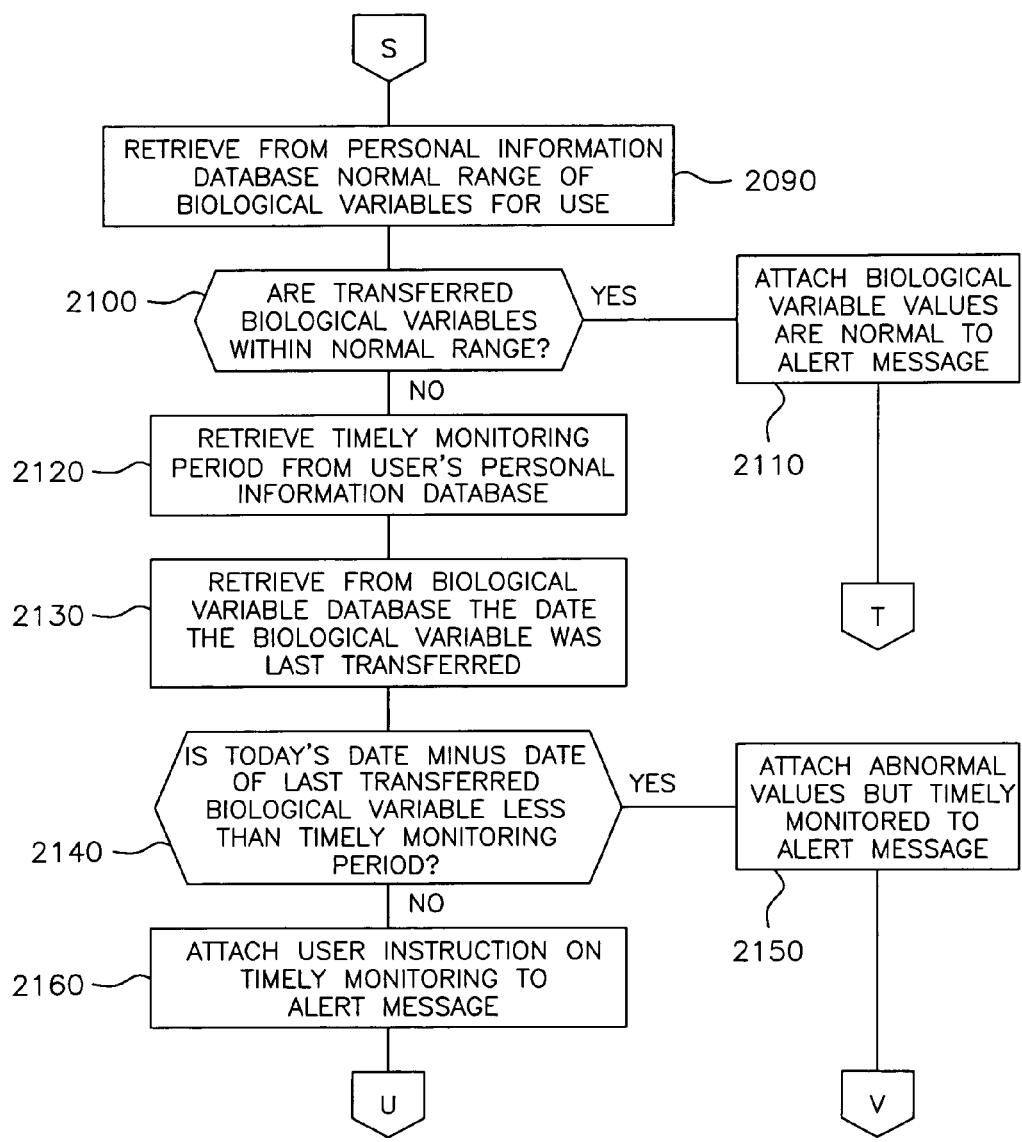

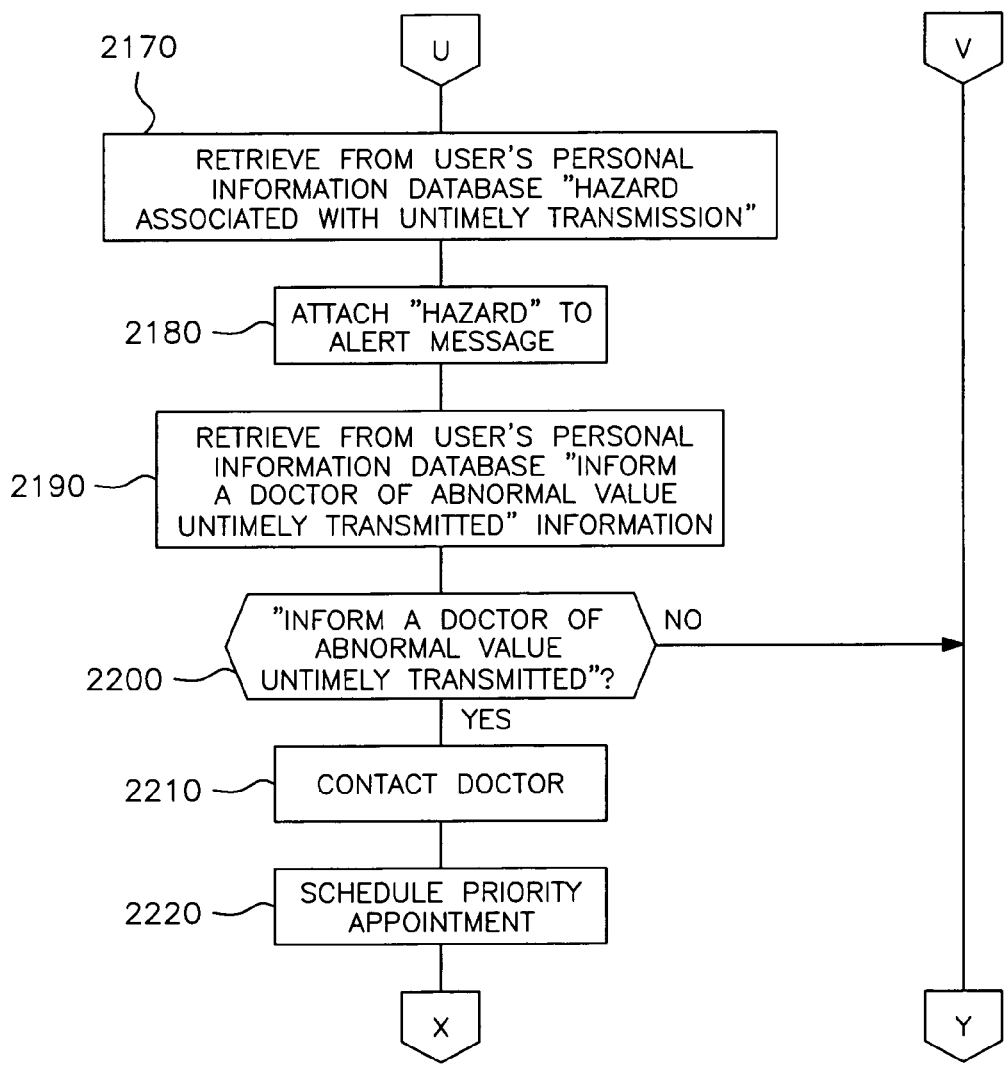

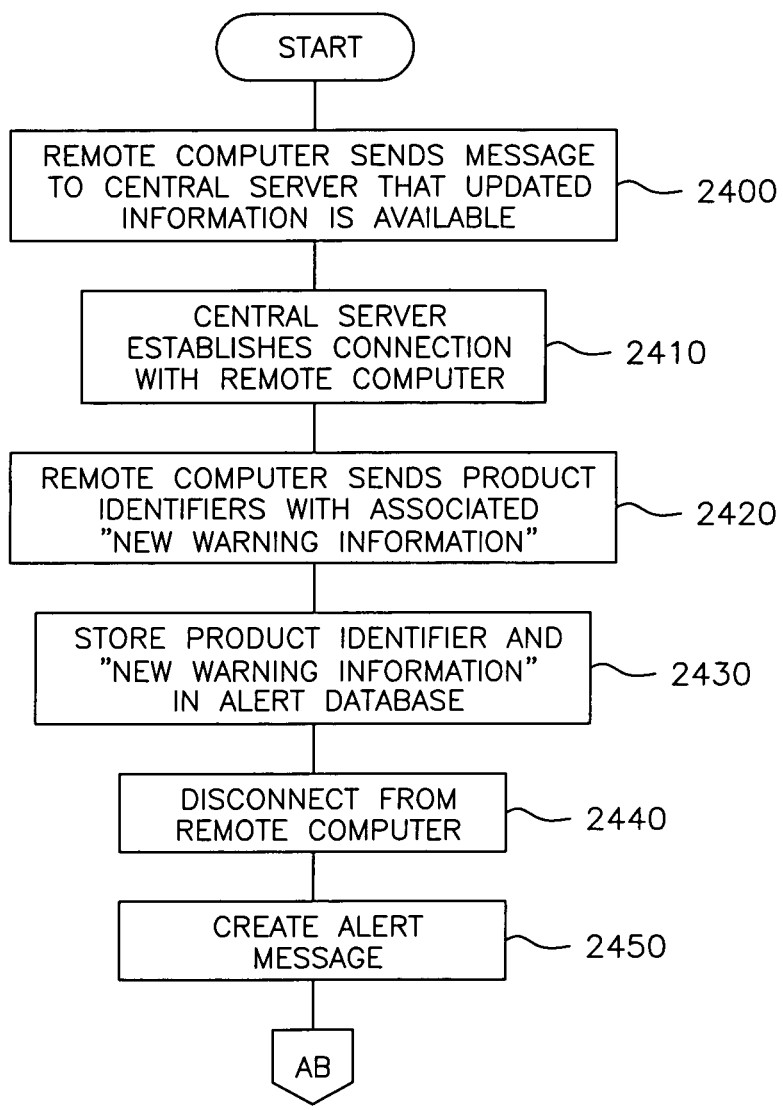

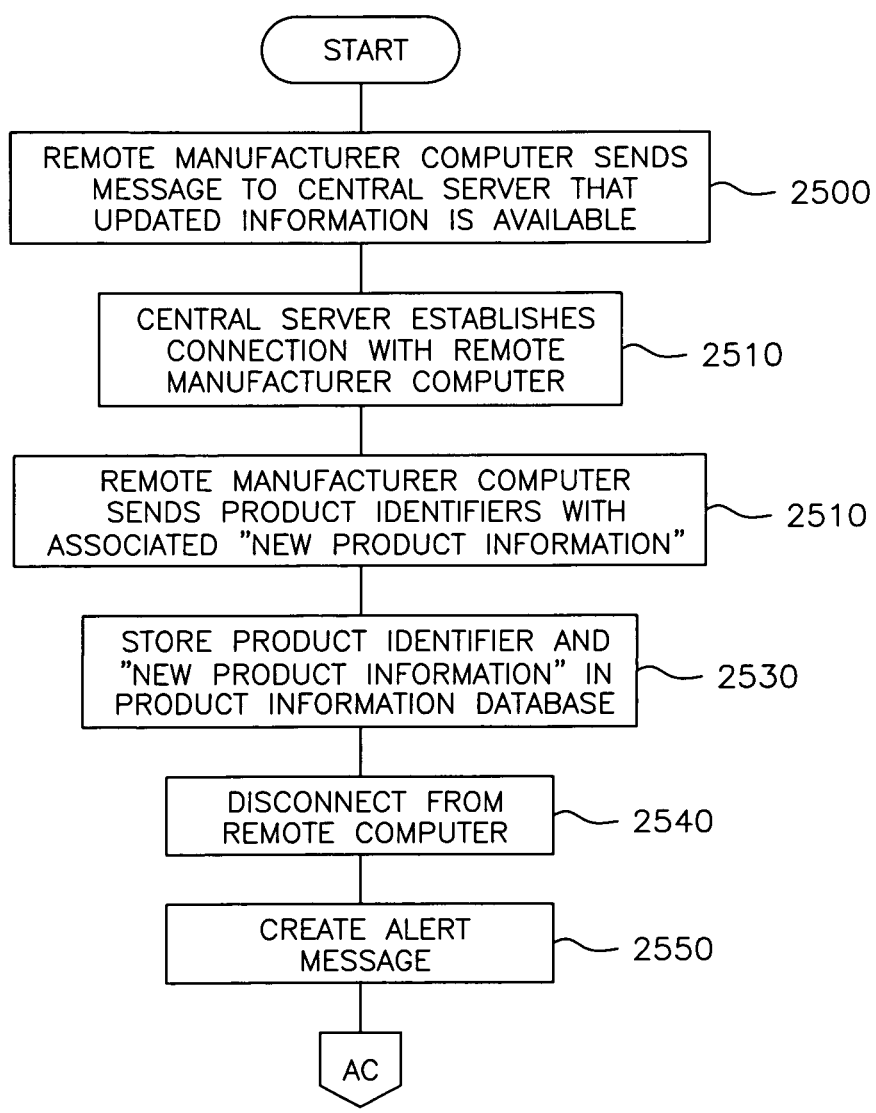

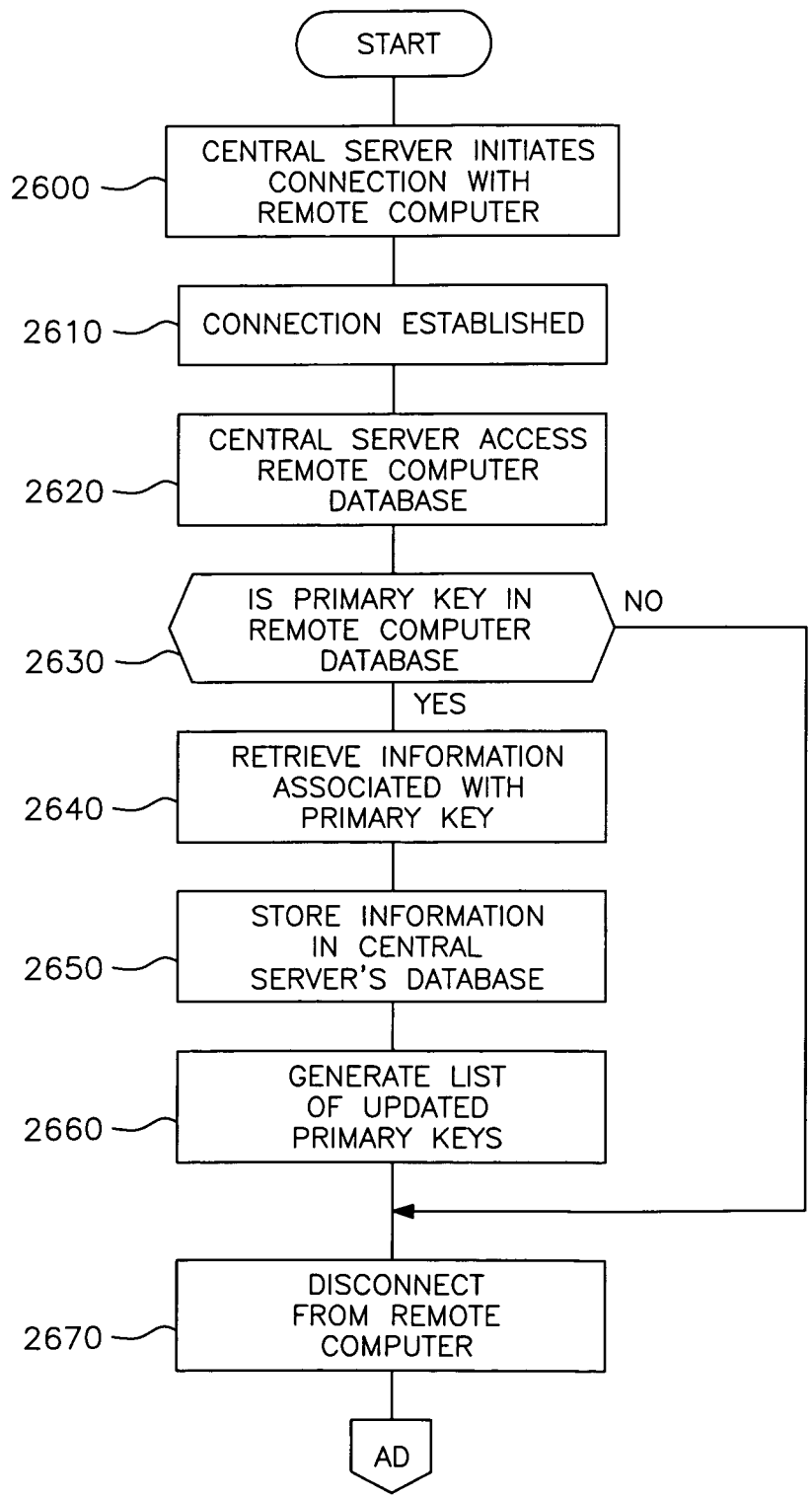

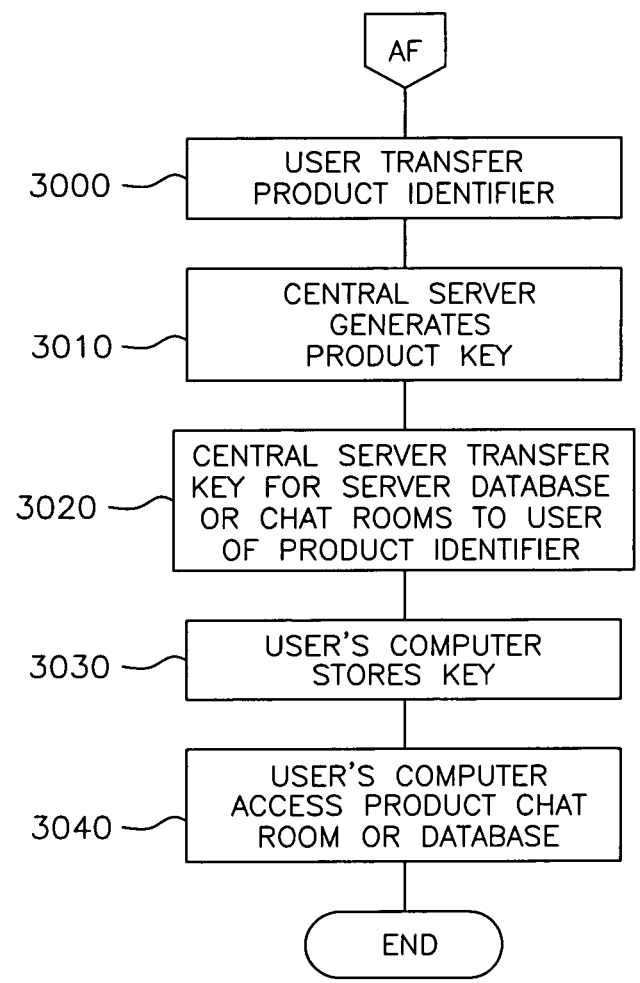

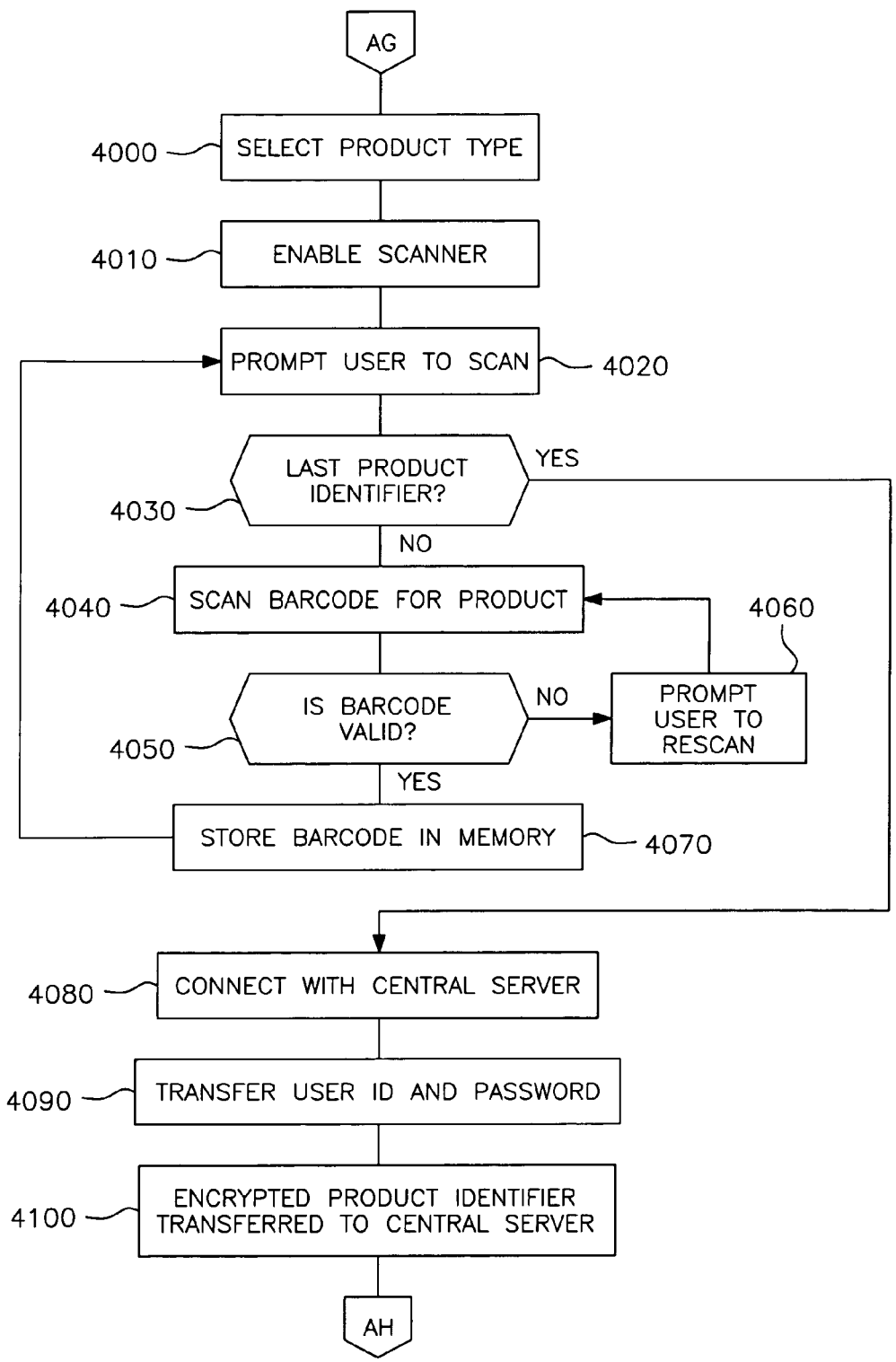

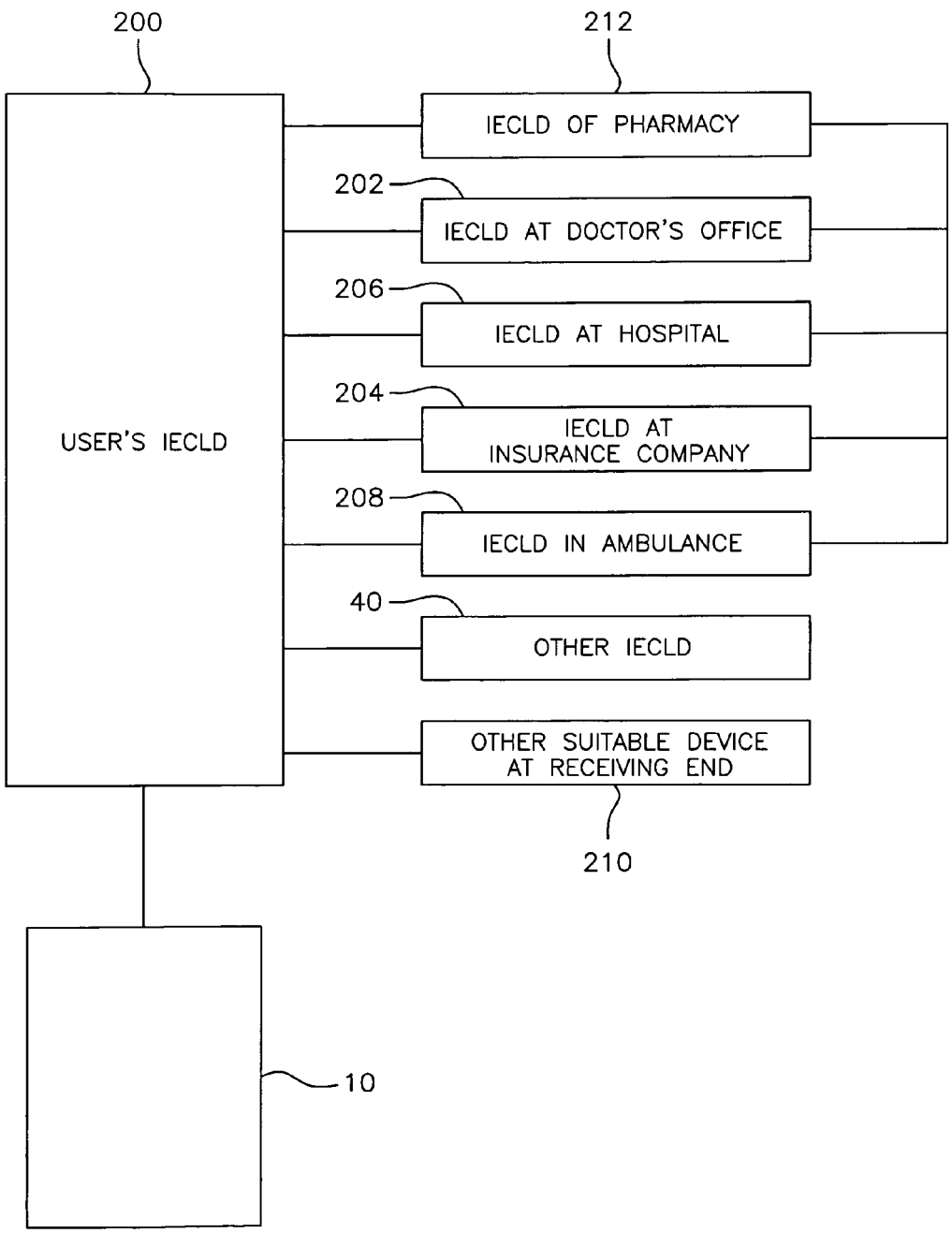

SYSTEM AND METHOD FOR COMMUNICATING PRODUCT RECALL INFORMATION, PRODUCT WARNINGS OR OTHER PRODUCT-RELATED INFORMATION TO USERS OF PRODUCTS

RELATED APPLICATIONS

This application is a continuation of U.S. application Ser. No. 09/778,762 filed Feb. 8, 2001, now abandoned, which claims priority from, and the benefit of, U.S. provisional application Ser. No. 60/182,000 filed Feb. 11, 2000.

FIELD OF THE INVENTION

The present invention relates to a system and method for communicating product recall information, product warnings, or other product-related information to users of such products, and more specifically, relates to a system and method that facilitate implementation of an electronic and network-based recall and notification system that is product-driven and/or biological variable-driven, to assist the users of the system in timely identifying a health hazard or any other hazardous situation or difficulties due to unintended harmful effects and adverse consequences of a variety of products and/or biological variables, and to prevent the occurrence of such harmful effects.

BACKGROUND

The world, especially the United States, is now facing a challenging rise in health care costs. Health care expenditures are rising rapidly. Contributing to this rise, there has been with a rapid increase in the number and spread of preventable illnesses and injury that are attributable to the unintended harmful effects of a variety of products and/or changes in the health status of an individual interacting with such products. According to projections by the Health Care Financing Administration of the United States Department of Health and Human Services, health care spending as a share of US gross domestic product (GDP) is estimated to increase from 13 percent to close to 20% of the United States GDP after the year 2000. This clearly demonstrates how unwise health care spending can affect the overall economy of a nation. The World Health Organization reported in 1995 that the percentage of total spending on health by various governments clearly indicated that health care costs are a serious global problem and an important factor concerning the overall utilization of public money. Public spending on health by the United States government was about 47%, by the United Kingdom was 84%, by France was 81%, by Japan was 78%, by Canada was 71%, by Italy was 70%, by Mexico was 56%.

The United States Department of Agriculture has estimated that the medical costs of illnesses caused by the unintended harmful effect of food alone amounted to over $34 billion dollars in 1998 (more than the combined global revenues in 1998 of Coca-Cola and Microsoft). It is easy to appreciate the threat to a nation's economy that such a situation presents. This, however, is only a fraction of the total medical cost created by the unintended harmful effect of products. The unintended harmful effect of prescription drugs, for example, resulted in an astonishing annual cost of $136 billion dollars in the United States. This is greater than all of the costs incurred as a result of heart disease (the number one cause of death in the United States). The above medical costs attributable to the unintended harmful effects of prescription drugs is more than the combined global revenues of all major airlines in the United States, England, Germany, Japan, France and Spain, which totaled $120 billion U.S. dollars in 1998. The situation is much more serious and inconceivably far more costly when the harmful effects of other consumer products are considered. This ultimately imposes a tremendous burden on the income tax payer and average worker, who at the end is the one paying for the vast majority of the costs associated with health care services. The fastest and most effective way to protect the public from an unsafe product and thus decrease such outrageous and unwise medical expenditures would be to timely and reliably identify, locate, and instruct the users of such unsafe products. Due to the seriousness of the harm and the rapidly increasing number of occurrences of harm and death caused by a variety of products, the government, private enterprises and medical organizations have an urgent need to find means and technology to prevent the spread and occurrences of illnesses and injuries that result from a failure to timely identify, locate, and treat users of harmful products. The ability to satisfy this need is critical to the containment of health care spending, not only in the United States, but also globally.

The development and use of a variety of medications (drugs) is essential to promoting health and treating a great number of disorders, while substantially increasing life expectancy. There are many benefits to the development of medications. Certain antibiotics, for example, have saved millions of lives. Antihypertensive drugs likewise have helped reduce the number of occurrences of strokes and heart disease, by controlling high blood pressure. The use of cholesterol lowering agents also have helped decrease the mortality rate associated with heart disease, the use of anti-depressants have helped millions of individuals better enjoy life, and the use of anti-glaucoma medications have helped millions of patients preserve their sight. The exhaustive process and laborious research involved with drug development have created many other breakthroughs and formidable drug discoveries which, in turn, have led to the control of previously untreatable diseases and a decrease in morbidity, while enhancing the quality of life and increasing life expectancy for millions of people across the world. However, these great benefits are associated with serious and costly problems due to the astonishing fact that not only thousands, but actually hundreds of thousands of patients die every year in the United States alone, as a result of drug reaction or unexpected and unintended adverse effects and reactions caused by prescription drugs.

Adverse drug reactions resulting from correctly administered FDA-approved drugs alone are responsible for the shocking figure of over 106,000 deaths per year in the United States alone. Adverse drug reactions are the fourth leading cause of death in the United States, immediately after heart disease, cancer, and stroke. The number of deaths caused by the harmful unintended effects of prescription drugs is amazingly more than the annual totals for AIDS, suicide, and homicide combined, and amount to more than twice the number of deaths due to accidents (which is about 40,000 per year). A person is more likely to die from an adverse effect of prescription medication than from accidents, diabetes, or lung disease. The staggering number of close to 300 deaths per day resulting from prescription drug adverse reactions remains unchanged due to the difficulties in timely identifying, locating, preventing use of the medication by, and treating the individuals at risk. In addition to the fatal events, there are typically over 2.2 million annual occurrences of non-fatal, but serious, reactions, and millions of complications and disabilities related to unexpected effects of drugs, chemical compounds and a variety of products which are responsible for some of the staggering health care spending that the world faces today. Unfortunately, this alarming picture will continue to worsen in the future, with devastating consequences to the economy, tax-payers and society as a whole if appropriate measures for prevention and the timely identification and location of the harmful products and affected individuals is not instituted to avoid spreading of potentially preventable injuries and disease.

The above catastrophic picture is even more grim and astonishing since the above figures exclude drugs which were improperly prescribed or improperly administered, as well as drug abuse and drug overdose and adverse effects caused by non-prescription drugs (over-the-counter medications), devices and other chemical compounds which are injected, ingested, or placed in or on the human body. If the adverse effects and fatal reactions related to the use of over-the-counter drugs (non-prescription drugs) and other products such as cosmetics were included the numbers would prove to be even more staggering. The risks, injury, and death caused by unintended adverse drug reactions and defective products could be substantially reduced if appropriate technology were implemented to provide the requisite notification, guidance, treatment, or the like.

The misuse of prescription and non-prescription drugs due to the inability to understand or identify a potential hazardous effect is also a critical cause of morbidity and mortality related to the utilization of a variety of products, devices, and chemical compounds. The ability to understand information about drugs, chemical compounds or devices is central to the prevention of some of the aforementioned devastating consequences. The U.S. Department of Education estimated that 47% of all adult Americans had poor reading and comprehension skills. Large amounts of medical material therefore can exceed the reading abilities of many American adults. Although there is information printed on the packages and product inserts that accompany prescription and over-the-counter drugs, as well as many other products, the majority of the population has difficulty understanding, interpreting, or using the information provided. As a result, many individuals suffer adverse effects due to their inability to understand the content of the information provided by the manufacturer and its relationship to his/her individual health status. It is important to remember that the health status of an individual is a dynamic process with continuous change over time. Such changes in the health status are quite capable of potentially interacting with chemical compounds and devices used by the patient and causing serious and even fatal effects and reactions. New technology is surely needed that will assist the user in safely using a drug despite his/her lack of knowledge regarding medical terminology and the interaction of drugs and products with the human body's continuously changing biological variables.

The prior art has provided several important home-testing technologies. Examples include several devices developed by the Applicant hereof. Such devices can be used by patients to self-administer measurements of eye pressure and perform a complete non-invasive blood analysis that includes evaluation of a variety of biological variables. Heretofore, there has been no convenient and reliable way of associating such home-testing devices with a notification, guidance, and/or treatment system, to provide a complete system of preventing negative interaction between chemical compounds used by the patient and changing biological variables of the patient. There is consequently a need for such a system. A brief example demonstrates the situation. Patients using some medications for the common cold or flu or products containing steroids may be at risk for damaging their eyes or even blindness if one biological variable, in this case, eye pressure is significantly increased. The increase in eye pressure can be silent, without any symptoms that would otherwise indicate that the individual may have glaucoma. The packet insert of the common cold pill and some skin lotions with steroids may have a warning against use of such products by those with glaucoma. Unfortunately, however, the person taking the pills or using the skin lotion typically does not know what glaucoma means, even after reading the packet insert, and will continue to use the product not knowing that there is a risk of eye damage. There is consequently a need for a system that will alert patients about such risks, regardless of the patient's knowledge of the meaning of the medical terminology in the packet insert and/or potential interaction with their health status and current biological variables.

The rapid rise in health care costs also relates to the disturbing fact that millions of patients suffer from severe complications, permanent disability, and death as a result of untimely identification of a health problem or untimely arrival at the medical provider or hospital. The medical costs associated with such untimely treatment cannot be overstated. There is consequently a need for a system that, in addition to preventing the harmful event from occurring, also can alert the user to seek treatment and arrange for treatment when such treatment becomes necessary as a result of injury or illness caused by a harmful product and/or changing biological variables.

Many adverse effects and reactions resulting from the use of chemical compounds and/or devices occur after the chemical compounds or devices are already in the marketplace and being used by potentially millions of consumers. The pre-marketing trials conducted during the evaluation process of drugs and devices frequently are not sufficient to reliably detect adverse effects and reactions and lack the requisite length of follow-up which is needed to evaluate the delayed consequences that manifest themselves only after chronic use or wide spread administration of drugs and devices. In addition to the limits associated with pre-marketing evaluation by the United States Food and Drug Administration (FDA) of drugs and devices, these trials do not include evaluation of the interaction of drugs with a variety of biological variables, nor do they involve evaluation of the result of use by special population groups that can be at a higher risk for adverse effects or reactions, when compared to the general population. Furthermore, the inability to identify the changes that occur in the healthy status of an individual such as changes in blood pressure, eye pressure, blood glucose, blood cholesterol, weight, and the like, make it virtually impossible to identify and prevent adverse reactions or effects that occur with the utilization of drugs and/or devices interacting with changing biological variables.

In order to identify and thus prevent the catastrophic complications due to the adverse effects of drugs, chemical compounds and devices that were not identified during pre-marketing evaluation, a post-marketing surveillance system has been instituted by the FDA. The sample size of the typical pre-marketing trial is small, with a short follow-up, when compared to the use of the drug by the general population in which thousands and even millions of patients will use the drug or devices for a long period of time with the consequent development of drug reactions. The post-marketing surveillance represents an attempt to address this limitation and relies on spontaneous reporting by health care providers and companies of adverse effects or reactions which were associated with the use of the chemical compounds, devices, cosmetics, or the like. The post-marketing surveillance system, however, includes no system or method adapted to directly alert the patients at risk. The post-marketing surveillance system instead relies basically on the physician informing patients on an individual basis. This is accomplished at the doctor's discretion and using his/her available resources. The primary objective of the post-marketing surveillance is to alert the health care provider and companies, but no system is in effect to directly address the individual user and all users of the harmful product.

The adverse events or reactions that result from the use of drugs, devices, cosmetics, or the like can occur during different stages of use (e.g., shortly after initiation of use, after long term use, and even much later, after the drug, chemical compound or device has been discontinued and/or recalled). Moreover, for each one report received by the FDA, it is estimated that there may be over 100 actual reactions. This demonstrates that the post-marketing surveillance reporting system used by health care providers substantially underestimates the actual number of adverse reactions and effects. Unfortunately, the most common way for a patient to discover that a product is harmful is after they have suffered injury or even death caused by the harmful product.

Besides the unintended detrimental effects caused by drugs and/or devices, the use of medications or devices may be associated with unintended beneficial effects. The post-marketing surveillance system also attempts to identify those beneficial effects and was key in identifying that hormonal therapy in post-menopausal women reduces death from cardiovascular disease, and that oral contraceptive users have a lower risk of ovarian cancer. There is consequently a need for a system and method that individually informs all of the users of a beneficial effect related to the particular drugs they are using.

The post-marketing surveillance system and prior art currently used suffer from many limitations and drawbacks, and is unable to efficiently identify, locate, prevent, and treat the unintended harmful effects of a variety of products after the product has been identified as harmful, as the above numbers clearly show and some of the following examples will further demonstrate.

A drug that was widely advertised on television by the name Loratadine and which is used to treat allergies, was found during post-marketing surveillance to cause esophagus rupture with even potentially fatal complications. The unexpected reason for this complication was identified as the size of the tablet for a particular formulation. The tablet was too large and caused blockages and subsequent potential rupture of the gastrointestinal tract. As a result of rupture, caustic gastrointestinal contents poured into the mediastinum and the surface of the heart, potentially leading to the demise of the patient. Although there was a great effort by the government and manufacturer to notify doctors and patients about this catastrophic event, many patients had no way of learning that their particular formulation of Loratadine could cause these completely unexpected complications, unless they were informed by their doctors or, in a few occasions, through the media. Due to the widespread use of this drug and the obvious difficulties in locating and alerting patients, astonishingly even after the announcement to doctors and the public by the FDA and the manufacturer about these devastating complications, patients unfortunately still were using the drug.

Another similar situation occurred with the antihistaminic drug called Terfenadine, which was subsequently found to cause potentially fatal arrhythmia when taken with certain antibiotics. In many cases, even after a drug has been discontinued and/or recalled, patients still use the recalled drug and are injured because it is virtually impossible for doctors, companies, and even the government to locate and inform all users of a particular drug about the complications. Drugs used by patients are usually manually written onto patients' charts. It would be necessary to manually review the thousands of charts for every medical practitioner and subsequently identify written information on the chart regarding different medications used by each patient. Since in most cases there is no indication about the date that a certain patient was started on a particular medication, this chart review would have to include the hundreds of pages that each chart may have. Of course this would have to be done any time a new adverse effect was identified for the drug as well as a new harmful drug was identified. Naturally, this is an insurmountable task. The data for each patient to be identified, located, and warned about the potential hazardous situation is impossible to retrieve in any practical manner. Sometimes the product does not need a prescription which makes the direct identification and location of the user impossible using existing recordkeeping techniques. The problem is further demonstrated by a situation involving a shampoo capable of treating dandruff. That shampoo was later found to cause fatal reactions, blindness, diabetes, and other severe complications because of certain ingredients in its composition. Since this product was being sold over-the-counter without the need for a prescription, there is no way to identify who is using this extremely dangerous shampoo, even though it has been recalled and removed from the market. Users therefore continue to perish and suffer because they do not have access to the information on the hazards posed by the shampoo.

Unfortunately, the most common way that a user finds out about the potential harmful effects of product is by suffering the illness, injury or death caused by the harmful product. The above are only a few examples of real events that occurred in connection with such products. There are many other products causing harm and being recalled every year.

The picture is unfortunately more shocking and alarming when we consider the fact that defective products cause a similar amount of injury as described above, and even deaths as the following example will show. On May 12, 1998, a 17-month-old toddler died when his portable crib collapsed and strangled him at a licensed day-care facility in Chicago. The loss of a young child is surely irreparable, but more difficult to accept is the fact that it could have been prevented. Most astonishing is the fact that the portable crib that killed the young child had been recalled in 1993, five years earlier, by the United States Consumer Product Safety Commission (CPSC) and by the manufacturer. Neither the parents nor the day-care provider were aware of the recall. The crib collapsed wedging the toddler's neck inside the folded V of the rails and killing the child in one of the most horrifying ways, the inability to breath. The child was prevented from breathing and could not cry for help during the last minutes of his life. This same type of crib had already strangled and killed many children, but the available notification methods and system were inefficient and incapable of tracking, identifying, locating, and alerting the user about a potentially harmful and even deadly product. Although the recall was publicized several times, primarily through the news media, ads and other conventional, printed means, the message reached a very limited portion of the population and, even today, this deadly product is still present in many homes. It is important to remember that strangulation if not fatal, can lead to brain damage and a lifetime of nursing and institutional care for those unfortunate toddlers. There is consequently an increase in health care costs associated with these defective products, not to mention the emotional toll.

The following illustration will further demonstrate the inefficiency of existing systems and methods in recalling, tracking, and locating already known harmful drugs and other consumer products. Within weeks of the death of the aforementioned child, his parents began an urgent and massive e-mail campaign "Prevent death of next child" warning of the danger of the recalled portable cribs with the message being forwarded all over the U.S. and the world. The parents founded "Kids In Danger", a charitable organization that warned millions of people in the U.S. and abroad about the dangers of recalled juvenile products by granting interviews to print, radio and television media and through E-mail and printed warning campaigns. The message reached various organizations, such as the American Academy of Pediatrics and other major medical and public organizations. Many of the respondents had a recalled crib but were not aware of the danger. Some of the responses to the e-mail posted by "Kids in Danger" demonstrate the magnitude of this alarming problem. The following are examples of such responses:

1). "The dissemination of recall information is horribly lacking. We have called all of the manufacturers of the equipment we use with our children and discovered that the carrier of our stroller has been recalled because it flips children out of the seat; we returned the warranty card over a year ago, when we purchased the stroller, and still were not notified of the recall. It is certainly clear now that parents and child care providers and state agencies need to be proactive in chasing this information down"

2). "I think it's bad that we have to really research in order to find out if a product we bought is considered safe. That safety seems to be an ever-changing line, does it not? I grieve with the families that have suffered; it is senseless."

3). "I read the newspaper every day. I never heard about this danger to my children until now."

This outstanding organization, "Kids in Danger", issued a press release urging a far-reaching advertising campaign and began a nationwide television and print media campaign and also distributed public safety announcements to radio and television stations nationwide, encouraging consumers to call the CPSC to verify whether products in their possession have been recalled for safety problems. The massive nationwide and international e-mail campaign as well as massive media announcement, associated with extensive government actions that occurred after the death of the above-mentioned child were important and helpful, but unfortunately inefficient and limited by the existing systems and techniques for notification. Even after all of those efforts, the same needless tragedy happened again. On Aug. 19, 1998 (only 3 months after the aforementioned death), another innocent baby was killed by the same product in Fair Haven, N.J. The second baby was killed in the same terrifying manner. He was strangled to death when the same model of portable crib collapsed and crushed his throat. Unfortunately, the potentially life-saving recall information about the deadly crib never reached this innocent child's parents. It is clear that the commonly used systems and methods of notifying consumers suffer from severe limitations. It is incapable of reliably recalling and/or locating harmful products and the users of such harmful products.

Interestingly state inspectors had visited the day-care a week before one of the foregoing children died. The day care center's manager also had no idea the crib had been recalled. Despite a recall initiative by the City of Chicago, and the efforts of others, only about 15% of the 1.5 million portable cribs and play yards that were recalled, were actually accounted for. Thus, more than 1.2 million defective cribs remain in circulation. This further demonstrates the inefficiency and limitations of the existing notification and recall methods and systems.

According to Consumer Reports 99Buying Guide "the odds of your hearing about an unsafe product are slim. Manufacturers are reluctant to issue a recall in the first place because they can be costly. And getting the word out to consumers can be haphazard." Likewise, according to the Kids in Danger organization, the only way to be certain that you are not using a recalled product is to check for yourself and periodically check with these government and private agencies about new recalls. Unfortunately, there is no commonly available method or system that actively searches and notifies individually and privately the user for all of the unique products that such users utilize and that informs the user about warnings/recalls for all the products being used by that individual user.

There are also web-sites that send undiscriminating and random recall information for virtually all recalled products, but it is obviously impossible and absolutely inappropriate to randomly send thousands of e-mails every day for each user with the user having to waste an incredible amount of time every day to sort through all of the thousands of daily messages received in order to identify a potentially harmful product that the particular user happens to be using. Furthermore, even if the user identifies among the thousands of daily messages the name of one product being used, the user would have to know if that particular product being used came from the plant or lot or section or processing area that corresponds to the product being recalled. The user then would have to check each package individually to try to find out if he/she has obtained a recalled product. There is consequently a need for a system or method that actively searches for the user and individually informs the user about a recalled product according to precise identification characteristics of the product such as processing plant, section, and the like. Since it is not practical or even appropriate to send thousands of daily messages to each of the millions of users, existing notification schemes select and send one message randomly to the user. There are clear limits and drawbacks to such a scheme. The individual user, for example, cannot afford the significant time, effort, and expense needed to sort through the millions of recalled products to find out which products being used by that user were actually previously recalled and to seek the warning information for each and every product being used by that user. Moreover, the user does not want to be inundated with the millions of recalls and warnings that do not correspond to the products being used by that user. Moreover, this indiscriminate e-mailing has proven to be unable to reach the user of a harmful product in a timely fashion, as the situation with the deadly crib demonstrated, with the tragic death of a second innocent child.

Notably, the existing notification systems tend to be user-based. That is, the user ultimately has to actively search for the recall and warning information about the products being used. Such systems therefore are not product-based and product-driven. There is a need, however, for a product-based and product-driven system and method, wherein an active search is conducted for all of the individual users of a particular product and the specific user of the unique product passively waits for the information about used products to reach him/her. In this regard, there is also a need for a method and system that provides such information to the user as soon as it becomes available.

In 1998 alone, the CPSC recalled more than 38 million individual units concerning harmful children's products. However, because most people never hear about these recalls, the majority of the recalled harmful products are still being used. CPSC usually relies on the media, printed material and manufacturers to recall harmful products voluntarily and most of the manufacturers cooperated. This, however, falls well short of guaranteeing effective results. During the past decade, 622 children have died in defective cribs, a rate of 57 children per year. In addition, at least 137,000 children were hurt. This translates to a rate of almost 400 child injuries per day. CPSC uses various means to inform the public. These include local and national media coverage, publication of numerous booklets and product alerts, a web site, a telephone Hotline, a Fax-On-Demand service, the National Injury Information Clearinghouse, and the CPSC's Public Information Center. There also are several web-sites and other means that publicly announce recalled products. However, they are not sufficient as the figures show. There is consequently a need for new means and technology capable of preventing those tragic events.

According to a CPSC spokesman, recalls also depend heavily on the cooperation of the news media. In the case of the aforementioned crib, the agency issues new press releases every time a child dies in the crib. The crib is also included in the agency's "recall roundup," an annual news release that lists some of the most dangerous recalled products. The CPSC issues hundreds of press releases every year, including video news releases for television stations. This further demonstrates the long-standing need for a system capable of alerting users of potentially harmful products and thereby preventing injury.

Companies also are trying desperately to track and identify the recalled products as can be seen by another press release issued by the manufacturer of the deadly crib, after the death of the second baby in August of 1998. "This is a terrible tragedy we had hoped to prevent when we voluntarily recalled the Playskool Travel-Life crib in 1993 and immediately began extensive public awareness efforts to urge consumers to stop using the products", an officer of the company said in his written statement. The manufacturer said that they franticly have done everything possible to recall the cribs after the death in May 1998. The company has, in fact, extensively advertised using all means, written directly to pediatricians and to all J. C. Penney catalog customers; mailed posters to stores that carried the cribs; set up a toll-free telephone hot line; and offered consumers $60 for the return of each crib (the cribs originally sold for about $89 each). Of course, all of that was not enough and one more child, among the many who died, was strangled to death, and the tragedy repeated.

Another critical issue related to the recall system currently used is the negative impact on the general reputation of business. This indirectly discourages companies from putting forth their best efforts to recall defective products. According to the United States CPSC, underreporting products that could cause injury or death is a very serious problem. This business concern, however, arises primarily because of the means by which both the CPSC and manufacturers inform the public. Typically, the news media and other forms of mass public disclosure are used. The bad publicity through the media has a devastating financial impact on the manufacturer of the recalled product. According to studies by Paul Rubin, former chief economist for the CPSC and professor of economics at Emory University, a company loses 7% of its revenues after each recall. It is easy to recognize the financial disaster faced by companies and the economy of the nation in general when the current, public means are used to alert users of potentially harmful products. There is consequently a need for a system and method capable of privately and individually alerting the user about a recalled and/or harmful product.

The current way of recalling also is very expensive. It therefore is difficult for companies to exert aggressive recall efforts. The federal government likewise is reluctant to impose too many restrictions on manufacturers because it could put hundreds if not thousands of companies out of business with the consequent uncontrolled increase in unemployment and the catastrophic effect on the economy of the nation. Although the government is to some extent charged with the responsibility of ensuring safety and protecting the population, the government is faced with a complex and perplexing challenge. It must balance the interest of safety on the one hand, against its interest in avoiding the consequences of forcing companies to spend money to recall products and to publicly advertise more aggressively their recalls of potentially harmful products (which could lead to increases in bankruptcy and the consequent irreparable damage to the economy of the nation). There is consequently a need to solve these problems associated with conventional recall techniques, by providing a system and method capable of privately and individually identifying, locating, and informing all users of a recalled product.

To find 10 deadly products that were sold to 10 out of 100 million potential purchasers is a daunting and currently virtually impossible task. Thus, 10 people can die because of the deadly effect of the harmful recalled products. Thus, there is a need for a system and method capable of individually identifying each particular product that is being recalled and the particular users of the product, and providing a warning to such users: This need for a system of identifying and warning all users of such potentially harmful products extends to one that, in addition to the savings in terms of lives, injury and costs provided thereby, can be implemented in a cost-efficient manner.

Recently, there has been an increase in the number of foods and other products that are imported and that are more likely to cause unintended harmful effects. Moreover, public sector spending on the consequences of adverse drug reactions is expected to accelerate since prescription drugs grew at double-digit rates during the last few years. This acceleration in prescription drug use can be attributed, at least in part, to the number of new life-saving drugs entering the marketplace, increased consumer demand induced by drug manufacturer advertising, and an increase in the number of prescriptions filled. It is expected that, in the year 2000, each American will use an average of 8 to 9 drugs. This will increase life expectancy and enhance quality of life, but also will cause unintended harmful effects. Besides rising utilization (number of prescriptions); there also will be an increase in intensity (including changes in size and mix of prescriptions) that, in turn, will lead to a greater risk for reactions. It will be virtually impossible to slow the growth on national health expenditures if there is no way to efficiently, privately, and timely identify, locate, prevent and provide guidance regarding potential injury and illness due to unintended harmful effects of products. For extended care, both nursing home and home health expenditures are expected to grow, as more people become disabled due to the unintended harmful effects of a variety of products. Left uncorrected, the number of injuries, illnesses and deaths due to the lack of timely identification and location of users of defective, contaminated products, and drug reactions, as well as illnesses caused by food, will boost the demand for medical services, exponentially increase health care costs, and cause significant increases in income tax to compensate for the rising cost of health care. There is consequently an urgent and vital need for technology that can privately, individually, timely, continuously, confidentially, reliably and/or cost-effectively track, identify, locate, inform and alert all of the users of potentially harmful products. It is also extremely desirable to have a system that returns only specific information relevant to the individual user of a unique product, and not random and/or mass information about a variety of products that do not relate to the user, thus avoiding the unnecessary transfer of information and documents that are not relevant to the user, and making it more practical and convenient (therefore more likely) for the user to become consciously aware of the warning.

SUMMARY

It is a primary object of the present invention to overcome at least one of the foregoing problems by providing a system and method for communicating product recall information, product warnings, or other product-related information to users of such products. The present invention facilitates implementation of an electronic and network-based recall and information system that is product-driven and/or biological variable-driven, to assist the user of the system in timely identifying a health hazard or any other hazardous situation or difficulties due to unintended harmful effects and adverse consequences of a variety of products and/or biological variables, and to prevent the occurrence of such harmful effects. In this regard, the present invention can provide a way of preventing the spread and continuation of such harmful effects, for example, by tracking, identifying, and locating dangerous products, and/or by tracking, identifying, and locating the adverse reactions and adverse effects of drugs, medical devices, food, cosmetics and other consumer products. The present invention therefore allows appropriate action and preventive measures to be taken with respect to the potentially hazardous situation. It can do this by privately, timely, individually, and cost-efficiently locating and alerting the users at risk and/or by providing guidelines to assist such users before any difficulties, damage or injury occurs. According to the present invention, this can be achieved using a portable device into which data is entered using, for example, bar-code technology. The portable device can be associated with a computer-based system in which the information on harmful products is continuously updated by recall and information sources and is automatically transmitted over a public network and/or the Internet. The transmission of such information on harmful products can be performed using a server that receives, retrieves, stores and sends the information on recalled products to a user identified as being a user of such recalled products. The server also can store the information for later retransmission to other users who subsequently enter data indicating that they are users of such recalled products.

Advantages and objects of the present invention can be achieved by providing a completely automatic, electronic, and network-based recall and information system for a variety of products, for interaction among products and/or biological variables adapted to prevent and control any harmful effects of products by providing electronic data communications of such recalls and information. The communication system preferably includes an electronic hand-held portable terminal and a network information system. The portable terminal can include a device capable of acquiring product identifiers and/or biological variables. The network information system can be adapted to assist the user in timely identifying a health hazard or any other hazardous situation or complications due to unintended harmful effects and adverse consequences of a variety of products and/or biological variables, as well as to prevent the occurrence of the harmful effects and to prevent the spread and continuation of such harmful effects. It can do this by tracking, identifying and locating potentially harmful products and the users of such harmful products, and by alerting and informing such users about the adverse reactions and adverse effects of drugs, medical devices, food, cosmetics, other consumer products, and the like. This allows the users of such products to take appropriate action with respect to a possible unintended harmful effect of such products, preferably using a system that can privately, individually, timely, continuously, confidentially, reliably and cost-effectively track, identify, locate and alert all of the users of potentially harmful products with a very low cost, electronically-based arrangement.

The apparatus and methods of the present invention can include an electronic and Internet-based recall system comprising hardware, firmware and software. The system can utilize a database of potentially harmful product utilization and variables such as objective biological variables, and/or objective factors which alter a biological variable, with the objective data, as well as product usage information, being acquired, processed, and transmitted using a computer-based system integrated with a public network such as the Internet, for purposes of precisely locating a user exposed to a hazardous situation in a timely manner, and delivering information/instructions regarding such a hazardous situation or potentially hazardous situation. Preferably, an automated and automatically adjusted and updated system is provided in a reliable and cost-effective manner and is capable of timely and precisely locating and warning a user at risk or exposed to a potentially hazardous situation.

According to a preferred embodiment, the present invention provides a product-based and product-driven system in which reliable product information is used to actively search for all of the individual users of a unique product and all users of products acquire information on each and every product they use, preferably in a passive manner (i.e., the users need not actively seek the information), wherein the acquired information comprises recall information, information regarding potentially harmful effects, and/or information regarding beneficial effects for each and every product used. The product information preferably is delivered instantaneously as soon as the information becomes available. The product recall and warning information for all of the products utilized by each user, in this regard, searches for and finds the user, rather than requiring the user to find the recall and warning information through his/her own efforts.

In accordance with another preferred embodiment, the invention provides a product-based and biological variable-based system having a location, information and recall system that preferably provides electronic transmission of data via the Internet. The product-based and biological variable-based system includes a portable hand-held device (or otherwise portable unit) that can be carried by the user. The portable hand-held unit preferably stores data related to unique product identifications. This data can be acquired, for example, from optically encoded symbols and then can be transmitted to a remotely located central server that is adapted to receive and store the user's product data and a username and also is adapted to receive and store information from remote recall and information sources such as government agencies, private institutions such as medical institutions, manufacturing companies, and the like. The system allows a plurality of users who have product information stored in a database of the central server on their behalf to update and transmit information to the database using a public network, such as the Internet, and to receive feedback information on the products stored in the database. The computer server can send information and warnings about the products for which data is stored in the database, as soon as such information or warnings are received, to all of the users of the products.

These warnings or information can be sent via electronic communication means, preferably through the Internet. The hand-held device carried by the user provides a record of all of the products being utilized by that user and biological variables, which record can be transmitted to the central server by the hand-held device. The system is described herein using the terms username, IP (Internet protocol) address, domain name address, and full Internet address interchangeably to denote a specific confidential address of a user of a product. The combination of the various networks, computer units, users, server(s), and recall and information sources that defines the location, communication and information system according to the principles of the invention is referred to herein as a GPI System (General Product Information System) or Intelligent Systems for Recall and Notification. Any variable that can be measured in a living tissue, for the purpose of the description, is referred to herein as a biological variable or biometric information. Factors which alter biological variables include any physical or chemical action or interaction with/to living tissue that causes any change in, on, or surrounding the living tissue. Any chemical compound that alters any biological variable or any living tissue is referred to herein as a drug. Any network of computers, for the purpose of the description, may be referred herein as the Internet. User, consumer, customer and patient, for the purpose of the description, herein are used interchangeably and denote a living being at risk of harm or death caused by the unintended harmful effect of a product.

It is another object and advantage of the invention to provide a novel electronic recall system that can precisely identify all of the users of a harmful product.

It is still another object and advantage of the invention to provide a novel electronic recall system based on electronic communications via the Internet.

Yet another object and advantage of the invention is to provide an electronic information and location system that can privately and confidentially locate and alert the users of a harmful product.

It is still another object and advantage of the invention to provide an electronic and network-based information and location system that can individually locate and alert the user of a harmful product.

It is still another object and advantage of the invention to provide an electronic and network-based information and location system that can timely locate and alert a user of one or more harmful products.

It is a further object and advantage of the invention to provide a system in which a recall database is continuously updated and items of the database are automatically transmitted electronically.

Still another advantage and object of the invention is to provide a system in which the user of the harmful product can be located and informed about the potential hazard, but the user can remain anonymous throughout the process of tracking and locating the user, and receiving and using the information.

A further advantage and object of the present invention is to provide a system that is continuously updated with the latest product-related information available to the users of potentially harmful products.

It is yet a further advantage and object of the present invention to provide a system that provides only proven information from reliable sources about the products utilized by the user or biological variables acquired by the user.

It is another advantage and object of the invention to provide an alert system in regards to the interaction between dynamically changing biological variables and products as well as product-to-product interaction, with timely identification of the hazard and subsequent institution of treatment or prevention measures specifically tailored for the individual user of a particular product.

Yet another advantage and object of the present invention is to provide guidelines and instructions to assist the user of a potentially harmful product before any insult, illness or injury occurs.

It is also an advantage and object of the present invention to provide an information system not only about the newly found harmful features of products, but also the newly found beneficial features of products.

It is also another advantage and object of the invention to provide an electronically-based cost-effective system for recalling harmful products.

It is still another advantage and object of the invention to provide a reporting system in which the users can report any harmful event that occurred with the use of the product and/or any product contamination, labeling concerns, or questionable product stability.

It is yet another object and advantage of the preset invention to provide a confidential alert system that protects against the financial disaster that invariably occurs to companies which rely on publicly announced recalls.

It is also an object and advantage of the present invention to provide an economically practical way for government agencies and private companies to implement their recall programs.

Another object and advantage of the present invention is to provide a system that can assist the user in identifying substances that the user should avoid without requiring the user to read all of the chemical ingredients described in the label of a product.

It is still another advantage and object of the invention to provide a system that informs the user of the existence of alternative products which do not interact with drugs being used and/or the biological variables of the user, and to inform the user about alternative products which may be beneficial to the user according to the information about the user.

It is still a further advantage and object of the invention to provide a system that offers an opportunity for the user to replace or purchase an alternative product as a replacement to the recalled product.

It is yet a further advantage and object of the invention to provide a system that interfaces with credit card clearing houses and/or retailer's product information storage and processing medium.

It is yet a further object to provide a system with a bar code-based or magnetic-based Safety Card.

It is still a further object of the invention to provide a system that automatically informs credit card users or swipe card users about recalled products purchased using said cards.

It is still a further object and advantage of the invention to provide a system capable of assisting government agencies in their efforts to locate plants that potentially do not have good manufacturing practices, so that such plants can be inspected.

It is yet a further object and advantage of the invention to provide a system to assist government agencies in identifying and locating imported products for collection of samples and inspection.

It is still a further object and advantage of the invention to provide a time-efficient and orderly system of the types described above, using optically encoded symbology.

It is still another advantage and object of the invention to provide a low-cost and simple to use hand-held portable unit that can be universally and unrestrictedly utilized.

It is yet another advantage and object of the invention to provide a novel electronic recall and information system with a hand-held portable unit that can be used by hearing impaired or visually impaired users.

It is still another object and advantage of the invention to provide a system with information cards and smart cards with extended storage capabilities for the tracking, identification and location of a user of a potentially harmful product.

It is another object and advantage of the invention to provide a communication and information system in which the user communicates with a server and receives instantaneous information as to whether such a user is utilizing a recalled product and what level of hazard is presented to the user by exposure to or use of such a product.

Another object and advantage of the present invention is to provide a system in which the users who seek warning or recall information receive only information about the specific products being used, to thereby avoid being inundated with meaningless and/or random product warning information.

Another object and advantage of the present invention is to provide a system that can electronically receive not only text but also image data related to information about the harmful product being used.

Another object and advantage of the present invention is to provide a system that is coupled with the most reliable and updated information sources including government agencies, manufacturers, and the like.

It is a further object and feature of the invention to provide a system for the complete delivery of health care in response to the effects of harmful products, for example, by contacting and dispatching emergency medical services, scheduling an appointment, laboratory testing, and/or other diagnostic testing, prescribing and delivering drugs, and providing insurance approval.

Another object and advantage of the present invention is to provide a system that optimizes the interaction among the pharmacy, insurance agencies, and the user.

Another object and advantage of the present invention is to provide a system that uses non-subjective biological, medical, treatment, and diagnostic data and variables.

It is still a further advantage and object of the invention to provide a tracking, location and identification system that allows specifically tailored information to be delivered to the user.

It is a further object and feature of the invention to provide a system in which a hand-held portable device can communicate with another hand-held portable device.

It is still another object and advantage of the present invention to provide a system that allows the timely intervention and treatment of diseases before complications or/and unintended harmful effects occur.

It is a further object and feature of the invention to provide an interactive system for home monitoring and self-measuring devices.

It is still a further object and advantage of the invention to provide a system capable of incorporating data entry peripheral devices and coupling with various home-use data acquisition and transmission devices, as well as home-monitoring devices, and to provide a system that can communicate with a variety of processing devices.

Another object and advantage of the preset invention is to provide a completely paperless system for recalling harmful products.

It is also an object and advantage of the preset invention to alternatively provide a system that can receive handwritten input data and voice input data, in addition to data that preferably is optically encoded.

It is still a further object and advantage of the present invention to provide a system with an acoustic coupling arrangement that couples the hand-held device with telephone lines to establish a direct connection with a central server and create a two-way telephone communication link.

It is still another object and advantage of the present invention to provide a hand-held device of the type described above that can be attached to a second module, such as a home measuring device.

It is yet another object and advantage of the present invention to provide a system wherein the hand-held device can communicate directly with the central server by telephone lines, optical means, radio frequency links and the like, in order to locate, identify, and inform the user of a harmful product.

The above and other objects and advantages will become more readily apparent when reference is made to the following description taken in conjunction with the accompanying drawings.

BRIEF DESCRIPTION OF THE DRAWINGS

FIGS. 3A and 3B are a perspective view and a block diagram, respectively, of a portable unit according to an exemplary embodiment of the present invention.

FIG. 3C is a front view of an exemplary keypad of the portable unit illustrated in FIGS. 3A and 3B.

FIG. 4 is a schematic view of an exemplary embodiment of the portable unit when provided with a wireless connection to health monitoring devices, according to a preferred embodiment of the present invention.

FIG. 5A is a block diagram of an exemplary general product information system according to the present invention.

FIGS. 5C through 5J are schematic views of exemplary implementations of point-of-transaction systems for gathering product data using a swipe card or smart card, according to the principles of the invention.

FIGS. 5L through 5N are flow charts illustrating an exemplary sequence of operating steps that can be used when transferring product identifiers and acquiring information related to such product identifiers, according to a preferred embodiment of the present invention.

FIGS. 8A through 8C are schematic views of an exemplary memory arrangement according to the principles of the invention.

FIGS. 11A through 11L are flow charts illustrating an exemplary sequence of operating steps that can be used when transferring product identifiers and acquiring information related to such product identifiers.

FIGS. 12A through 12E are flow charts illustrating an exemplary sequence of operating steps that can be used when transferring biological variables and acquiring information related to such biological variables.

FIGS. 13A and 13B are flow charts illustrating an exemplary sequence of operating steps that can be used when acquiring information from remote computers according to the principles of the invention.

FIGS. 14A and 14B are flow charts illustrating another exemplary sequence of operating steps that can be used when acquiring information from remote computers according to the principles of the invention.

FIGS. 15A and 15B are flow charts illustrating another exemplary sequence of operating steps that can be used when acquiring information from remote computers according to the principles of the invention.

FIGS. 17A through 17C are flow charts illustrating exemplary steps that can be performed when acquiring, deleting or using product data provided by the portable unit.

FIGS. 19A and 19B are flow charts illustrating exemplary steps that can be performed when removing data via the portable unit.

FIG. 21 is a block diagram illustrating a system adapted to acquire data and transmit data between IECLD units, according to an exemplary embodiment of the invention.

DETAILED DESCRIPTION

Figure 1:
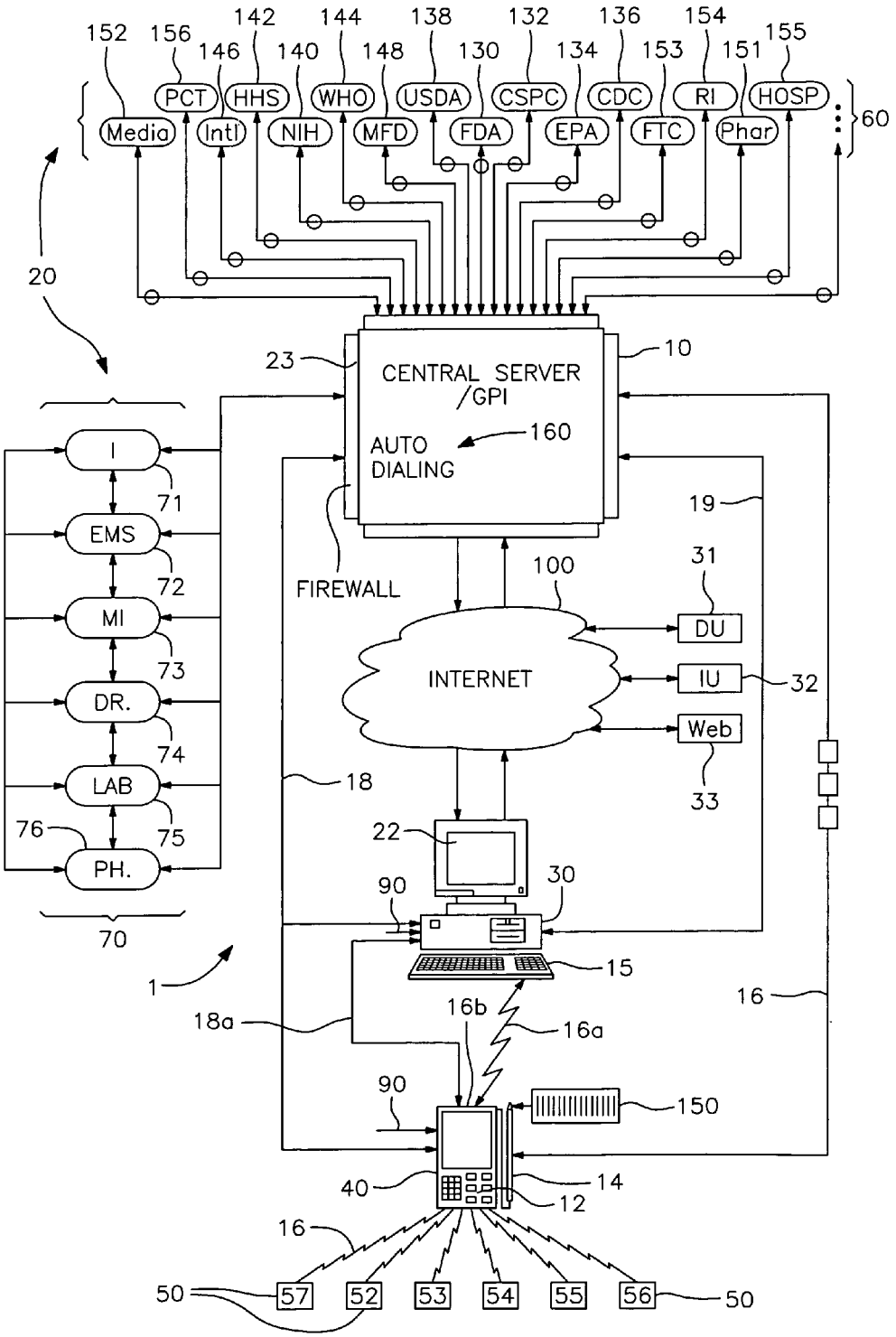
FIG. 1 is a schematic diagram of one exemplary embodiment of a data processing system according to the present invention.

With reference to FIG. 1, a preferred embodiment of the present invention provides an electronic communication, information, and locating system, generally designated by the reference numeral 1, for recalls and information on products and biological variables. The system 1 is capable of preventing and controlling the unintended harmful effects of products. The electronic communications provided by the system 1 preferably are carried out using packet technology via the Internet 100. The system 1 preferably includes a main central server 10 connected to a variety of entities and computers via the Internet 100 (or via any other suitable network such as telephone lines 19, wired means 18 and wireless means 16 including private virtual networks). The central server 10 also can be coupled to one or more microprocessor-based hand-held portable units 40. The portable unit(s) 40 preferably are implemented with bar code reading capabilities.

The embodiment depicted in FIG. 1 includes a central computer that serves as the central server 10 and that is associated with a plurality of remote computers, generally designated by the reference numeral 20, and as well as a plurality of computer systems 30. Some or all of the computer systems 30 can be associated with respective ones of the portable units 40 via wired 18a or wireless 16a means. Each portable unit 40 preferably is implemented using a hand-held, programmable, microprocessor-based unit. The microprocessor-based portable units 40 can be coupled to health monitoring devices 50. The combination of the foregoing units with their respective functions provides an exemplary embodiment of a General Product Information (GPI) system 1 according to the present invention. The system 1 thus can include Recall and Information Sources (RIS) computing units 60, Providers of Health Care (PHC) computing units 70, the aforementioned computer systems 30 (e.g., provided as personal computers), portable computer units 40, home-measuring devices 50, the Internet 100, and data input and output devices such as keyboard(s) 15, display(s) 22, and the like (collectively referred to as interactive devices 15,22). The user 90 may be human, but also can be another computer application which interacts with interactive devices 15,22 or the like, to send information and/or receive information to/from the central server 10. The RIS units 60 and PHC units 70 preferably connect to the Internet 100 using high-speed T1 or T3 connections. Each portable unit 40 or computer system 30 can connect to the Internet 100 using a conventional communications interface (e.g. a modem with suitable software, and the like).

The computer system 30 can be physically embodied in a workstation or a computer terminal, as well as conventional personal computers, such as desk-top computers, lap-top computers, hand-held computers, Personal Digital Assistants, electronic organizers, cellular phones, television units, web-based TV or virtually any suitably configured computation or electronic equipment that can be connected to the Internet 100 or telephone lines 19, or wired means 18 or wireless means 16 for the transfer of information to the user 90, which information includes data regarding uniquely identified products and/or biological variables according to the principles of the invention. As mentioned above, a cellular phone as well as a watch can be used to receive automatic updates about recalled and/or harmful products and can act as the computer system 30 of the invention. While the Internet-based system is preferred, the portable unit 40 and the computer system 30 also can consist of any computation or electronic means capable of transferring and receiving information on uniquely identified products and/or biological variables according to the principles of the invention The hand-held portable unit 40 will be described hereinafter as an Individual Electronic Communicator and Locator Device (IECLD 40). According to an exemplary embodiment of the IECLD 40, the IECLD 40 is connected by the Internet 100 to a main central server 10 that is protected by a suitable firewall 23. The IECLD 40 shown in FIG. 1 comprises a portable hand-held microprocessor-based unit with a keypad 12 for selection of product categories and a bar code reader wand 14. The IECLD 40 is adapted to acquire, process, and transfer data. It is understood, however, that the IECLD 40 can operate while coupled with a computer system 30, preferably of the type described above. The IECLD 40, in addition to having the keypad 12, can be provided with a wireless input device 16b for use when inputting or entering a unique identifier code for individual products used by uniquely identified users 90. The unique product codes preferably are optically encoded (e.g., as a bar code element 150). Although the preferred embodiment includes the IECLD 40 for purposes of acquiring and entering information, it is understood that the users 90 of the product can enter the product data and user data directly into their computer systems 30 using a keyboard 15 for subsequent transmission to the central server 10.

In this disclosure, the central server 10 will be referred to as the General Product Information (GPI) and the source and information entities will be referred to as remote computers 20 or more particularly as Recall and Information Sources (RIS) 60 whereas the providers of health care entities are referred to as Providers of Health Care (PHC) 70.

The system 1 includes the central server 10 (or GPI). The central server 10 can be located remotely from the computer system 30. The central server 10 acquires, receives, retrieves, stores, searches, processes, transfers and connects the data and/or information on products and/or biological variables to/from the user 90 and/or to/from other RIS entities 60 and PHC entities 70. Preferably, this is accomplished via the Internet 100. The central server 10 can establish communication channels with the RIS 60 and PHC 70. The central server 10 also is programmed to handle electronic transfer of data, including conventional e-mail, and has data storage and processing capabilities for storing and processing the pertinent data. To facilitate this process, the server 10 can be provided with multiple modems and telephone lines coming into it through which data is transferred. It is understood, however, that other physically wired telephone lines, or wireless communication links, such as cable, satellite transmission, radio transmission, optical transmission, and the like, as well as conventional telephone phone lines or digital telephone lines, and other electronic transmission means or any electronic transmission over the Internet 100 or any high-speed Internet connection can be used by the central server 10 (or GPI) as a communications medium. The central server 10 (or GPI) preferably contains software, firmware and hardware capable of carrying out any requisite protocols, such as search applications that are well known. The other units of the system 1 preferably comprise devices (such as modems and the like) that enable communications with other units, as well as programs that facilitate implementation of protocols according to the principles of the invention. The GPI system 1 includes information retrieval engines for text and multi-media files and is capable of performing searches through the stored database. The GPI system 1 also can include search engines that search the World Wide Web and equipment to connect the user to web sites related to the search topic. It is understood that the invention is not limited to any particular types of hardware and software, nor is it limited to any particular method of communication, inasmuch as there are virtually endless combinations of technology that can be employed to carry out the present invention.

While the central server 10 (or GPI) is shown schematically in the drawings as one single unit, it is understood that a plurality of networked computers can be employed. This, in turn, allows continuation of service in the event of a hardware failure of a server 10. It also allows the use of larger storage and processing capabilities. The central server 10 (or GPI) operates as the central database where all the unique usernames, unique product identifier codes, biological variables, product and user information, recall/warning information, harmful effects of products, beneficial effects of products, and product-to-biological variable interaction information and product-to-product interaction information are maintained. The stored information can be made available to the user 90 electronically via the Internet 100 or by conventional, physically wired means 18, wireless means 16, or the like.

In the embodiment shown in FIG. 1, the user 90 inputs product identifying information regarding products that are being used, preferably by acquiring the product identifying information from optically encoded symbols (e.g., using a bar code reader 14), and electronically transmits this information to the central server 10 (or GPI), preferably through the Internet 100. The product identifying information can be transmitted as a unique identifier for that individual product, along with an indication of the unique particular user 90 who is or will be using the identified product. The latter indication can be provided using a unique username. The central server 10 (or GPI) transfers information to/from Recall and Information Sources (RIS) 60 and to/from the users 90 of the product while acquiring information from the RIS 60 on products. This information is acquired based on the transmitted product identifier. As shown in FIG. 1, the product identifier preferably is derived from a unique bar code number 150 that is applied to or otherwise associated with each product. The search of the RIS 60 can be performed using automated processors according to applications described hereinafter, which applications interact with and search the Internet 100 and remote computers 20 according to the product identifier. The user 90 thus can provide the unique product identifiers, as well as values for biological variables, to the central server 10 by way of a communication medium such as the Internet 100. The values or other data indicative of the biological variables and product identifiers can be stored in the central server 10 (e.g., in a database of the server 10, as will be described hereinafter) according to the principles of the invention.

When the invention is implemented using the IECLD 40, the unique bar code number 150 for the particular product being used is acquired using the bar code reader 14 present on the IECLD 40. The bar code number 150 representing a unique product identifier then can be converted to a binary number and transmitted using a suitable communication interface to one of the computer systems 30. The binary number derived from the bar code number 150 can be stored at the computer system 30. The product identifying information then can be transmitted to the central server 10 (or GPI), where it can be stored in a memory device (or database) of the central server 10 (or GPI) under the user's name (e.g. under a username with a full Internet address being used to identify the user). Alternatively, the binary number can be transmitted directly from the portable unit 40 (or IECLD) to the central server 10 (or GPI). Every time a new product is used, the data on the product is acquired, transmitted, and stored in the database of the central server 10 under the username of the individual who is submitting the individual product code.

FIG. 1 also shows the various entities and sources that can be connected to the central server 10 (or GPI) via a communications network. Preferably, as shown in FIG. 1, the central server 10 (or GPI) is connected to remote computers 20, which include RIS, at government and private agencies/institutions in the U.S. and abroad, such as, the United States FDA 130 (Food and Drug Administration), the United States CSPC 132 (Consumer Safety Product Commission), the United States EPA 134 (Environment Protection Agency), the United States CDC 136 (Centers for Disease Control), the United States Department of Agriculture (USDA) 138, United States National Institutes of Health (NIH) 140, United States Department of Health and Human Services (HHS) 142, the World Health Organization (WHO) 144 as well as international and domestic agencies and institutions 146 (such as, for example, but not limited to the Japanese Ministry of Health and Welfare, Canadian Food Inspection Agency, German Federal Institute for Drugs and Medical Devices, French Agency for Medicine, the Pharmaceutical Inspectorate in Belgium, the "Secretariat de Salud" in Mexico, the Ministry of Health in Brazil) as well as the U.S. Department of Energy, the U.S. Department of Transportation, and the like. The central server 10 (or GPI) also is connected to other RIS remote computers 60, for example, computers operated by the manufacturers/distributors 148 of the products for which information is stored in the database of the central server 10 (or GPI), medical institutions 152, research facilities 154, public computer terminals (PCT) 156, pharmacies 151, the Federal Trade Commission 153, hospitals 155, and the like. The above named various entities relate to the sources for recall and information relating to the products stored in the memory medium of the central server 10 (or GPI). For purposes of this description, such entities are collectively referred to herein as Recall and Information Sources 60 (RIS). The RIS computers 60 connected to the central server 10 (or GPI) facilitate implementation of the present invention by providing a reliable source of proven information about the products being used. The PCT 156 or Public Computer Terminal mentioned above, for the purpose of the invention, is a computer system located in a public place through which anyone can transfer data on products being used to the central server 10 (or GPI).

FIG. 1 shows the central server 10 (or GPI) connected to the computers for the various RIS 60 via particular links to a communications network (e.g., the Internet 100). The central server 10 (or GPI) also is connected via the Internet 100 to a personal computer 30 of a user 90 or to the portable IECLD 40 of the user 90, with the central server 10 (or GPI) acquiring up-to-the-minute updates on the products stored in the central server 10 database from the institutions and agencies described above as RIS 60. Although each block is labeled as a particular entity/entities or user, the present invention can be implemented using any computing device that performs the computations and communications that are carried out by the entity/entities and/or users. FIG. 1 also shows the central server 10 (or GPI) as being connected to remote computers 20 which include the various providers of health care 70 (i.e., PHC entities). The PHC 70 include one or more insurance companies 71, one or more emergency medical services (EMS) 72, one or more medical institutions (MI) 73, one or more doctor's offices (DR) 74, one or more laboratories (LAB) 75, and/or one or more pharmacies (PH) 76. It is understood that the central server 10 (or GPI) can operate as a web server for both receiving and transmitting product identifiers and/or product information to/from the user 90 and to/from the RIS 60 and to/from the PHC 70 including searching/retrieval for both text and multimedia files related to the product identifier and/or biological variable.

An exemplary embodiment of the system also includes home-monitoring devices herein described as health monitoring devices (HMD) 50 interfaced with the IECLD 40. The interface preferably is a wireless interface 16 through which data can be transmitted. Examples of the home-measuring devices 50 include those patented and/or developed by the Applicant hereof, as well as other devices that are known in the art of home health monitoring and/or doctor's office monitoring. More specific examples of such devices are a self-tonometer for home-measurement of eye pressure 52, a non-invasive blood analysis device 53, a continuous temperature monitoring device 54, a conventional electronic, at-home, blood-pressure monitoring device 55, and a conventional electronic scale 56. In addition, the HMD 50 can include a microfluidics-based intelligent contact lens 57, and/or as shown in FIG. 4, a heart rate and/or rhythm monitor 58. It is understood though that any device that measures any biological variable, physical variable, chemical variables or any device, method, or system used for the delivery of health care including evaluation, diagnosis, monitoring or treatment of patients can be used in the invention as an HMD 50, including any device that has a unique identification and interacts with patients during the process of providing health care, such as diagnosis, monitoring and treatment (e.g., infusion pumps, catheters, ventilators, electrocardiogram (EKG) machines, and the like). The data acquired by such HMD 50 can be transmitted to the central server 10 (or GPI) and can be stored in the central server 10 (or GPI) for further processing and transmission of information back to the user 90 according to the principles of the invention.

Preferably, the electronic information communication system between the central server 10 (or GPI) and the various RIS 60 and also between the central server 10 (or GPI) and the user 90 provides electronic communications using packets of data that are transmitted via the Internet 100. These electronic communications can be performed using hypertext markup language (HTML) or any other electronic communication techniques, using a public or private network as well as direct point-to-point communication 19 via a direct log-in by the user 90 (via his/her portable unit 40 (e.g., an IECLD 40) or his/her computer system 30) into the central server 10, and/or by other electronic or conventional communication means between the central server 10 (or GPI) and the user 90 (e.g., via a private communications network, such as a local area network (LAN), a wide area network (WAN), and the like). The user 90 therefore can communicate electronically with the central server 10 (or GPI) via the Internet 100 or via other ones of the aforementioned connections for information exchange using electronic or conventional communication means. The HMD 50 can communicate with the central server 10 (or GPI) directly by wired or wireless means, via the Internet 100, via the computer system 30 or via the IECLD 40.

The central server 10 (or GPI) also is connected to various PHC computers 70 to enable such PHC to deliver health care according to information received from the various RIS 60 and/or directly provided by the central server 10 (or GPI) with respect to a potentially harmful product. Thus, if a harmful product is known to cause a life-threatening situation that, in turn, requires emergency treatment, the EMS 72 can be contacted and a team dispatched to the residence of the particular user 90 of that harmful product (assuming that user has elected to submit his/her address or other location indicative information to the system 1). If a harmful product is known to cause a medical condition that requires less urgent medical attention, then a doctor's office 74 or medical institution 73 can be contacted and an appointment and transportation arrangements can be made for that particular user of a potentially harmful product. If a harmful product is known to cause a medical condition that requires laboratory testing or further testing, then the type of tests and laboratories 75 where the tests should be done are identified and the information sent to the particular user 90 at risk of injury from use of the harmful product. If the harmful product is known to require treatment with a medication or antidote, then the necessary prescription can be issued by the doctor's office 74 and the appropriate pharmacy 76 can be contacted for delivery of the medications needed by the user 90 of the harmful product.

If information about a uniquely identified harmful or recalled product is received/acquired by the central server 10 (or GPI) from a source such as the FDA 130, CPSC 132 or USDA 138, then the central server 10 (or GPI) searches and retrieves the usernames of all of the users 90 of the harmful or recalled products and preferably electronically sends this information by e-mail to all of the users 90 of such products. This information can include interaction information. The communications involving the central server 10 (or GPI), the RIS 60, and users 90 preferably are carried out automatically by appropriately programmed processors according to the principles of the invention.

An autodialing or paging system 160 also is activated if the user 90 of a product is identified as using a product that requires immediate attention, without the need for emergency equipment and EMS 72. The decisions on what services, if any, are needed can be based on the requisite treatment and/or methods of preventing the harmful effect of a product and can be based on a recommendation from the relevant RIS 60 or the central server 10 (or GPI). A variety of other means can be used to alert the user 90 about an urgent message, such as paging, audio and/or light signal in the computer system 30 or in the IECLD 40, and the like. These can be used in addition to, or as an alternative to, autodialing. Autodialing can include dialing of either a conventional telephone device or a cellular phone with the "Alert" message appearing on the screen of said telephone devices. In this embodiment, either the GPI server 10 does the autodialing or an authorized phone service company does the autodialing. The GPI server 10 or the phone service company can then send the "Alert" message to the screen of a cellular phone as well as to a personal computer or the IECLD 40. The GPI server 10 can be connected to the phone company which then sends the alert message received from the GPI server 10.

As illustrated in FIG. 1, multiple users can be connected to the central server 10 (or GPI). These users can be located in virtually any part of the world. They include domestic users 31, international users 32, as well as one or more web-supported sites 33 of the central server 10 (or GPI). These can be used by anyone to enter and send to the central server 10 (or GPI) via the Internet 100 information regarding the harmful effects encountered with products, thus creating an additional collection system for identifications of potentially harmful products. When appropriate, this information on harmful effects can be sent to the various RIS 60 by the central server 10 (or GPI).

The central server 10 (or GPI), besides receiving information from the various RIS 60, also can be provided with application programs that are adapted to search for information on the products which are stored in the various RIS 60, as well as applications adapted to search for the product identifications and usernames stored in the database defined in the memory of the central server 10 (or GPI). If a product is found to be harmful, or is recalled based on information transmitted or acquired by the central server 10 (or GPI), then the central server 10 (or GPI) can identify and retrieve information concerning all of the users 90 of such harmful product(s). This retrieval can be based on the brand name of the product, or preferably, according to the product's unique code identification number. If there are any matches between usernames and the brand name or unique code number of the product being recalled, then the central server 10 (or GPI) automatically retrieves the relevant usernames or code numbers of all of such users 90 of the harmful product, and attaches the information about the hazards and instructions related to the harmful product to an "Alert" message. The central server 10 (or GPI) then electronically transmits to all of the users 90 of the harmful product the alert and information about the product, preferably utilizing conventional bulk e-mail software or via other electronic and conventional communication means. In addition, or alternatively, the central server 10 (or GPI) can transmit the information to the user's web-based e-mail address when the web-based e-mail is supported by the central server 10 (or GPI). The information transmitted to the user 90 can include textual and/or multimedia documents stored in the central server 10 (or GPI) and also can include the information/documents that can be accessed via the overall system 1 and stored at one or more remotely located computers 20. Likewise, the information can relate to a file that connects to another web site when that web site has the information concerning the harmful product.

Whenever the user 90 sends information to the central server 10 (or GPI), as part of an application and registration process, the user 90 is automatically registered with the central server 10 (GPI) web-based e-mail. Preferably, any product identifications or values of biological variables that are sent by any user 90 automatically causes that user to become registered with the central server 10 (or GPI) and its web-based e-mail, and allows the user 90 to have immediate and confidential access to the information on the potentially harmful or beneficial effects of the unique products being used. Any time information on a harmful product is sent to the central server (or GPI) from the various RIS 60, the information is checked against the database of the central server 10, and if any user 90 is identified as utilizing the harmful product, the warning message and/or instructions about that harmful product are sent to the users 90 via conventional electronic mail, or via the web-based e-mail of the central server 10 (or GPI), and/or is sent via a web site supported by the central server 10 (or GPI) when the user logs onto that web site and proper identification is established. In addition, autodialing or paging or other conventional communication means may be used, in case of critical life-threatening situations and/or in the event that no connection can be achieved via the Internet. The central server 10 (or GPI) also uses conventional keyword, natural language, fuzzy logic, text engines, and other conventional searching tools to find information requested by a user 90 who transmits data to the central server 10 (or GPI) about a particular product and/or biological variable, as well as to find the information on products for which information is stored in the central server 10 (or GPI) and which can be located in the various RIS 60 databases (e.g., FDA 130, CPSC 132, EPA 134, manufacturers 148, and the like). Whenever the central server 10 (or GPI) is configured as a web server, conventional web browsers can be used to transmit product identifiers and biological variables. The system of the invention can use a hypermedia and graphic medium system as information provided via the World Wide Web, with the user 90 of the invention being able to access updated recall information on the drugs and products being utilized by that user 90 from around the world, from any computer terminal with direct communication with the central server 10 (or GPI), via the Internet by logging onto the central server 10 (or GPI) web site, by retrieving his/her e-mail in a conventional manner, or any other means to retrieve electronic data or electronic data transfer, as well as verbal messaging and e-mail with a text-to-speech electronic voice synthesizer, and the like. The central server 10 (or GPI) can be accessed in a variety of ways by the user 90 including via a web site on the Internet, Internet service providers, on-line networks, direct link, and the like. The information from/to the user 90, to/from the central server 10 (or GPI), as well as from/to the central server 10 (or GPI), to/from the remote computers (RIS) 60 preferably uses packet technology. It also is understood that other current and emerging network protocol technologies can be used to carry out the invention according to the principle of the present invention.

The present invention provides a very cost-efficient way of sending and receiving recall and product data using electronic information transfer. The user 90 of the GPI system 1 receives information related solely to the product(s) being used by or otherwise linked with the user 90. This facilitates better and safer utilization of the product. Government and private institutions can send any relevant information to the central server 10 (or GPI), or alternatively, the central server 10 (or GPI) can actively search for the information in the databases. The information about potentially harmful products thus is compared and matched to the current data stored in the database of the central server 10 (or GPI), and the user(s) 90 of that particular product are identified and notified. Whenever the government or the manufacturer issues any information, warnings, or life-threatening alert about a drug or product, bulk web pages and bulk e-mail are transmitted by the central server 10 (or GPI) to all of the users 90 of the unique product related to the warning. This can be accomplished using conventional bulk mailing software with the lists of the users of the products being derived from the database of the central server 10 (or GPI) which, in turn, is the data transmitted by the plurality of users 90 using and otherwise linked with the product identifier. This allows appropriate measures to be taken by all of the users 90 of the unique harmful product. All of the warning messages sent to the user(s) 90 preferably include detailed instructions on what to do and not do concerning the product, including web site information related to the product as well as address, and emergency telephone numbers in case of life-threatening issues, as well as information and/or guidance in regards to their medical condition and how to proceed, including appointment scheduling and laboratory work-ups.

The user 90 also can manually check and/or interrogate the central server 10 (or GPI) for information in regards to alert messages that are stored in the database of the central server 10 (or GPI) as well as factors related to biological functions or factors which alter such biological functions related to products being used, as identified by a suitable product identifier that is transmitted to the central server 10 (or GPI) by a user 90.

Any medical information of an individual is an extremely sensitive and confidential matter, and although encryption means and other applications to protect against attackers can be used when transmitting the medical data of a user, there are few, if any, ways to provide full protection and confidentiality. One of the features of the invention includes a system that keeps the name of the user of the medications and products confidential at all times by using an ID, as can be conventionally done when transmitting information over the Internet. Mr. XYZ, for example, can be used instead of Mr. Jones when registering with the central server 10 (or GPI). A medication "X" therefore is NOT associated with Mr. Gerald M. Jones who lives at 111 Main Street, but with Mr.XYZ@GPI.org. Mr. Jones' identity as the user of the drug thereby is protected. The system of the present invention preferably uses the conventional Domain Name System which allows the user of the potentially harmful product to remain anonymous. The sensitive matter of what type of drugs or products a user is utilizing thus can be kept confidential. Instead of disclosing the user's name, the information about the hazard associated with a certain drug is sent to the user's Internet address under the user's Internet name and address, substantially assuring that any required security and confidentiality is maintained throughout the process of using the product, retrieving information about the user of the product, retrieving information on the recalled products, and sending the information to the user about the recalled products. The information on the recalled product is converted to the appropriate Internet communications protocol for transmission to the user of the harmful product. The system 1 uses the terms IP (Internet protocol) address, domain name address, username, and full Internet address interchangeably to denote a specific confidential address of a user of a product. Each user of any product which has its information stored in the database of the central server 10 (or GPI) has, for example, a specific address such as the IP address and has a username combined with the IP address as it is conventionally done, creating a full Internet address. For example, Mr. Gerald M. Jones is the user of drug "X2", his username is Mr.XYZ, and his full Internet address is Mr.XYZ@GPI.org. The GPI part of the domain name in the present example preferably corresponds to the central server 10 (or GPI) attached to the Internet which receives the information on drugs being used. It is understood, however, that any IP address as a four-part number or any domain name or code can be used according to the invention, as long as it uniquely and preferably confidentially identifies the user of the various products and drugs. The full Internet address is stored in the GPI database of the central server 10 (or GPI), preferably as a username or under a code associated with the full Internet address, and for description herein, each is preferably referred to as username. All of the codes and names of the products used are acquired according to the principles of the invention, then transmitted and stored under the username's code, meaning the user's full Internet address. It is also intended for the purpose of the description herein that the terminology IP address or domain name or full Internet address means the username combined to the IP address or the username combined to the domain name or any other means which uniquely identifies the user 90 of a product, though each may represent a different form of that username.

The central server 10 (or GPI) can be continuously updated on drug "X" by government agencies such as the FDA 130, the manufacturer 148 of the drug, and the like. Thus, information can be received relating to marketing surveillance by the FDA on drug "X". Whenever there is a recall or relevant information by the FDA concerning drug "X", this information is actively or passively transferred to the central server 10 (or GPI) which then searches and identifies all of the anonymous users of drug "X" for whom information is stored in the database of the central server 10 (or GPI). The central server 10 (or GPI) then electronically sends the information and instructions on how to proceed in regards to the use of drug "X" to the user Mr.XYZ@GPI.org, and to all of the other users linked with drug "X", without even the central server 10 (or GPI) or any third parties knowing the true identity of the user. Thus, all of the users are reliably and privately identified, located, and instructed regarding drug "X", or drug "X2" if lot X2 is the one being recalled.

Although the description above involves a person as the user, it is understood that an entity can be considered a user. In this case a business concern, a hospital or a doctor's office are notified about a recalled or harmful product. For instance if a EKG (electrocardiogram) was recalled, the GPI system 1 then will send the notification and information to the hospital and doctor's office which registered the EKG machine with the GPI system 1.

Figure 2:
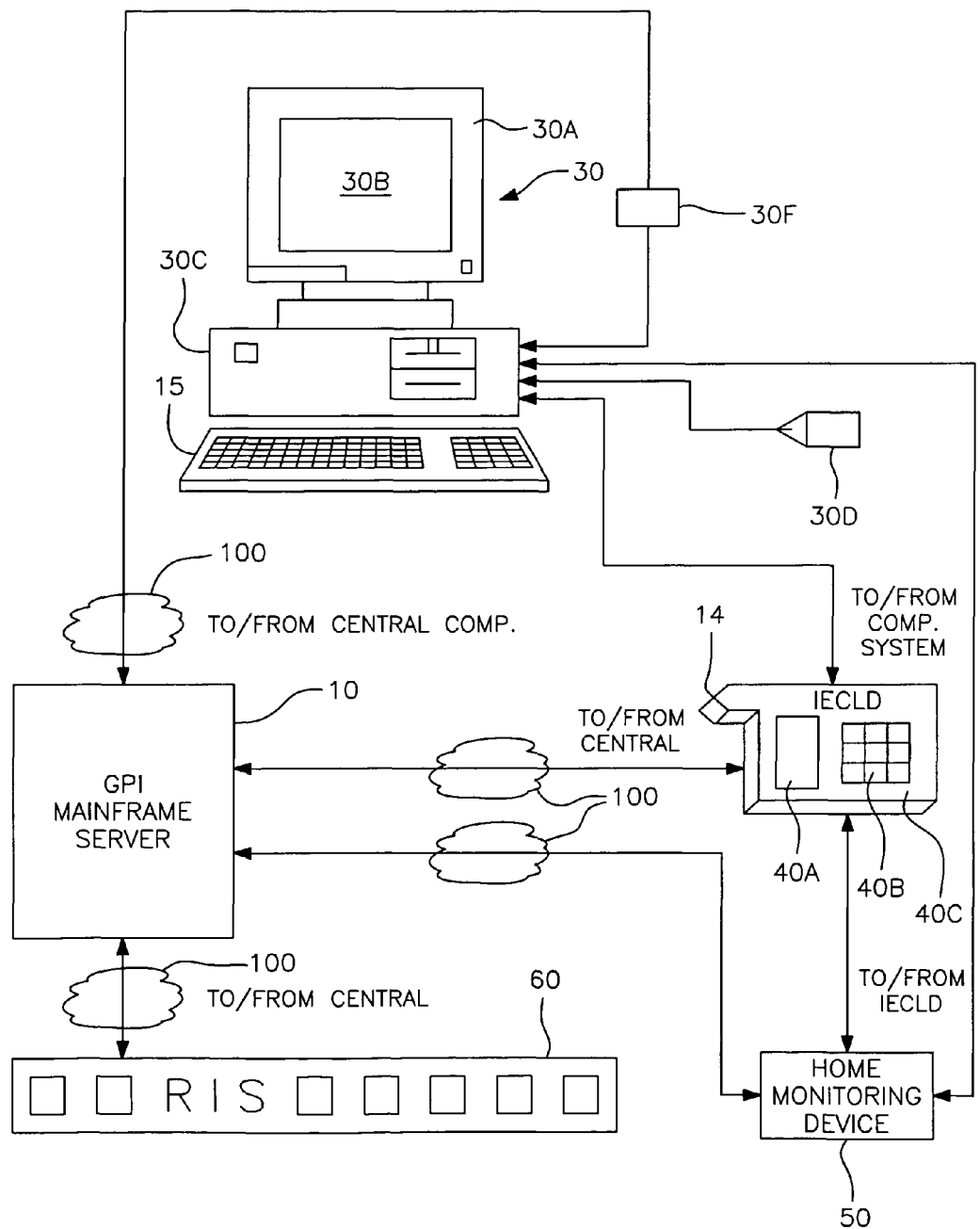
FIG. 2 depicts in more detail a computer system in accordance with the embodiment in FIG. 1.

While the system 1 can be implemented using many different components, FIG. 2 shows a preferred implementation that includes a computer system 30, an IECLD 40, and at least one home-monitoring device 50. The user's computer system 30 includes a display device 30A, a display screen 30B, a housing 30C that encloses standard computer components, interactive devices such as a keyboard 15, and a microphone (not shown), as well as a mouse 30D and a built-in or external modem 30F. The IECLD 40, as shown in FIGS. 2 and 3A to 3C, preferably includes a touch screen 40A (or other display 40AA), a built-in barcode reader 14, a keypad 40B, a housing 40C (that encloses standard computer components), an external antenna 40D (shown in FIG. 3C), an optical transceiver 40E, and a modem 40F. The home monitoring devices 50 can include any of the aforementioned home-monitoring components and structure (e.g., as described by U.S. Pat. No. 5,830,139; No. 6,120,460 and pending applications to Abreu directed to systems and methods for measuring eye pressure or blood sugar by patients at home and other diagnostic and monitoring systems).

FIG. 2 also illustratively shows the flow of data and information to and from the computer systems 30, portable units 40, RIS computers 60, and the central server 10 (or GPI), with the flow of data preferably being controlled by the central server 10 (or GPI) and being routed over the Internet 100.

The central server 10 (or GPI) keeps track of all of the recall information provided and/or retrieved from the various RIS computers 60 and then locates the unique user(s) 90 of a particular product. The central server 10 (or GPI) uses standard applications to search for recalled products and/or receives information about recalled products from the various RIS 60. If a recalled product or a harmful or beneficial effect is found, the central server 10 (or GPI) retrieves and stores the name or preferably the code number for that harmful product in its database, and then searches for usernames associated with people who are using the harmful product. It also matches the code sent by the RIS 60 with the code of the products being used under the username. If there are harmful product codes under one or more usernames, then the usernames are retrieved, and the level of severity or risk of the hazard is evaluated. Hazard degrees preferably are identified by a code of 1 to 5. If hazard degree codes 1 to 3 are found in the warning information received (1=minimal, 2=moderate, and 3=high), and an affected username(s) has (have) an active Internet address, then conventional bulk e-mail software is used to electronically send the warning message and/or web pages on the harmful product to all of the people with usernames associated with the code for the harmful product. If hazard degree code 4 (4=critical) is found in the warning information received, then e-mail with a warning message and/or web pages on the harmful product are sent, and an autodialing or paging terminal which dials all of the users of the potentially deadly product is activated to inform the users by conventional computerized voice messaging techniques about the potentially fatal reactions or other problems associated with the harmful product. In this manner, the user is advised to check the GPI web site and the GPI e-mail. If emergency care with risk for fatal reaction is present (hazard degree code=5), then the EMS 72 is contacted and dispatched, assuming the user has enabled the system 1 to obtain his/her address.

It is understood that depending on the level of severity, a variety of audible and/or visible signals can be used, each of which corresponds to the respective level of severity. Such signals can be displayed on the screen of the computer systems 30 including the screen of a telephone or IECLD 40. When the RIS 60 transfers warning information via the Internet to the central server 10 (or GPI) concerning a newly found recalled product or harmful product, then the central server (or GPI) can immediately send a request to check its database for any usernames that are associated with the harmful product code number. When the username(s) associated with the harmful product is identified, the central server 10 (or GPI) matches the usernames with the alert message and/or web pages and sends the resulting compilation to all of the users represented by the matching usernames, and according to the level of severity as previously described (hazard degree 1 to 5). Alternatively, if only the names of the products are used (e.g., in the case of a comprehensive recall) or when no hazard codes are available, then the central server 10 (or GPI) uses the name of the product and warning information, without a hazard code, in order to identify, locate and warn the users of the product in the same manner as described above.

The information about products (codes and/or names) being used and stored in the central server 10 (or GPI), can be accessed only by the users of such products. They preferably are required to enter a proper identification and password. To further assure the confidentiality of the information about products being used, biometric identification devices such as iris scanners, retinal scanners, fingerprint readers, voice recognition systems, and the like can be used to verify the identity of the user before accessing the database of the central server 10 or using the IECLD 40. The biometric data system also can be used by users who are visually or hearing impaired. The central server 10 (or GPI) can continuously receive and/or acquire updates on products, with the new information about the harmful products immediately being transmitted to the unique user of such harmful products. A menu-type message can be generated with the most critical hazard placed first and with a decreasing order of severity presented when the message/warning is transmitted. Certain information, such as the cardiac effects of products being used, can be stored and thus the user has the option to store and index the particular information in the database of the central server 10 (or GPI) under his/her username, which enables the user to review products which are or were used that affect the heart, and this information can be transferred to the user's doctor as well.

The central server 10 (or GPI) also checks the presence and/or values of the biological variables of the user and determines whether any abnormal values have been detected and/or whether the user has failed to comply with a prescribed schedule for monitoring of biological variables (i.e., determining whether there has been an episode of non-compliance with timely monitoring of biological variables). If the user has, for instance, not sent or has not recorded blood sugar levels in the last week and the user is diabetic, then the central server 10 (or GPI) sends a message to the user to inform and encourage the user to monitor his/her blood sugar according to the time criteria set by the doctor.

The acquisition and transmission of signals corresponding to biological data or factors which alter the biological data is accomplished utilizing the hand-held portable unit 40 (or IECLD 40), with electronic data being communicated over a public network such as the Internet to the central server 10 (or GPI). This provides feedback information according to the biological and/or product data electronically received. The electronic feedback data is automatically transmitted back to the user's computer system 30 and/or the user's IECLD 40. It is understood, however, that any computer terminal connected to the Internet can be used by the user 90 to receive the information on biological variables according to the principle of the invention.

A preferred IECLD 40 will now be described. It is understood that the IECLD 40 is preferably a portable device with bar code reading capabilities for the input and output of data. Other forms of inputting/outputting data, however, can be used such as a personal computer keyboard and the like, in accordance with the present invention. In addition, or alternatively, data input/output can be accomplished using RF or optical input, or an on-screen keyboard with the data being entered by a medical practitioner, health care professionals, clerks, or the users 90 themselves.

Referring to FIGS. 3A-3C and 4, a preferred embodiment of the portable Individual Electronic Communicator and Locator Device 40 (IECLD 40) comprises a portable unit 40 which can be carried by the user and utilized by a particular individual to acquire, process, transmit and receive information on biological variables and products being used by the particular individual. The IECLD 40 can include a housing 40C that contains a conventional, programmed microprocessor 40G with data processing and storage units, and which controls the operation of the portable unit 40. Communication interfaces and communication ports 40I can be provided with the IECLD 40, as well as a built-in bar code reader 14, warning lights 40H, optical transceiver 40E (e.g., exposed through the housing 40C and preferably working in the infrared wavelength), and a numerical keypad 40B. A modified keypad 40BB may also be provided, designed for the five main types of products that can be recalled and enabling manual selection of the type of product being scanned. The five main types of products are drugs, medical devices, toys and baby products, cosmetics, and food. A miscellaneous key 40BBB is also provided. The IR optical transceiver 40E receives/transmits signals, such as biological data acquired from home monitoring devices 50. It also is coupled with other interfaces (e.g., 40D and 40I) to transmit signals, such as biological variables or/and product identifiers to a computer system 30.

The computer system 30 preferably is connected to the Internet. The portable unit 40 preferably is provided with a variety of software applications and decoding elements for optically encoded symbology, with a system configuration including a scanner module for bar code reading. Alternatively, the hand-held terminal IECLD 40 may be provided with voice input and/or voice synthesizer modules and/or means for handwritten input data and/or typed input data and/or manual data entry with an electronic keypad. It is understood that any type of product group such as, for example, household items could be used, but these are less likely to cause substantial and frequent harm and increased health care costs as compared with the above main five categories preferably used (drugs, cosmetics, food, baby/toy products, medical devices), and such other types of products are included under miscellaneous. It is intended that any variations or group products could be selected with keypads or using a touch screen addressing other group products, or the device preferably may have all products stored by product, according to their identifier numbers. Alternatively, the device can be programmed to address particular groups of products such as, but not limited to, automotives, appliances, furniture, lighting products, outdoor products, clothing, electronic devices, electrical devices, environmental products such air conditioners, household products, sports/exercise, and so forth.

Figure 3B:
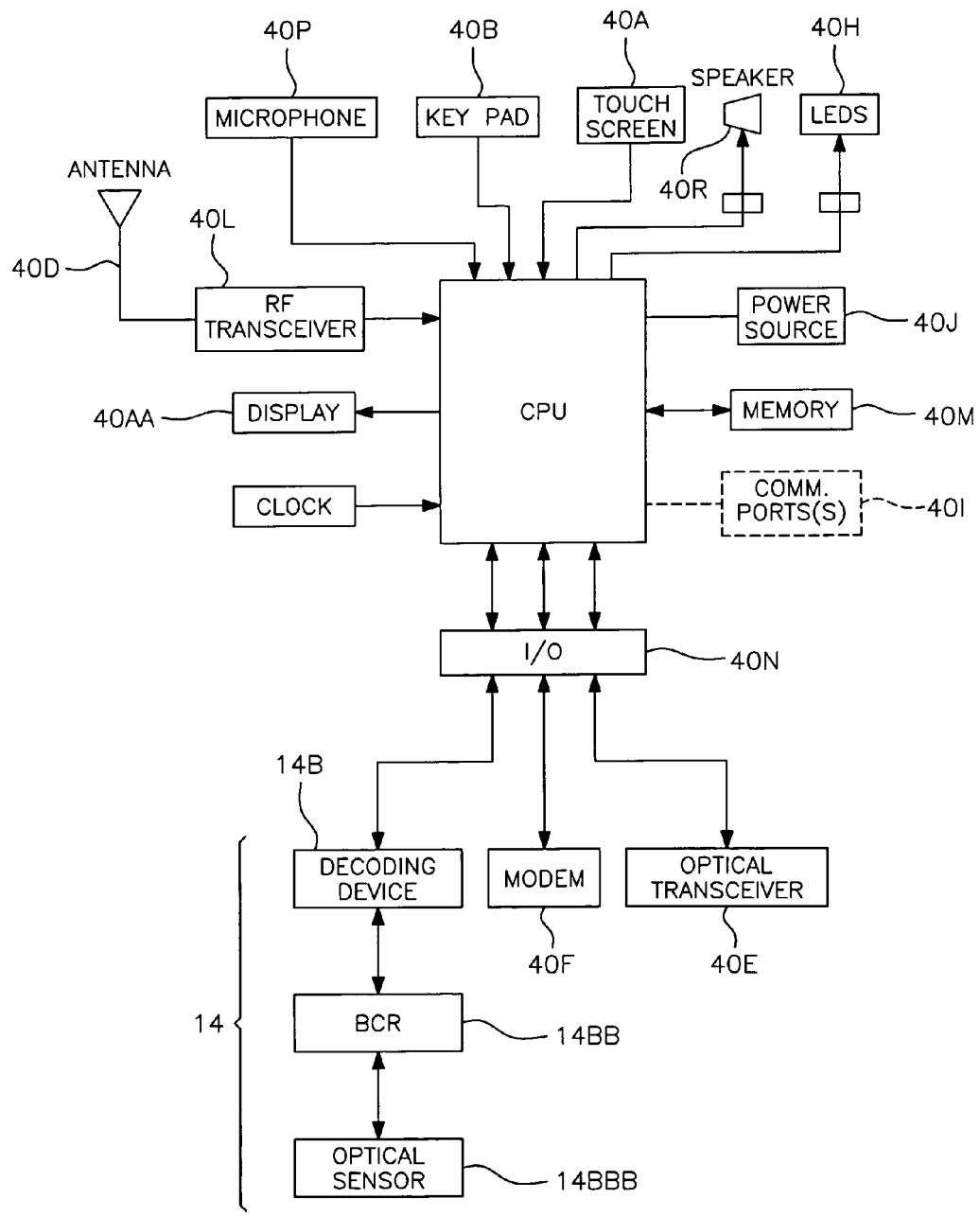

The block diagram of FIG. 3B shows an exemplary IECLD 40 comprising communication ports 40I, a power source 40J, a conventional modem 40F which can be connected to the central server 10 via electronic or conventional communication means, an RF transceiver/modem 40L coupled to an antenna 40D for wireless transfer of data, non-volatile RAM memory 40M, I/O ports 40N, an optical transceiver 40E, an optical sensor/bar code reader 14 with decoding devices 14B, visual indicators (e.g., warning lights 40H) and audible indicators (e.g., speaker 40R), a microphone 40P, and a display 40A or 40AA. At least one output from the microprocessor 40G is supplied to the display 40A,40AA through a conventional LCD driver circuit that conventionally decodes and multiplexes the data to be applied to the display 40A,40AA as well as known parts of a computer arrangement, such as random access memory (RAM), read-only memory (ROM), and the like.

The bar code reader (BCR) apparatus 14 includes a decoding device 14B, a code reader device 14BB and an optical sensor 14BBB. The BCR apparatus 14 preferably is used because of its low-cost and low-power requirements. It can include an LED bar code reader with low-light levels and preferably is implemented using a direct contact type of bar code reader. While it is understood that non-contact types of bar code readers, such as laser-based ones, can be used with the invention, they tend to be more expensive and tend to consume more power. Virtually any bar code reading technology can be used with the present invention including, but not limited to, imaging technology, CCDs, and the like. The system 1 also allows for direct wired and wireless communication and duplex transmission with the central server 10 (or GPI). While the input of product identification information preferably is accomplished using the bar code reader, manual entry using the keypad or RF wireless input of product identification or any conventional wired or wireless input of product identification also can be used. The IECLD 40 also has conventional encoding and decoding programs which allow the IECLD 40 user to read messages as well as to view multimedia files related to products used by the user 90, using the information transferred from the central server (or GPI).

In an exemplary embodiment, data such as drugs used by a patient is entered by scanning a newly created bar code element preferably separated from the conventional UPC code. The new product identifier of the present invention encodes information about the name and characteristics of the drug, date of manufacturing, plant location, serial number, and lot number, into what will be called hereinafter BarCodeData (BCD) or unique product identifier (UPI). Although UPI is used in the description, it is understood that the conventional NDC (National Drug Code) bar code can be used. The NDC has eleven digits corresponding to the following: first five digits provide information on the manufacturer, next four digits indicate the name and type of drug, and the last two digits provide packaging information. BCD or UPI is a unique identifier of the product and the characteristics of the product, such as concentration and strength, expiration date, serial number, plant number, date of manufacturing, and lot number. The UPI can be optically encoded in a PDF417 format which, due to the high information density and capacity, can include all of the information regarding the individual product, including even test summaries, components, ingredients and parts used, personnel involved in the manufacturing of the product, manufacturing process, color additive(s) used when coating pills, and so forth. Thus, the UPI when optically encoded gives all of the information necessary for the recall of any particular individual and single product or ingredient of that product such as color additives present in drugs and foods. It is important to note that the conventional UPC codes consist of a Universal Product Code which is universal and does not encode detailed characteristics of the product, as might be needed for certain recalls of individual and single products or of a certain number of units of the product from a lot with the same UPC code. Thus, the currently used UPC does not allow a single and individual recalled product to be located. If a company, for example, has sold five million units of a certain over-the-counter drug, and 5,000 units from three lots were contaminated, then a recall of only the 5000 units is difficult to perform using the conventional UPC code. Instead, the recall probably would involve identifying and notifying all of the 5 million users. Using the UPI system according to a preferred embodiment of the present invention, it is possible to limit the recall to the 5,000 users who actually bought the product from the tampered lots. Thus, while the system 1 is generally effective when implemented based on the conventional UPC code, additional benefits can be realized using the UPI system of the present invention. Using the aforementioned UPI, only the 5,000 users at risk would be located and warned, thus creating a significantly more cost-effective recall system for the users, the companies, and the government.

The BCD or UPI may be used separately but also possibly in combination with the conventional UPC code. For instance the addition and/or substitution of a few encoded symbol or numbers to the UPC could provide the needed unique identifier data as described above, and thus could be easily implemented to provide a modified UPC, which also would fall within the definition of UPI for the purposes of this disclosure. This modified UPC is easier to implement and thus represents the preferred embodiment. It should be emphasized that the "U" of UPI stands for Unique, which is completely contrary to "U" of UPC, which stands for Universal. The UPI arrangement provided by the present invention therefore distinguishes from the UPC arrangement, at least because it uniquely identifies a product utilizing optically encoded symbology in an unique manner.

The UPI system allows a variety of potentially hazards elements to be encoded, including color additives. All drugs or/and food that contain certain potentially dangerous additives could be identified in this fashion. For instance, color additive Red FD&C No. 2 was shown to significantly cause tumors in female rats and has been banned as unsafe. Color additive Red FD&C No. 3 has been found to cause thyroid tumors in male rats but has not yet been considered unsafe and removed from the market. As soon as the information is available, the user at risk is informed, before the product is removed from the market by authorities. For instance, if the user has a family history of thyroid cancer, the user would have the opportunity to make an educated choice and avoid food and drugs that contain Red FD&C No. 3 based on the alert with respect to foods and drugs that can be provided by the central server 10 (or GPI) according to the principles of the invention. The information preferably is sent only to users with a personal or family history of thyroid cancer according to information stored in the users' personal information database 700 (as will be described hereinafter), and not randomly, thus optimizing the use of electronic data transfer. It is very difficult for the average individual to be aware of harmful products including harmful color additives. Although the additives are printed in the label, the information is often meaningless for the average user. Furthermore, even when the user has knowledge of additives, the user most likely would still not know the latest information in regards to harm caused by such additives. Since the system 1 is continuously updated with respect to this type of information about harmful products, the user has the advantage of passively receiving this updated information without being required to read the label and/or be knowledgeable about the barely publicized effects of chemicals that are present in products being used.

For the purposes of this description, the UPI can be a modified UPC, a separate bar code from the UPC, a two-dimensional bar code with or without the UPC, or any other machine readable format that uniquely identifies a product according to the principles of the invention. There are some situations in which the conventional UPC could be used. For example, if the total number of units sold is similar to the number of units tampered with, for instance according to the above example, if 5,000 units are recalled, but the total number of units sold is less than 6,000, or if the recalled units pose an immediate and 100% fatal threat, then a comprehensive recall using the UPC code could be used. The UPC can also be used in association with the date of purchase to minimize or eliminate the return of any good products. In this embodiment, the date of purchase is used and, based on the standard "first in first out" approach used by business concerns, the GPI system 1 can identify the harmful products in a more precise manner. For example, a non-perishable product (UPC 12345) with defective units arrived at the point-of-sale on January 2. A second lot with non-defective products but with the same UPC 12345 arrived on April $1^{st}$. Only on April $30^{th}$ was it noted that the lot delivered in January contained defective harmful product. Good products could have been sold with defective products in the month of April. Thus to minimize return of good products, the GPI system 1 sends two different "Alert" messages according to the date of purchase. Purchase dates up to April $1^{st}$ identify the consumer as acquiring a defective product. Purchase dates between April $1^{st}$ and $30^{th}$ identify the consumer as likely acquiring a defective harmful product and state "Please check lot number; if 11A, please stop using it and return it to vendor". It is most likely that, due to "first in first out", purchases around April $30^{th}$ do not include defective harmful products and in 60 days most products are out of the inventory. The above method and system also applies to perishable items but since those items have expiration dates, there is less risk of harm arising from long term storage or use of the product. As can be seen, although UPC can be used to practice the invention, the preferred way is to use the UPI (Unique Product Identifier).

The bar code element UPI is a unique identifier of, for example, drug "X". The UPI is then converted to binary data and is transmitted using a communication interface to the central server 10 and stored as a binary number (e.g., 0100 . . . 0110 for drug "X"). The information on drug "X" is stored in the memory of the portable unit 40 with the data regarding drug "X" being automatically electronically transmitted over the Internet to the central server 10 (or GPI). If, for instance, the user Mr. Gerald M. Jones starts using a drug "X" that came from a different lot, for example, one that included a new coating with a new color additive, then a new unique bar code element for that product is used, and the new data is stored as for instance "X1" with a binary-converted UPI No. of 0100 . . . 0111. If Mr. Gerald M. M. Jones starts using a drug "X" which comes with a tablet of larger size, then a new unique bar code element is used to identify the product and is stored, for instance, as "X2" (e.g., using a binary UPI number of 0100 . . . 0112), and then "X3" (UPI 0100 . . . 0113) for a formula manufactured abroad, and so on. Data entry using optically encoded symbology provides a virtually error-free entry system and a time-efficient and cost-efficient mode contrary to written and/or manually entered or typed data. The large amount of data on the characteristics of medication "X" is conveniently and automatically acquired as a bar code number, and then processed, and transmitted over a public network such as the Internet to the central server 10 (or GPI). The computer system 30 or portable unit 40 of the user and/or the GPI central server 10 can contain the name equivalent data that can be used to generate the name of the products scanned according to their UPI.

The bar code reader 14 acquires the information on the characteristics of the product which are necessary for precise identification in case of a recall, with the data preferably being transferred directly from the portable unit IECLD 40 to the GPI central server 10. Alternatively, the identification data on the products can be transmitted later to the user's computer system 30 via IR means 40E, RF means 40L and/or 40D, or via conventional physically-wired downloading means with the processor executing the programs in the memory 40M necessary to carry out the function. The IECLD 40 includes a memory that stores the data about the product, and communications port(s) 40I, for downloading the data to the user's computer system 30, with the user's computer system 30 having capabilities to connect with the GPI central server 10 via the Internet. Preferably, the portable unit 40 or IECLD 40 includes computer terminal components having capabilities to directly connect with the Internet, thus bypassing the user's computer system 30 (e.g., a personal computer or desktop computer). The IECLD 40 also provides for duplex communication to and from the GPI central server 10 using conventional direct communication via telephone lines or wireless communication via the RF transceiver 40L. The bar code data related to the precise identification of the product and biological variables acquired by the portable hand-held device 40 is uploaded to the central server 10 (or GPI) for storage via conventional or electronic communication devices. The processing and transmission of data can be performed by the microprocessor 40G, using conventional applications. The data generated by the microprocessor 40G also, or alternatively, can be supplied to the user's computer system 30 using a typical wireless transmission.

The portable IECLD 40 provides means for entry, storage, processing and transmission of the unique characteristics of a product and biological variables to or into the central server 10 (or GPI). The central server 10 then checks its database in order to update and/or generate information according to the data transmitted by the portable IECLD 40. According to the principles of the invention, if there is any information stored that corresponds to a recalled product or the product identifiers transferred are indicative of a product that can cause a harmful or life-threatening event, the information is retrieved and is sent immediately as an "Alert" message which is then transferred back to the individual user of the product, as previously described. Since the IECLD 40 is portable, hand-held and compact, the IECLD 40 can be easily carried to different places and during trips and thus can have applications in virtually any environment including, but not limited to, doctor's offices, hospitals, pharmacies, grocery-stores, department stores, hotels, and the like, allowing easy acquisition of information on products being used as well as easy retrieval of information by directly connecting the IECLD 40 with the Internet and directly accessing the central server 10 (or GPI) for the information about recall in regards to the products being utilized by the user. The IECLD 40 can also include GPS (global positioning system). This can be used to locate the user in case said user is exposed to fatal injury/illness by using a harmful product and does not respond (there is no read receipt).

FIG. 3C shows a frontal view of the housing 40C with a modified keypad 40BB, for selection of product groups before product information is entered. FIG. 4 shows the IECLD 40 coupled to home-measuring devices 50, such as a self-tonometer 52 to measure eye pressure at home, as previously described by Abreu, a non-invasive self-measurement system for blood glucose 53, as described by Abreu; a continuous temperature measuring device 54 (shown in FIG. 1) as described by Abreu; a heart rate and rhythm monitor 59; as well as a conventional electronic blood pressure measuring device 55, electronic scale 57, and a microfluidics-based intelligent contact lens 57. It is understood, however, that any other device capable of measuring any physical or chemical biological variable can be used in the present invention. An optical transceiver 40E mounted in the housing 40C of the IECLD 40 establishes communication with the various home-monitoring devices and receives and stores the information on the values of the many biological variables, such as eye pressure, blood glucose, temperature, blood pressure, weight, and the like. Data is transmitted and received by the microprocessor 40G through the optical transceiver 40E by conventional means of transmitting light signals. It is understood that the values of the biological variables can be entered manually into the IECLD 40 or by RF transmission (e.g. using RF transceiver 40L) as described by Abreu, but a more cost-efficient system involves the optically automated transmission of the biological variable values. The optical transceiver 40E establishes data communication in bit serial format between the IECLD 40 and the user's computer system 30. The user's computer system 30 is connected to the central server 10 (or GPI). It is understood that the IECLD 40 preferably acts as the user computer system 30 with a direct connection between the IECLD 40 and the central server 10 (or GPI), without the need for the user's computer system 30. In this regard, the IECLD 40 can acquire and transmit to the central server 10 both biological variables and product identification information. The acquisition, storage and transmission of data preferably are performed via programming within the IECLD 40, for example, using standard techniques. It also is understood that any means for transferring biological variables via a network such as the Internet 100 can be employed by the present invention. The biological variables can be analyzed against the product identification information stored in the database of the central server 10 (or GPI) for the evaluation of potential interaction of the products with the biological variables or potential harm caused by abnormal values of biological variables.

Although the IECLD 40 is preferably designed to be used by one person, more than one user can have his/her individual data in the microprocessor-based portable IECLD 40. Naturally the user can select what products or type of products the user is interested in receiving recall or warning information concerning, and thus if the user does not purchase or use baby products, the user has the option of not acquiring the information or/and not transmitting the information and/or selecting not to receive recall/warnings on the particular product. The user can at its sole discretion cancel or add any products or group of products and/or biological variables to the main GPI database at any time. Besides the user actively deleting items, the principle of the invention also includes an expiration date for some of the products entered such as perishables and ready-to-consume items as certain foods, drugs, cosmetics, and so on, so that the stored database for the user does not grow too large and products are not kept in the database for an excessive period of time.

Furthermore if a user brings his/her IECLD 40 to the doctor's office, a drug being prescribed may be entered and if there is a medical reason for the drug not to be prescribed or a drug interaction, then an alert will be displayed in the display before the patient buys or starts using the drug, and subsequent to that the GPI gives alternative drugs for the condition. For example, a general practitioner may prescribe a drug to control heart rhythm, such as amiodarone, to a patient. This patient has stored in his IECLD 40 medical information which includes measurement of his biological variables with a record of elevated eye pressure which put that patient at risk for optic nerve injury. Now considering that amiodarone was found to cause optic neuropathy as an adverse reaction, then the system identifies the potential harmful interaction between the drug being prescribed (amiodarone) and the biological variable measured (elevated eye pressure) and alerts the user and the doctors. The GPI system 1 then sends alternative drugs that treat arrhythmia but without any adverse effect considering the user health status according to the biological variables transferred. Naturally the patient also could be made aware of the harmful interaction drug-biological variable at the point-of-sale or in the pharmacy by sending the information to the GPI server 10, or at home by uploading the information to the GPI server 10 and thus receiving the warning.

The apparatus and methods of the present invention allow acquisition, storage, transmission, and processing of objective biological function and variables, as well as objective factors that can alter the biological variables, such as the use of a variety of products. The system of the invention provides a display of the alert information needed by the previously located user, as well as information on how to manage the hazardous situation. Also provided are automatic updates of information and guidance according to chronological changes of the biological variables that would be otherwise undetected, thereby permitting the user to take timely appropriate action and establish control over the hazardous situation.

The system 1 of the invention provides not only display and guidance/instructions on currently known hazardous situations, but also may predict and warn the user of the potential for a hazardous situation to occur before it takes place by continuously analyzing the data that is transmitted for the purpose of intermittently providing information and alerting the user about potential imminent hazardous situations. The system 1 sets the criteria according to the data received from the user and the criteria is continuously adjusted in a graded manner, in accordance with the updated data that is transmitted by the user and RIS 60. If the criteria are met, the user automatically receives a warning/information about the potentially hazardous situation and/or guidance/instruction without interference from subjective considerations, nor the need for a human observer to select the information. The system 1 of the invention also provides and displays information to the user about transmitted biological variables, or factors that alter such biological variables, with the purpose of improving understanding and comprehension regarding the biological variables, disease states or factors that may alter biological variables, such as interactions with drugs and other products.

Figure 5B:
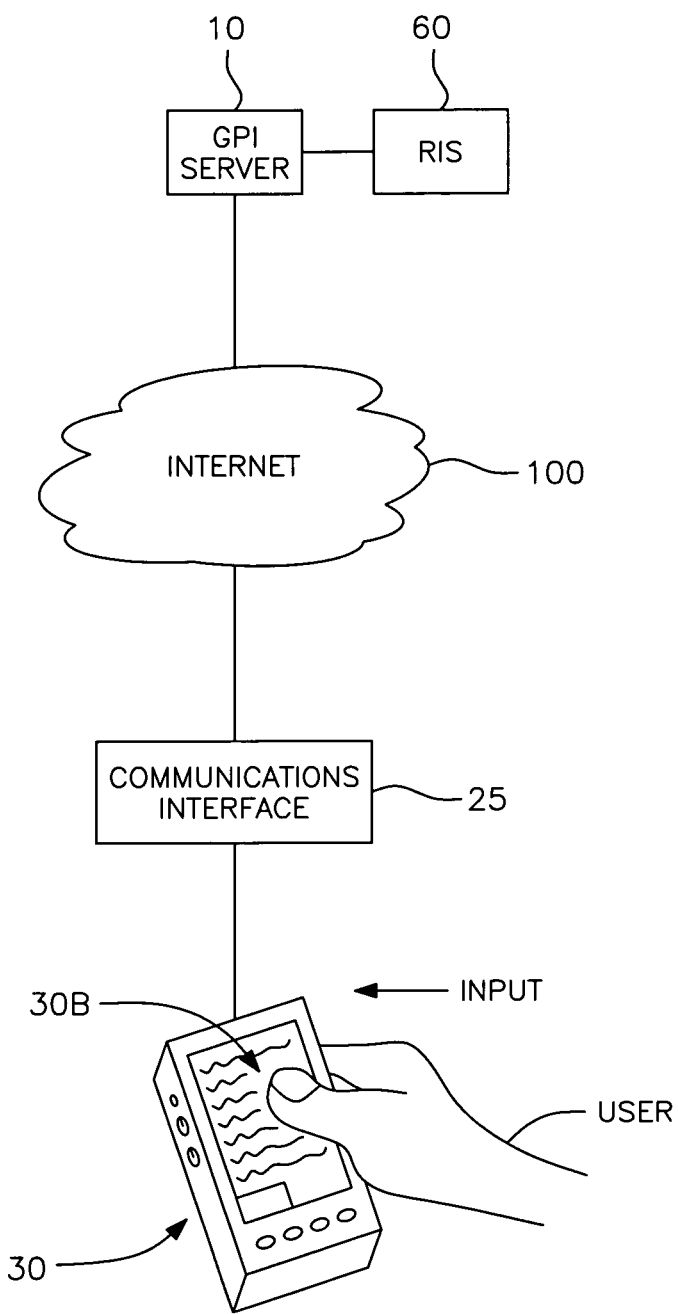
FIG. 5B is a block diagram of a general product information system similar to that of FIG. 5A but implemented using a portable unit, instead of a desk-top personal computer, and showing an exemplary screen that can be displayed by the portable unit.

Referring now to FIG. 5A, there is depicted a simplified version of the system 1. The simplified version includes, for the user 90, an input device for manual entry such as the keyboard 15 of a computer system 30, a communications interface 25, a central server 10 (or GPI), and the RIS 60 and/or PHC 70. The computer system 30 can be implemented using a typical personal computer having input means such as a keyboard 15, a microphone, a mouse, and/or the like, a processor, a display element, and a network interface. The computer system 30 likewise can include a CPU, ROM, RAM, input device, memory device, video driver, video monitor, clock and modem. While FIG. 5A shows a desk-top computer system 30, it is understood that a hand-held computer 30, as shown in FIG. 5B, can be used instead of a traditional desk-top computer. The personal digital assistant 30 can have an electronic architecture similar to that of the desk-top computer system depicted in FIG. 5A and can work in a similar manner. The computer system 30 in FIG. 5B, however, preferably includes a touch-screen display 30B that facilitates manual entry of product information or other information. Also shown in FIG. 5B are the communications interface 25, a central server 10, and the RIS 60.

With reference to FIGS. 5C-5F, transaction terminal equipment, generally designated by the reference numeral 39, can be used at a point-of-transaction (e.g., a point-of-sale) to connect the point-of-transaction to the central server 10. Using this equipment 39, it is possible to transfer unique product identifiers to the central server 10, without the need for duplicating the entry of product information or double-scanning of the product, i.e., once at the point-of-transaction to consummate the transaction and then again at home or elsewhere when data is to be entered into the system 1. Thus, a single scan at the point-of-transaction will suffice for both purposes. While the user can provide a user identification number or other identifier that is manually keyed into the equipment 39, it is more desirable to provide the user with a card 39A, that is swiped or otherwise read electronically at the point-of-transaction to provide the equipment 39 with a user identification. The unique product identifiers 39B scanned at the point-of-transaction then can be associated with the user identification as read from the card 39A, and the resulting combination of data can be transferred to the central server 10. The data from the product identifiers 39B being scanned in this manner, can be automatically transferred to the GPI server 10 according to criteria set forth for each individual user.

Figure 5C:
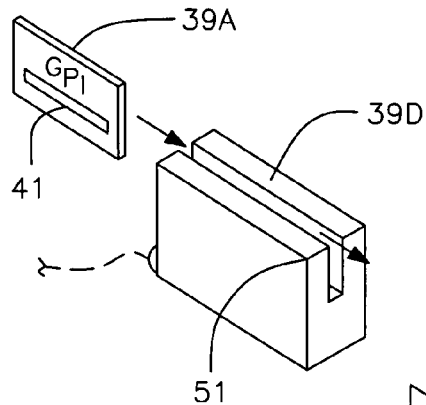
Figure 5D:
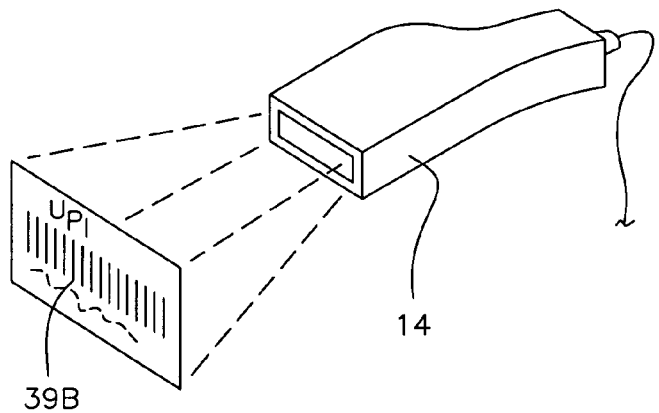
Figure 5E:
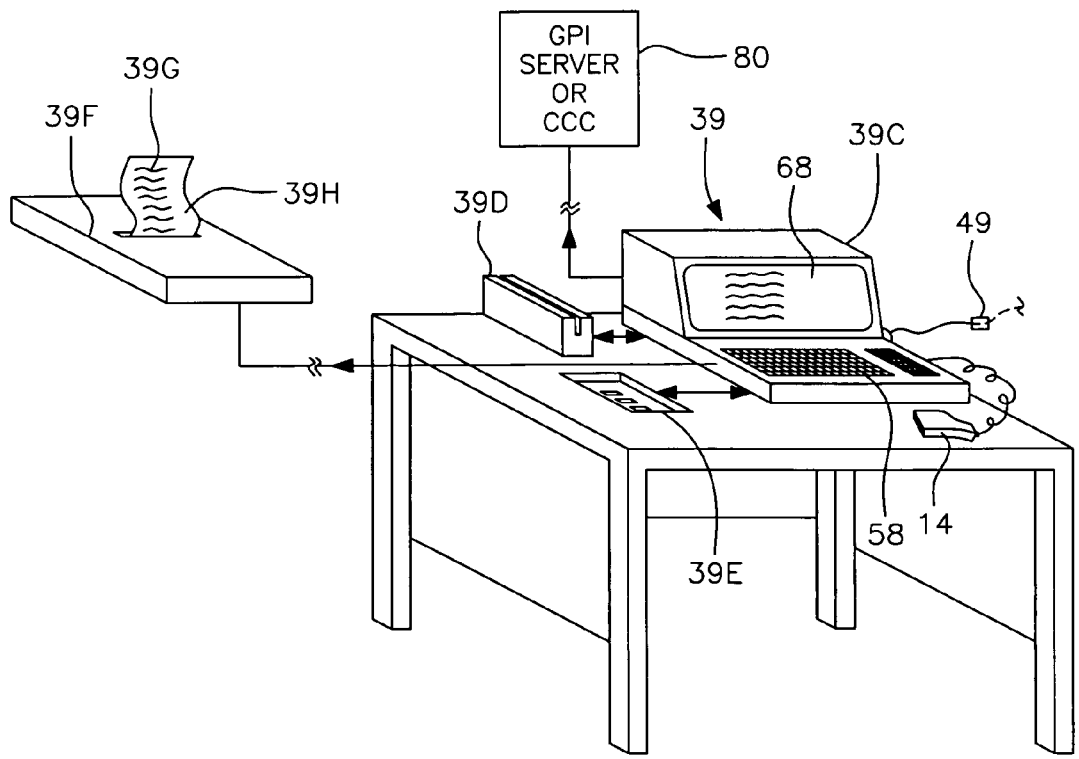

The exemplary point-of-transaction equipment 39 in FIG. 5E includes a transaction terminal 39C, a display 68, a card swipe device 39D such as a credit card reader through which a magnetically encoded GPI card that carries a user name can be read, a flat card reader or smart card slot 39E equipped to read at least the user name from the smart card 39A, a keyboard 58, and a bar code reader 14 adapted to read bar-coded product information in the product identifiers 39B. As shown in FIG. 5E, the equipment 39 at the point-of-transaction can further include data communications means 49, and a printer 39F that prints the bar codes 39G conveniently on a single piece of paper 39H, e.g., if the connection to the GPI central server 10 is not available, so that these can be scanned later at home.

FIG. 5C is an enlarged view of the card swipe device 39D. FIG. 5D is an enlarged view of the exemplary bar code reader 14. The credit card reader 39D reads binary coded data recorded magnetically along a length of a credit card. The bar code reader 14 reads optically encoded symbols. The credit card reader 39D preferably includes a slot 51. The consumer or salesperson inputs the data by swiping the credit card through the slot 51.

In the alternative embodiment of FIG. 5F, a smartcard 39A is shown at a more portable version of the point-of-transaction equipment 39. With the arrangements shown in FIGS. 5C-5F, the user can acquire a variety of UPIs 39B and then swipe the card 39A through the appropriate one of the readers 39D or 39E. The card 39A, preferably, has a memory medium 391 that stores the user identification, along with encoded data capable of opening a connection with the central server 10 (or GPI). The point-of-transaction thus has a card reader 39D, 39E communicating with the central server 10 (or GPI). When the UPI codes are scanned using a conventional bar code reader at the point-of transaction, the UPI data is automatically transferred to the GPI server 10 and stored under the username.

Referring to FIGS. 5C to 5J, the embodiment related to the use of point-of-sale for acquisition of consumer identification and product identifier for recall and warning includes point-of-transaction terminal equipment 39 and preferably remotely located Card Central Computers 80 (CCC). Data on products associated with a credit card sale or the like is collected and transmitted to said CCC 80 for storage of said product information and card holder identification, with said product information including the elements necessary for identification of a recalled product and the consumer using such product(s) according to the principles of the invention. The smart card 39A or other card such as a credit card which is used for payment, can also be used to identify the consumer as "registered" and as being qualified to use the GPI system.

The CCC 80 can include central credit card computers, computerized credit card authorization or validation centers, computerized insurance company centers, the GPI server 10, or any central computer capable of receiving and storing product identifiers and consumer identification according to the principles of the invention. The card 39A, for the purposes of this description, can include conventional credit cards, the GPI SafetyCard, smart cards, debit cards, store payment card, gas payment cards, telephone cards, insurance cards, courtesy cards, other magnetically or optically encoded cards, programming cards, CD cards, and the like. Point of sale for the purpose of the description includes any place in which a consumer can acquire a product which can cause harm to the user or be recalled. For example, but not by way of limitation, point-of-sale can include stores, malls, supermarket, pharmacies, dealerships, retailers, any business concern, and the like. Although point-of-sale is described, any point at which goods are acquired, regardless of payment for such goods, can be used and such goods covered by the GPI system, which is also referred to herein at the GPI Safety Program.

The GPI Safety Program is a free-of-charge recall and warning notification system to users of products as disclosed in the present invention. The user receives a GPI SafetyCard such as card 39A when registering with the GPI system 1 and the GPI Safety Program. One exemplary means of registering occurs when the consumer fills out a conventional credit card form. The consumer checks the GPI SafetyCard box on the form, reads the respective information on the GPI Safety Program for Recall and Warning, and signs the form authorizing collection of product identifiers. Blank credit card forms may be found in stores or such forms may be received through the mail or electronically. Similarly, the consumer may receive GPI Safety Program forms and apply for a GPI SafetyCard in the same fashion as applying for a conventional credit card. However, contrary to credit card companies that can deny issuance of a card due to poor credit history, in the case of the GPI Safety Program everybody can be accepted and each eligible consumer that enrolls free-of-charge in the Safety Program for Recall and Warning will receive a GPI SafetyCard.

The GPI SafetyCard 39A is a unique customer card issued to the customer after appropriate registration with the GPI Safety Program for Recall and Warning Notification. The GPI SafetyCard 39A has magnetically encoded data similar to a credit card, but said SafetyCard has no purchasing function. The GPI SafetyCard 39A has preferably a thin magnetic strip 41 with an identification number stored thereon. The GPI SafetyCard 39A is used to identify the consumer as registered with the GPI system 1 and GPI Safety Program. The GPI SafetyCard 39A can have identification and information data encoded in a dual face format, the front having magnetically encoded data in a strip 41 similar to credit cards, and the back having optically encoded data such as a bar-code 43. The GPI SafetyCard 39A can also be used as a key ring card, CD card, or by any other suitable means to store the registration code with the GPI Safety Program. The encoded information in the GPI SafetyCard 39A can include customer identification number (GPI Safety Program number), username, name, address, and the like. An authorized GPI credit card 39A means a credit card which the card holder is registered with the GPI Safety Program as described above. The authorized GPI credit card 39A contains in one of its tracks a few extra bits of information such as the GPI identification number or any other means to identify the consumer as "registered with GPI". At least one of the tracks of card 39A includes information on registration with GPI Safety Program and preferably the arrangement conforms to the specifications found in the American National Standard for magnetic stripe encoding and interchange message, and in accordance with standards by the American National Standards Institute. Each authorized GPI credit card 39A or the GPI SafetyCard 39A is unique in that it contains a code unique to the GPI Safety Program in its track. The GPI SafetyCard 39A can also have other information embossed on the card for further identification.

Besides using a conventional stripe credit card, the system can include a GPI SafetyCard 39A which uses only a bar code 43 or other optical symbols as means for identification of the consumer. If the consumer uses a bar coded GPI SafetyCard 39A, then the consumer presents said SafetyCard at the point-of-transaction terminal 39C which is then scanned by conventional means for bar code reading. Subsequently, products purchased with their respective product identifiers are scanned. If the consumer is registered with the GPI Safety Program and has the encoded authorization code to store product identifiers, then said product identifiers are stored in the point-of-transaction terminal 39C under said consumer identification which can include a username or Internet address. The information stored is then transmitted to the CCC 80 when connection with said central credit card computer is established, or may be stored for later transmission in accordance with the principles of the invention. It is understood that the bar coded GPI SafetyCard 39A can be scanned at the end of the transaction by the point-of-transaction terminal equipment 39. In this instance after the products purchased are scanned, then the said bar coded GPI SafetyCard 39A is scanned and the operation proceeds as described above.

The point-of-transaction terminal equipment 39 includes credit card data input devices which in the preferred embodiment include a credit card reader 39D. For the purpose of the description, the credit card reader can be considered to be a device capable of identifying the consumer as registered with the GPI Safety Program which then allows acquisition and transmission to the CCC 80 of product identifiers related to that consumer. The credit card readers 39D generate digital output signals indicative of the magnetically encoded GPI Safety Program registration information.

The point-of-transaction terminals can function as the entry point for the product identifiers and consumer identification. The point-of-transaction terminal equipment 39 can include wired or wireless cash registers, check out stations, and the like. In the case of wireless transmission, the point-of-transaction terminal 39C transmits to the CCC 80 data packets over a radio frequency communication network. When a registered consumer purchases products using an authorized GPI credit card 39A, then the product information and user identification is transmitted by conventional means to the CCC 80. Once the point-of-transaction terminal 39C actuates, automatically or manually, the transmitting means, the product identifiers scanned are then transmitted to the CCC 80, either concurrently with the transaction or later on in a batch form. Preferably, the product identifiers transmitted and stored identify products that could be recalled and that are most likely to cause harm to the consumer. This approach avoids transmission and storage of information on products that are less likely to cause harm to the consumer. In one preferred embodiment the product identifiers collected and transmitted concern drugs or medical products purchased at a pharmacy. However, any consumer acquiring any product can be protected against harm or death in accordance with the principles of the invention.

Figure 5G:
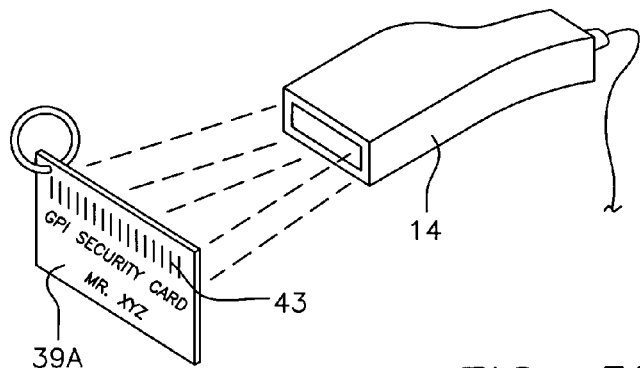
Figure 5H:
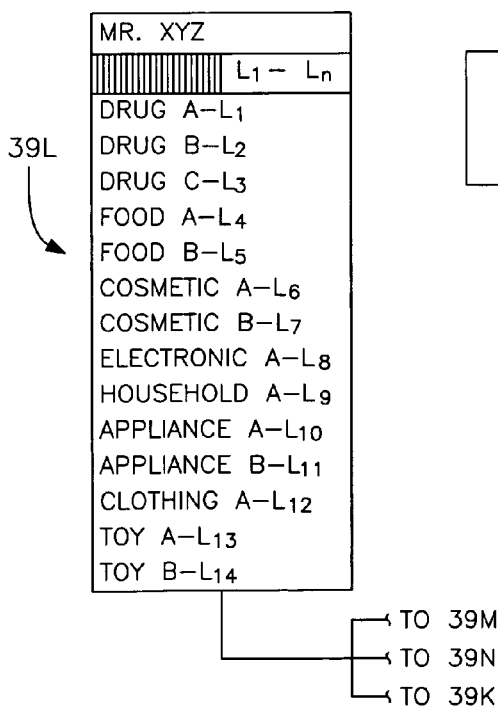
Figure 5I:
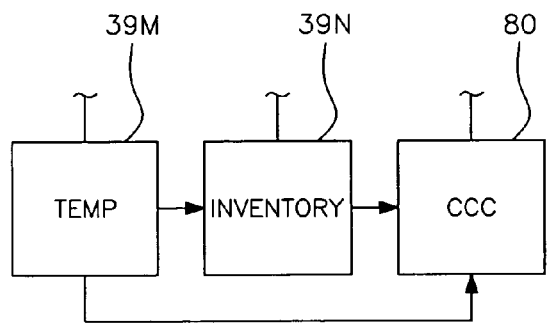
Figure 5J:
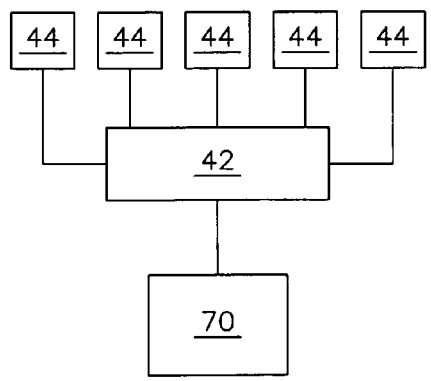
Figure 5K:
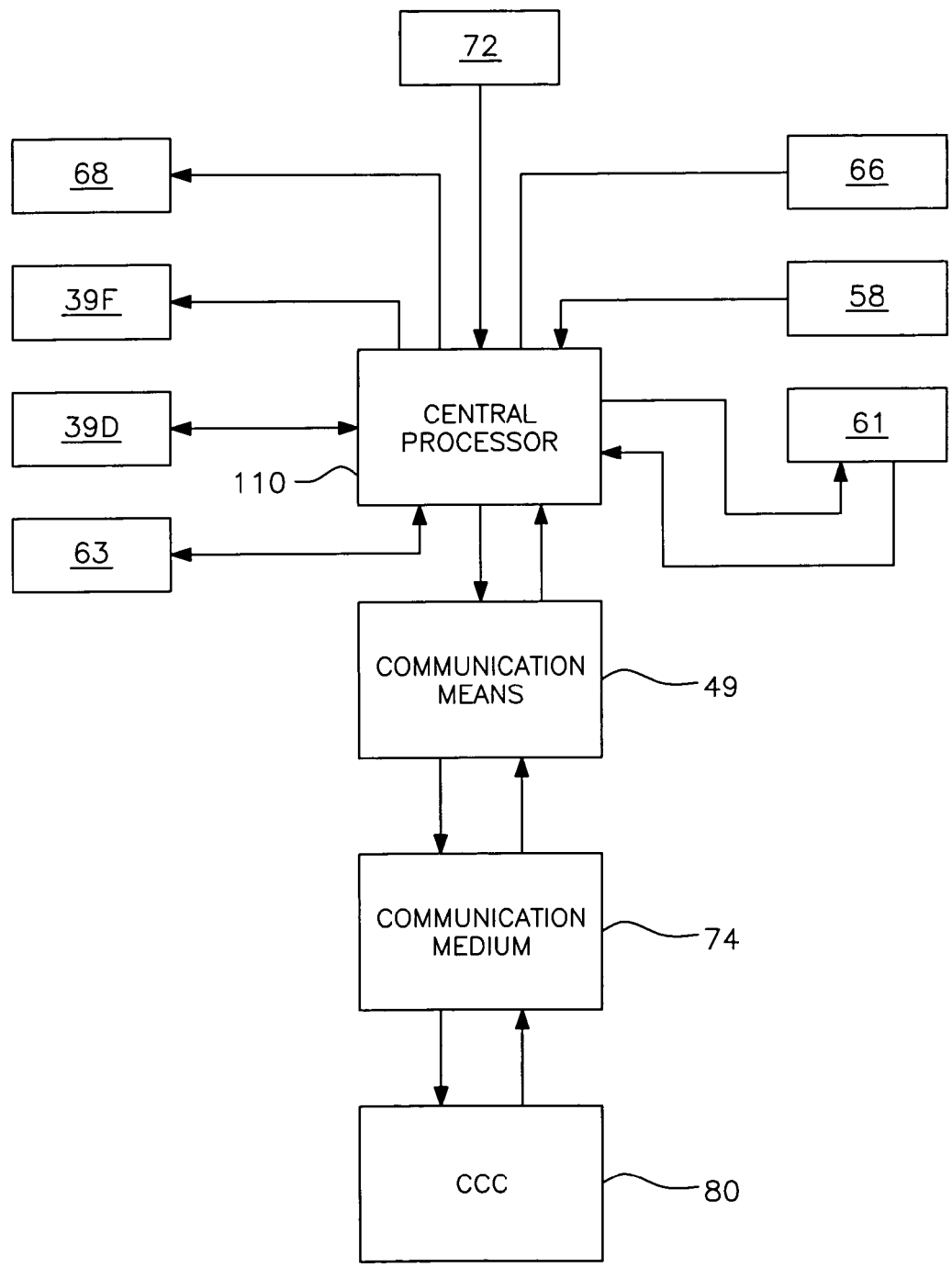
FIG. 5K is a block diagram depicting an exemplary embodiment of a point-of-transaction system.

As shown in FIG. 5K, the point-of-transaction terminal equipment 39 includes within the terminal 39C processing means 110 and memory 61 (RAM and ROM) for controlling operations of said terminal 39C with said processing means 110 interconnected to the other parts of the point-of-transaction terminal equipment 39 and being programmed so as to provide suitable control over the individual operational elements described herein. The point-of-transaction terminal equipment 39 will preferably have communication means and data communication means 49 providing for a suitable telephone line connection, cable, wireless, and the like, so as to enable communication with the CCC 80 over conventional telephone lines, the Internet, wireless, and the like. Data communication means 49 is operatively interconnected with the central processor 110 for communicating data between the central processor 110 of the point-of-transaction terminal 39C and the CCC 80. The memory 61 at the point-of-transaction terminal 39C can be used for storing product identifiers concerning products which were scanned or entered by the point-of-transaction terminal equipment 39, and includes sufficient data storage so as to enable storage of product identifiers and consumer identification. The processing means 110 at the point-of-transaction terminal 39C can be programmed to permit storage and transmission of product identifiers and consumer identification to the CCC 80, either by downloading at a later time or by transmission at the time of purchase. Various storage compartments (not shown) might be included with the point-of-transaction terminal equipment 39 to provide for storage of data (product identifiers, consumer identification, transaction documents, and the like). The data storage can be located at the point-of-transaction terminal 39C or other suitable electronic data storage at the point-of-sale.

For example, but not byway of limitation, the product identifiers are preferably encoded as optical symbols suitable for reading by a bar code reader 39D at the point-of-transaction terminal 39C. It is understood that other means to identify products being purchased or to read merchandise identification tags, whether currently available or developed in the future, can be used according to the principles of the invention. Exemplary other means to identify products at a check-out counter can include radio frequency tags, magnetic tags, other optical symbols, transponder means, and the like. It is understood that the principles of the invention apply to an environment where there is no check-out station as well as where products are not entered by a clerk nor have a bar code for merchandise identification. For instance there is no need for check-out stations when using certain radio frequency tags for merchandise identification. The radio frequency contains the information related to merchandise identification and product identifiers, with said information being linked to local store computers 39N which can further transmit the product identifiers to the CCC 80 either real time or in batch format at a later time. The method and type of payment identifies the user and links the user with the product identifiers being wirelessly transmitted to the CCC 80. When a product has various parts, such as in a machine or vehicle, which can individually pose danger to the user, said individual parts can be identified in the same fashion as has been described, or collectively identified with a unique product identifier that includes identifiers for each part of the product.

When the point-of-transaction terminal equipment 39 is connected to a CCC 80 and product purchases occur, the point-of-transaction terminal equipment 39 is used to read the identification on the card 39A and establish communications with the CCC 80. The consumer or salesperson inputs the data by swiping the credit card or GPI SafetyCard 39A through the slot 51 in the credit card reader 39D. The information provided by the credit card reader 39D to the central processor 110 about the card holder identification is transmitted to the CCC 80. Upon receipt of the information, the CCC 80 checks the identification of the card holder and advises the central processor 110 at the point-of-transaction terminal 39C as to whether this card holder is registered with the GPI system 1 and if there is proper consumer authorization to use the credit card for collection of product identifiers in accordance to the GPI Safety Program for Recall and Warning Notification. If the card holder is a registered GPI user, then the CCC 80 transmits electronically an appropriate response to the central processor 110 at the point-of-transaction terminal 39C which permits transmission of product identifiers stored at said point-of-transaction terminal 39C to said CCC 80. The product information transmitted can include product identifier, date of purchase, lot number, and other related information according to the principles herein described. If any product identifier is recognized as recalled, then the CCC 80 automatically sends the "Alert" message which may actuate the printing device 39F at the point-of-transaction causing it to print said "Alert" message. The transmission of product identifiers can occur during the transaction or, if the transaction occurs during peak or high traffic hours, the point-of-transaction terminal 39C can retain and store product identifiers in the point-of-sale memory medium such as local store computers 39N which also includes memory area 39M in the point-of-transaction terminal 39C. The point-of-transaction terminal 39C or other suitable computer system at the point-of-sale then transmits to the CCC 80 product identifiers for the various registered users collected over time. These transmissions can be scheduled to occur during off-peak access times and using a batch format. Besides linking with CCC 80, those point-of-transaction terminals 39C can be linked to other computers (not shown) through conventional telephone lines, the Internet, wireless means, or the like.

The merchant, point of sale, or any point of transaction for purchasing any product verifies with the CCC 80 whether the card holder is registered with GPI and thus whether the card holder has authorized the collection of information on products purchased. In the credit card transaction industry, there are completely computerized credit card verification services that verify credit cards in real time. The point-of-transaction terminal equipment 39 disclosed herein can electronically connect with one of these credit card verification services or any computerized center referred to herein as CCC 80, and obtain verification of registration with the GPI Safety Program before completing the second part of the transaction conventionally used in the credit card industry. The point-of-transaction terminal equipment 39 can be configured to interface with the CCC 80 to receive a code for capturing and transmitting or storing product identifiers prior to completing the remainder of the credit card purchase transaction. Alternatively, the point-of-transaction terminal equipment can be configured to interface with the CCC 80 to receive a conventional approval code for credit card purchases prior to completing the capture and transmission or storage of product identifiers. In this embodiment, while the receipt is being printed and signed by the consumer, the product identifiers are transferred to the CCC 80.

As an illustration, the preferred embodiment described can be accomplished by the point-of-transaction terminal equipment 39 calling the CCC 80 so as to obtain information on consumer registration with the GPI Safety Program. In accordance, after selection of products by a customer, the products are scanned using the point-of-transaction terminal equipment 39 and product identifiers obtained. The point-of-transaction terminal 39C places this information into memory 61 and holds this information until receiving a code from the CCC 80. The card 39A then is swiped and the point-of-transaction terminal equipment 39 forwards a stream of information as a single data transmission to the CCC 80 which includes GPI Identification number, the credit card number, expiration date, and date of purchase. The date of purchase can, for example, be used as means to identify a particular recalled product. The CCC 80 reviews its database files to determine if the card holder is registered with the GPI Safety Program. Thereafter, the CCC 80 identifies the card as registered or non-registered. If registered, the CCC sends, via the data communications link, a capture code which permits product identifiers stored at the point-of-transaction terminal 39C to be transmitted to the CCC or other data storage locally. The point-of-transaction terminal 39C then accepts the code and transmits the product identifiers to the CCC 80 or stores said product identifiers locally for later transmission. The operation then proceeds in the customary fashion for a validation of a credit card, as is well known in the credit card industry.

Alternatively, the point-of-transaction terminal equipment 39 may have interface means to locally identify whether the consumer is registered with the GPI Safety Program. Upon inputting the credit card data or the GPI SafetyCard data by swiping the card 39A, the interface electronics within the point-of-transaction terminal equipment 39 performs a local registration check to identify whether the card holder is registered with the GPI Safety Program. This local verification at the point-of-transaction includes checking for the encoded data in the credit card that identifies the consumer as registered. The GPI SafetyCard format can be confirmed against a memory check at the point-of-transaction terminal 39C.

In a further alternative embodiment, the point-of-transaction terminal equipment 39 is not used as an entry point or for transmission of product identifiers to the CCC 80, but is used as a collection site for the consumer. In this embodiment, after the products are scanned at the point-of-transaction, the consumer uses the credit card reader 39D to write information onto an information bearing stripe 41 such as the one present on the GPI SafetyCard 39A. Consumers can then download the product identifiers and transmit the data to the CCC 80 at their convenience.

A yet further alternative embodiment includes swiping the credit card 39A in the card reader 39D in the usual fashion and then entering a special registration code or command into the card reader keypad (not shown) or other point-of-transaction terminal equipment 39. In this embodiment any regular credit card, even one without a Safety Program registration encoded thereon, can be used. This manually-entered special code or command identifies the consumer as registered. At least two methods of operation may then be undergone. In a first method, data is not sent to the CCC but instead the manually-entered approval code executes the operation for storage of the product identifiers locally at the point-of-transaction. In this case, the whole operation of acquisition of product identifiers is done locally at the point-of-transaction. According to the second method, the registration data is transmitted to the CCC 80 and operations occur as previously described. The approval code serves as the consumer identification as registered with the Safety Program, with said approval code being transmitted to the CCC 80. It is also understood that alternatively the user can simply enter a code at the point-of-transaction terminal 39C without using any card 39A. The code indicates to the clerk that the user is registered with the GPI Safety Program. The clerk then can store the product identifiers for that user locally or transfer this information to the CCC 80. In this embodiment the whole operation can be done without the credit card reader 39D.

According to an exemplary operation, the consumer purchases products at a point of sale. The products are then scanned and product information is temporarily stored in the point-of-transaction terminal equipment 39. The consumer or store clerk swipes the credit card 39A in the usual fashion. After the credit card 39A is validated as registered with the GPI Safety Program locally (at the point-of-transaction terminal 39C), or preferably through a verification computer such as CCC 80, then if the consumer is registered with GPI the first message that appears indicates that the consumer is registered and that the product identifiers are captured and either transmitted to the CCC 80 or stored locally. Subsequently, the point-of-transaction terminal display 68 displays the approval code for the purchase in the usual fashion for credit card approval well known in the credit card industry. If the consumer has two cards, for instance, such as a conventional credit card and the GPI SafetyCard, the consumer first swipes his GPI SafetyCard 39A and receives the "registered" message, and then swipes his regular credit card in the conventional fashion. If the user is not using a credit card or the like and decides to pay with cash or check, the principles of the invention still apply. In this situation, after the products have been scanned in the usual fashion, the consumer swipes the GPI SafetyCard 39A in the slot 51 of the regular credit card reader 39D and waits for the response from the CCC 80 or terminal equipment 39. The card in this case is not used for purchase but only for verification of registration with GPI.

If the user is registered, the operation proceeds as previously described. The user then pays with cash in the usual fashion. As briefly mentioned, it is understood that the point-of-transaction terminal equipment 39 can identify if the user is registered and thus avoid extra transmission of data and response to/from the CCC 80. When this embodiment is used, as soon as the user swipes his/her card 39A, the point-of-transaction terminal equipment 39 identifies the user as registered and stores the product identifiers for the consumer according to the principles of the invention. In the event that the consumer has forgotten the GPI SafetyCard 39A, the consumer can manually enter the GPI identification at the credit card reader keypad, and the operation will proceed as previously described. Although it was disclosed that the card 39A was swiped after the products were scanned, it is understood that the consumer can first swipe his/her card 39A which would identify the consumer as registered. Then each product scanned is automatically stored for either transmission to the CCC 80 or further storage locally at the point of sale.

Cell phone, personal digital assistants, computers, and many other devices can have built-in credit card readers and said card readers can be used to identify the consumer as registered with the GPI Safety Program and allow acquisition and transmission to the CCC of product identifiers related to the consumer.

FIG. 5G shows schematically an exemplary bar code-based GPI SafetyCard 39A using a key ring arrangement being scanned by a bar code reader 14. FIG. 5H shows a list of products 39L with the respective product identifiers $L_1$-$L_n$ which were scanned after the GPI SafetyCard 39A was scanned. The product identifiers $L_1$-$L_n$ can then be transmitted to a temporary storage area 39M at the point-of-transaction terminal 39C, or at the inventory storage area 39N of the point-of-sale, or directly to the CCC 80. FIG. 5I shows the interconnections between the temporary storage area 39M, inventory storage area 39N at the point of sale, such as local store computers, and the CCC 80. Data can be sent from the temporary storage area 39M to the inventory storage area 39N at the point-of-sale for subsequent transmission to the CCC 80 or may be sent directly to the CCC 80. Data from the inventory storage area 39N of the point-of-sale can be sent directly to the CCC 80. The point-of-transaction terminal 39C can generate real-time data for re-stocking merchandise inventories as well as providing data to the CCC 80 for tracking recalled products.

Now referring to FIG. 5J, the system can also include a central processing station 42 connected to a plurality of point-of-transaction terminals 44 such as cash registers. All of the information on product identifiers and user identification are transferred to the central processing station 42 and said central station transmits the data to the CCC 80 real-time by modem or wirelessly, either real time or in batch format at a later time. The communications between the point of sale and the CCC 80 can include the use of secured XML tunnels. In addition, packetized or serial data can be communicated. The GPI SafetyCard 39A can have in its tracks the code to call the GPI server 10 when said GPI SafetyCard 39A is swiped through the credit card reader.

Another embodiment includes the use of a GPI SafetyCard 39A or a credit card to transmit data directly to the GPI server 10. If the user is registered, then the point-of-transaction terminal equipment 39 can assemble the data on product identifiers and username into packets and send the data wirelessly or by modem directly to the GPI server 10. In this case the GPI server 10 acts as the CCC 80 and the point-of-transaction terminal verifies GPI registration locally without sending any stream of data via interface with the credit card reader.

FIG. 5K shows a block diagram of the basic features and interconnection of the major components of exemplary point-of-transaction credit card terminal equipment 39. The point-of-transaction terminal 39C is governed by the CPU or central processor 110. The CPU 110 can be programmed to perform the functions necessary to carry out the operations according to the principles of the invention. The CPU 110 receives input from the credit card reader 39D, credit card keypad 63, keyboard 58, scanner 72, and memory means 61. The data communication means 49 is bi-directional. CPU 110 receives data transmitted to the point-of-transaction terminal 39C via communication means 49 such as a modem. CPU 110 generates a number of outputs including printer control and data signals to printer 39F, data signal to speakers 66, output data or information to the display 68 including messages such as "registered" or "non-registered", and data output for storage in memory 61. CPU 110 by its communication means 49 transmits data to the CCC 80 over communication medium 74 such as telephone lines, wireless means, Internet, or the like. Transmission of data can be implemented using EDI (Electronic Data Interchange) such as X12 or EDIFACT and communication means such as EDI VAN (value-added network)

FIGS. 5L and 5M are a flow diagram of the basic operation of the exemplary point-of-transaction terminal equipment 39 according to the present invention and serve to illustrate an exemplary basic cycle of operation thereof. As indicated in FIG. 5L when a consumer purchases goods, step 120, product identifiers are scanned or manually entered and product identifiers are obtained. At step 122 product identifiers are stored in an electronic data storage 61 at the point-of-transaction terminal 39C and displayed on screen 68. The product identifier data stored in the point-of-transaction terminal 39C represents the data obtained by entering or scanning information on the products purchased by the consumer. Next the operation determines whether the user card 39A is available, step 124. If no card is available, step 126, the operator enters card information using keypad 63 and the information is stored in memory 61, step 132. When the consumer uses a credit card 39A for payment, step 128, the operator (sales clerk) or user swipes the credit card 39A in a magnetic stripe credit card reader 39D. At step 130, credit card swiping results in the credit card reader 39D reading the card information which includes user identification and code for registration with the GPI Safety Program. At step 132, card information is stored in memory at the point-of-transaction terminal 39C and, at step 134, user identification is displayed. Step 136 then establishes connection with CCC 80 and electronically transmits a stream of encoded data to CCC 80 including GPI identification number, if present. Upon receipt the encoded data, step 138, CCC 80 checks its database to identify the consumer as registered or non-registered.

Referring to FIG. 5M, the method continues at step 140, with the point-of-transaction terminal 39 receiving code for "registered" or "non-registered". A determination is then made whether the consumer is registered or non-registered, step 142. If the user is using a GPI SafetyCard or an authorized GPI credit card with a valid start of data bit, then the user is identified as registered and the code authorizes capture and storage of product identifiers for that user. Accordingly, if the user is registered then operation executes step 144, to determine whether the transaction is occurring during peak hours. If the transaction is occurring during peak hours or high traffic, the point-of-transaction terminal 39C retains and stores product identifiers and consumer identification in the point-of-transaction data storage medium, step 146 for later transmission of the data. This alternative mode can be automatically chosen during high traffic hours at the point-of-transaction terminals, allowing efficient transmission of data during such peak hours. At the end of the day, for example, the point-of-sale terminal computers batch the record data for all consumers and submit the data to the CCC 80 for storage. In accordance, at step 148 the terminal transmits to the CCC product identifiers for the various registered users collected over time and using a batch format, and the operation ends.

If the transaction is not occurring during peak hours, step 150, the product identifiers are transmitted to and stored in the CCC 80 under the user identification which can include the username or Internet address. At step 152, the product identifier(s) are then checked against the CCC 80 database to determine whether there are any product identifiers transferred which were recalled. At step 154, the point-of-transaction terminal equipment 39 receives code "recalled" or "non-recalled". Step 156 then determines whether the product has been recalled. If no, step 158, the terminal displays "non-recalled" and the operation ends. If yes, step 160, the point-of-transaction terminal equipment 39 displays the product identifier for the recalled product and prints an "Alert" Message related to said product identifier, step 162, and ends operation.

If, at step 142, it is determined that the user is not registered, then no product identifiers are stored and the terminal displays "non-registered" at step 164, the operation ends, and the processing occurs as with conventional credit card validation for payment of goods and approval for sales. After any step in which the operation ends, then conventional processing for credit card automatically occurs and authorization for payment is conducted in the conventional fashion for credit card use for purchasing goods and obtaining approval for sales which is well known in the credit card industry. When the system for recall and notification is implemented using multiple point-of-transaction terminals 44, then a plurality of terminals with a central processor are in communication with the CCC 80. In this instance CCC 80 can be linked to all point-of-transactions terminals 44. A further alternative embodiment includes reprogramming credit card terminal equipment 39 to tag each transaction with the username prior to transmission to the CCC 80.

Figure 5N:
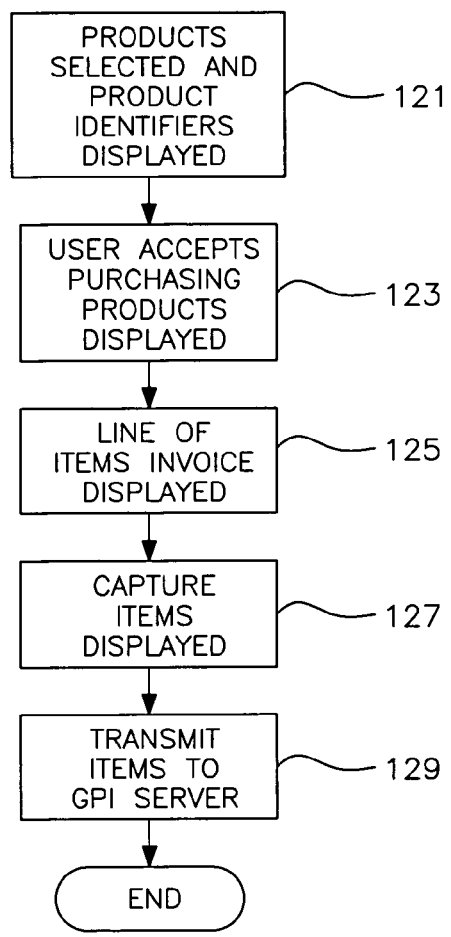

If a product is purchased over the Internet 100, then the product identifier can be automatically transferred to the GPI server 10 during the transaction. Purchases can include e-commerce, m-commerce, or any electronic acquisition of products over the Internet including e-business with acquisition of products by a business concern from another business concern. For example, a GPI agent can be downloaded to an authorized user's computer and used to capture the purchase data from the user's computer 30 and transmit to the GPI server 10 using a secured XML tunnel. A special web browser can be used to capture data related to acquisition of a product. FIG. 5N shows exemplary steps for acquisition of product identifiers over the Internet. At step 121 products (items) are selected and product identifiers appear on the screen of a computer. At step 123 the user accepts, purchasing items displayed in the line of items. Step 125 shows a bill of materials invoice or line of items invoice on the screen of a computer related to items purchased. Step 127 captures data displayed. Step 129 transmits data to GPI server 10, and the operation ends.

Figure 5P:
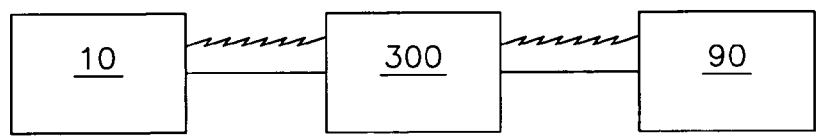
FIGS. 5P and 5Q are block diagrams of an exemplary connection between a third party server and the central server according to preferred embodiments of the present invention.
Figure 5Q:
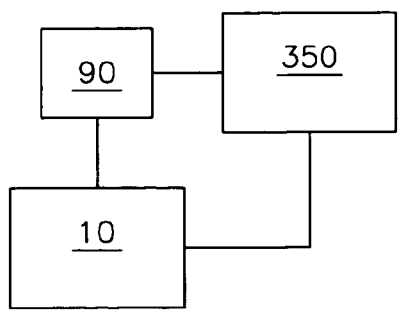

Besides using a conventional computer device for receiving and displaying alert information, the display of a cellular enabled device can be used. FIG. 5P shows an exemplary block diagram of the connection between the GPI server 10 and a communications company 300 and user 90. The GPI server 10 can be connected to communications company 300 by physical or wireless means. Likewise, communications company 300 can be connected to the user 90 by physical or wireless means. The GPI server 10 transmits the alert information to a communications company 300 which subsequently transmits the alert information to the user, for example to the screen of a cellular telephone. As shown in FIG. 5Q, user 90 may transfer over the Internet the line of items purchased to supplier's server 350. Supplier's server 350 may then transmit the line of items to the GPI server 10 over a secured XML (extensible markup language) tunnel or virtual private network. User 90 can also transfer the line of items directly to GPI server 10.

Although the point-of-transaction terminal equipment 39 can have means to select what products to choose and transfer data for, in some cases, it is more cost-effective to have information for all products or at least all products of a certain group (which were identified by proper code) sent to the GPI server 10. If all products purchased by every user 90 are scanned and the data transferred to the GPI server 10, it may create a potential data overload. It is therefore preferred that the user has the option to select the products for which information will be transferred and stored in the GPI database e.g., typically those products that are most likely to cause significant harm and increased health care costs. Although technically possible, it would be difficult if, for example, at the point-of-transaction a first user only wants one item transferred, then a second user wants one item from the D2 (over-the-counter drugs) group and four items from the C (cosmetics) group, and none from the F (food) group, and then a third user purchases items in all of the groups but wants two individual products of the Mi (Miscellaneous) group, one out of ten in the F group, two out of eight in the C group, and so forth. Under these circumstances, it would be possible but cumbersome to implement the invention in that fashion. It is therefore preferable for the user to transfer all of the identifiers or select only the products he/she is interested in receiving information about, by acquiring the UPI using the aforementioned IECLD 40 or GPI SafetyCard 39A only for the selected items.

Alternatively the user can acquire data on all the products purchased at the point-of-transaction, and store the data in the smartcard 39A. The smartcard 39A then is read in a suitable reader and information on the items selected by the user 90 is transferred to the GPI central server 10 for storage. Naturally, the user 90 during registration or at any time thereafter has the option to select and/or block the information to be sent about harmful, beneficial, or recalled products at the user's discretion. For example, the user 90 may only want to know about recalled products, or only recalled drugs and harmful effects of drugs, or recalls and beneficial information on cosmetics, or recalled baby/toy products and recalled drugs and cosmetics, and so on. Thus, even if all UPIs are transferred, the system 1 can be tailored to the individual need of each user so that only the data that is meaningful to that user is transferred.

Although the preferred embodiment concerns the electronic transfer of information, the invention can be carried out using conventional communication means as previously mentioned. In those alternative illustrative embodiments, the user 90 can utilize a conventional telephone line to communicate with the central server 10 (or GPI) which can direct the user to a human attendant who then registers the user 90 and collects the personal information, the UPI data, and any biological variables data if applicable. The attendant then converts the data into binary elements and transmits and stores the data in the GPI central server 10 in the manner previously described, or alternatively, digitized and faxed information could be acquired and processed in a similar manner. Once the user 90 is registered, the whole entering of data can be done automatically without human interference since the data consists of numbers for either the UPIs or the biological variables. This consequently can be performed using a telephone keypad and conventional Interactive Voice Response (IVR) Unit. The user 90 then can contact the GPI central server 10 to receive feedback information on the products being used. The GPI central server 10 can convert text into audio with standard electronic voice synthesizers.

Although less preferable, it is intended that the current invention also can be carried out using printed medium which is converted into binary elements and used in accordance with the principles of the invention previously described. Although the preferred way to carry out the invention involves data transfer in electronic mail format, it is understood that other electronic data transfers including automatic transfer to a computer, without the user necessarily having to open and read an e-mail, can be used. For instance, if a company is registered with the GPI system 1, the information can be transmitted using electronic data transfer and interface with the alert information appearing directly on the computer screen of a designated human attendant. For users who cannot receive electronic transmissions or have no connection with the Internet, an automated print out sheet with the information can be made and mailed to the user by conventional means to the user's regular mailing address, thereby allowing potentially life-saving information about recalled products to reach any user. In addition, a recall message and information can be sent to a telephone device and displayed on the screen of said telephone device. Although printed means and conventional telephone means are not the preferred way, the critical information about recalled products can be made available to anyone regardless of their electronic capabilities. As mentioned above, any user 90 of a product can register freely using the PCT stations 156 and transfer product identifiers. Such users 90 are subsequently informed by mail or phone messaging when they do not have Internet capabilities. When using electronic means, the preferred output means includes a computer screen, whether portable, conventional, or other as previously described, but for elderly patients a more friendly interface such as a television screen is a desirable alternative way carrying out the invention. In this regard, the IECLD 40, besides its regular functions described, can work as the remote control for the television and/or VCR.

Figure 6:
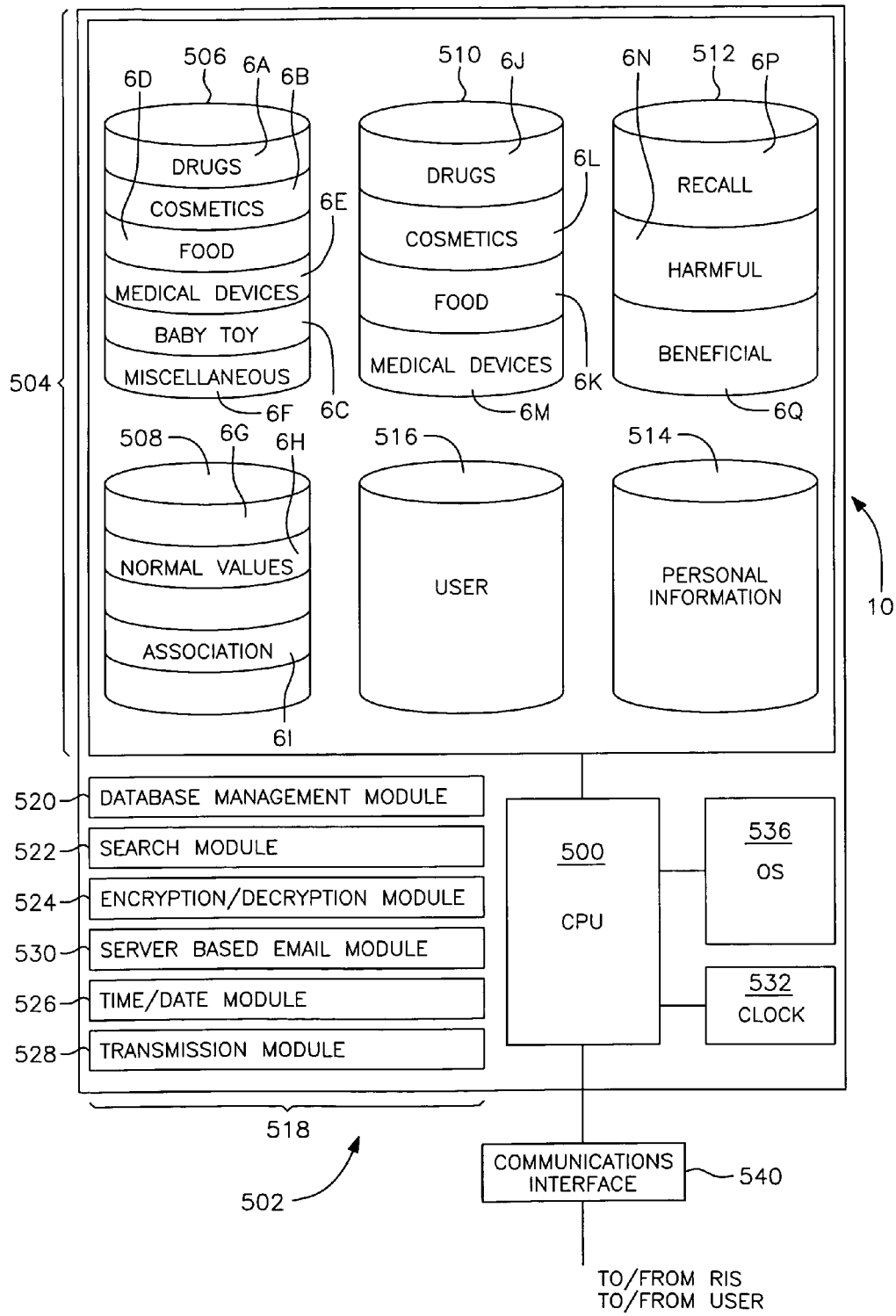
FIG. 6 is a block diagram depicting an exemplary embodiment of a central server according to the present invention.

With reference to FIG. 6, a preferred embodiment of the central server 10 will now be described. The exemplary central server 10 includes a CPU 500 and an exemplary memory medium 502 with an exemplary memory arrangement 504. The exemplary memory arrangement 504 includes databases such as a product database 506, a biological variables database 508, an interaction database 510, an alert database 512, a personal information database 514, and the user's product usage database 516, as well as conventional modules 518. The modules 518 may include database management modules 520, search modules 522, encryption/decryption modules 524, time/date modules 526, transmission modules 528, and e-mail modules 530 along with secure server-based electronic mail application. The exemplary central server 10 also includes a clock 532, operating systems 536, RAM, ROM and other typical server 10 applications and hardware well known in the art. Although the GPI central server 10 preferably searches using ASCII character and numerical matching and comparison, it is understood that graphics, multimedia, sound, and the like can be used according to the style of database and computer applications utilized.

Still in reference to FIG. 6, the CPU 500 interfaces with the operating system 536 which may include single or multiple high-speed processors operating in parallel or otherwise executing applications stored in the memory devices, RAM and ROM, to carry out the necessary functions illustrated below according to the principles of the invention. The CPU 500 receives UPIs and biological variables from the user 90 and information on UPIs from the RIS 60, preferably via the Internet 100 through a communications interface 540, and stores the data from the user 90 in the product database 506, user's product usage database 516, biological variables database 508, and personal information database 514. The CPU 500 stores the information from the RIS 60 on UPIs and/or biological variables in the alert database 512, and stores information on interactions in the interaction database 510.

FIG. 6 also depicts an exemplary memory arrangement in which the product database 506 includes a drug database in memory area 6A, a cosmetics database in memory area 6B, a baby/toy products database in memory area 6C, a food products database in memory area 6D, a medical device products database in memory area 6E, and a miscellaneous products database in memory area 6F. The product database 506 includes the UPI, preferably the bar code numbers, associated with the usernames according to a preferred embodiment of the invention. The product database 506 maintains a list of all products stored according to the product category, and contains records of each individual product with all of its users according to the product category. Thus, each UPI may be associated with a plurality of users. More specifically, the product database 506 maintains data on products according to the categories including the drug database which contains the UPI for the drug identity transferred by the user and all corresponding usernames of people using that drug. The cosmetic database contains the UPI for all cosmetics and associated users of each individual cosmetic UPI. To further illustrate, the food database contains the UPI for food products and corresponding usernames associated with each food product, the medical devices database contains the UPI for the medical devices with corresponding usernames, the baby/toy database contains the UPI for the infant products and toys with corresponding usernames, and the miscellaneous products database contains the UPI for miscellaneous products and corresponding usernames.

The user's product usage database 516 includes the name of the user 90 and associated UPIs for the user 90, and maintains a list of all usernames stored with all of the UPIs associated with each individual user 90.

The biological variables database 508 includes the values acquired by the various HMDs 50, which values are located in memory area 6G. The standard normal values for biological variables are located in area 6H which allows values transmitted by the user to be correlated with normal standard values. Memory area 6I has the pathological diagnosis associated with abnormal biological variables and is called the disease association area. The disease association area 6I contains an expert system concerning the diagnosis associated with the abnormal biological variable, for instance, increased eye pressure indicating glaucoma, elevated blood sugar indicating diabetes, and so on.

The product interaction database 510 has updateable fields including the most commonly known interaction between products (UPI) and biological variables. The data on interaction of drugs with biological variables and other products (UPI for the product) is stored in memory area 6J, the interaction of drugs with food is stored in memory area 6K, the interaction of drugs with cosmetics is stored in area 6L, and the interaction of drugs with medical devices is stored in memory area 6M.

An example of the interdependence of these databases is as follows. If, for example, a user 90 performs an eye pressure measurement (to acquire a biological variable) at home with an HMD 50, as described by Abreu in the aforementioned patent, and the eye pressure levels are transmitted to the central server 10 (or GPI), then the CPU 500 in the central server 10 receives the biological variables (eye pressure) and stores the value in the biological variables database area 6G which is then evaluated against the normal values area 6H. Since the values, for example, are high, which is indicative of glaucoma, the CPU 500 searches the disease association database 6I for the criteria of eye pressure increase, in order to identify the disease associated with the transferred biological variable. In a more descriptive form, if the eye pressure is above normal limits (e.g., if it is above 30 in the right eye, indicating that the patient is at risk for glaucoma and blindness), then the system naturally informs the user about the risk of blindness due to glaucoma. In addition, the system then matches that information "increased eye pressure or glaucoma" against the various products (UPI) stored by the user at risk of glaucoma and checks whether any of the products in his/her database is contraindicated for someone with glaucoma. If any record representative of any UPI is associated with the criteria glaucoma, a match is found and the information transmitted back to the users informing him/her that the product for which information was transferred is contraindicated for patients with increased eye pressure (or glaucoma).

As a second example, the user has stored under COSMETICS 6B a code for a steroid based-shampoo, then the system identifies the matching steroid product with a "contraindication glaucoma" as harmful and automatically sends the appropriate alert to the user according to the principles of the invention. If, for instance, the user buys a moisturizer skin lotion (UPI #2111211314) and later on, for instance, the FDA 130 sends a warning about a moisturizer skin lotion (UPI #2111211314) which contains unlabeled amounts of steroids, the data for "steroids" is checked against the biological variables database 508 which contains the usernames associated with the disease, in this case increased eye pressure data which is labeled as glaucoma. The system then identifies the match "steroid lotion-glaucoma" as harmful and automatically alerts all the users of UPI #2111211314 and who also have increased eye pressure indicating that they are at high risk of blindness should they use the skin lotion. Since the information was received from the FDA 130 and there is risk of injury/illness, all of the users 90 of the product identified by the subject UPI will be informed about the newly found information on steroids present in the skin lotion, thereby allowing all of the buyers of the skin lotion to know the risks related to continued use of the skin lotion. The user with increased eye pressure is informed about the dangerous situation even though he may not be aware of the fact that steroids can lead to blindness when the user exhibits abnormal eye pressure. The invention thus gives the information to the user even without the user knowing the name or consequences of the ingredients or warnings on the label. Furthermore, even if the user knew that steroids could lead to blindness in someone with glaucoma, without the invention, the user would have to search through thousands of daily warnings and then by chance identify the skin lotion he/she bought as containing unlabeled amounts of steroids.

Another example will further clarify and demonstrate the urgent need for the invention. If the user for instance is prescribed a common drug for high blood pressure such as verapamil (a calcium channel blocker), then information identifying the drug is stored under the username of that user 90. If the same user 90 then buys and transfers to the GPI central server 10 under his username the code for grapefruit juice, the identifier for grapefruit is entered and the system 1 identifies the harmful match verapamil-grapefruit juice and alerts the user about the dangerous interaction. "A bioflavinoid present in grapefruit juice interacts and inhibits the P-450 enzymatic pathway in the liver. The decreased first-pass P-450 metabolism increases the concentration of verapamil with the consequent significant increased pharmacological effect of the drug." The increased effect of verapamil caused by grapefruit juice can lead to severe hypotension and even a fatal event depending on the dose and patient susceptibility, in addition to a risk of car accidents due to impaired reflexes or fainting at the wheel, as a result of decreased blood pressure caused by the harmful combination verapamil-grapefruit juice. As soon as the harmful interaction is identified, a warning message is sent to inform the user to avoid grapefruit juice when taking verapamil. If the user had transferred information on orange juice, the system would not identify any harmful interaction between the orange juice and verapamil, and no warning would be sent. The invention thus optimizes electronic transmission creating a cost- and time-efficient system in which only relevant information is sent to the user. The user does not need to know the meaning of the abnormal biological variable, nor does he/she need to be aware of the interaction between products for which identifying information has been stored. Furthermore, the user does not need to know that a product being used can fatally or harmfully interact with another product being used. The system of the invention provides all of this life-saving and cost-saving information automatically, regardless of the knowledge of the user in regard to the products being used. If the user then purchases and transfers information on a certain product, even if the user does not know the ingredients of the product, the system of the invention will alert the user about potential interactions between such products and other products for which there is identifying information stored in the product database. In addition the system 1 informs about interaction between that product and biological variables stored in the biological variables database and/or the product and individual sensitivity, such as allergy with any product interactions newly received from RIS 60 and stored in the interaction database according to product category and the principles of the invention.

FIG. 6 also shows the alert database 512 which includes data on harmful effects of products and harmful interactions stored in memory area 6N, data on beneficial effects of products and beneficial interactions stored in memory area 6Q, and recall data stored in memory area 6P. Whenever any of the RIS 60 transfer a product alert, the CPU 500 of the GPI central server 10 receives the UPI information and stores the UPI information in the alert database 512 according to the type of effect (B=beneficial, H=harmful, or R=recall). The alert database 512 tracks and includes all of the data warning, product information and recall information on products (UPI) received/acquired from the various RIS 60 ranked according to the level of importance/severity (e.g., 1 to 5) and according to the type of event (B, H or R).

The data on products (UPI) preferably is checked against the product database 506. If the search process identifies codes (UPI) or names stored in the products database that match the code (UPI) or name of the products received from the RIS 60, then the usernames under which the product codes (UPI) are identified are used to effect a subsequent electronic transfer of the information/message on the products to the username or IP address.

The CPU 500 preferably is programmed to automatically search the product database 506 and use the UPI number as the search criteria. The CPU 500 thus searches the product database to identify the same UPI number and the users associated with that UPI number. The users are then identified and the alert information on such a UPI is transmitted back to all of the users of the product (UPI).

The data on products transferred from the RIS 60 also is checked against the biological variables database 508 and interaction database 510 of the users. If the search process identifies biological variables that match the UPI information transmitted, then the usernames under which the biological variables are stored are used to effect a transfer of the information/message to that username. For instance, if user Mr.ABC@IBM.com has transferred liver enzyme values using a HMD 50 for non-invasive blood analysis and those values are elevated and consistent with liver disease, then the disease association database 6I for the user indicates "liver disease". When the RIS 60 transfers information about the drug Rezulin associated with a "contraindication liver disease" record, then the CPU 500 stores the data in the harmful alert database 6N, and then searches the biological variables database 508 and in this case finds a match for the criteria. A warning therefore is sent by the CPU 500 to Mr.ABC@IBM.com about the drug Rezulin being contraindicated to patients with liver disease. In this case, the user Mr.ABC was not using the drug Rezulin, and further search did not identify the UPI for Rezulin associated with his username. In this manner, the GPI system 1 acts in a preventive manner by informing the user on what to avoid, and thus helping to preserve the user's health and simultaneously saving money for the user, who did not waste his money buying an expensive drug which ultimately could harm him.

The personal information database 514 includes fields such as all the data submitted by the user to the GPI server 10 during the registration process including a unique username with its Internet address and code and/or password. The user may send his/her name, but it is more desirable to have the user remain anonymous and, for example, just use an e-mail address with a pseudonym. Each new registered user can also be assigned a unique user identification number. While the invention can be carried out with any address and preferably is carried out with only the electronic e-mail address, optimal use of the features of the invention may require some additional information such as age, biometric elements, demographic information, address, medical information, personal information, family history, insurance information, primary care doctor, preferred and/or nearest pharmacy, preferred laboratory, and the like. If the user includes allergies to a certain product in his database, the product name and/or other identifier are then used during searching. If the patient is allergic to peanuts, for example, but does not have UPI information related to a product with an undisclosed amount of peanuts, then any time a new UPI is sent by the user to the GPI central server 10, that transferred UPI is checked against the identifier stored in the allergy field (peanuts), and if there is a match, (any peanut protein present) then a warning is sent to the user who transferred the UPI. If the user, on the other hand, has already stored in the product database a certain UPI (e.g., 1212131), then if the GPI central server 10 receives information from the RIS 60 that a certain product UPI 1212131 was found to have undisclosed amounts of peanuts, then the search criteria "UPI 1212131 peanuts" is checked against the allergy field which identifies the user as allergic to peanuts. The CPU 500 searches the product database 506 and finds in the food memory area 6D a match for the criteria. This indicates that the user is both allergic to contents of the UPI transmitted by the RIS 60 and also has stored information indicating that the user is potentially consuming food contaminated with peanuts. The CPU 500 then can transmit the information back to all users of the UPI 1212131 as a warning for products containing undisclosed amounts of peanuts using the regular electronic information conventionally done for the non-peanut allergic users. However, for the users identified as allergic to peanuts and also using the product with a UPI indicating that it contains peanuts, then an urgent alert is transmitted by autodialing, paging, etc, in addition to the electronic messages, since consumption of peanuts by such an allergic user can lead to a fatal event.

In another example, the user Mrs.LK20@hotmail.com transfers a UPI 0911232425 related to a baby-toy product to the GPI central server 10, in this case the UPI for a certain portable crib. The CPU 500 of the GPI central server 10 is programmed to receive and store that UPI 0911232425 with the respective username Mrs.LK20@hotmail.com in the baby-toy database 6C. The CPU 500 then searches the alert database 512 for any information related to that UPI. In this example, at the time of searching, there was no match for the UPI in the alert database 512. If a few months later, recall information for UPI 0911232425 is transferred from the CPSC 132 to the GPI central server 10, then the recall information will be stored by the CPU 500 in the recall area 6P of the alert database 512. Any UPI stored in the alert database 512 is automatically compared against the UPI information stored in the user's product usage database 506, and if there is a match, the information associated with the UPI is transmitted back to the users. In this example, Mrs.LK20, although completely unaware of using a deadly crib, receives the information immediately upon the CPSC determination that the crib is unsafe or may have killed a child, as usually occurs when the product first causes injury and then is recalled. In addition to Mrs.LK20@hotmail.com, all of the other users of the deadly crib are informed about the fatal danger posed by the product. The manufacturer of the crib then can reach all of the users in the most inexpensive way. The company also minimizes any consequences or financial disaster that it might have experienced had it publicly announced the recall. The cost savings become more readily apparent when one considers the company's virtual obligation, without the system 1, to continue advertising the "wrong-doing" until every recalled crib is identified.

The present invention also saves time and effort that might otherwise have been wasted on mass advertising on a regular basis. Additional savings are realized as a result of the consequent reduction in the risk of product liability suits and settlements, and the savings that are realized by not having to pay health care and/or disability expenses related to the harm caused by the product. This also obviates the related risk of going out of business under the resulting financial strain, and the commercial embarrassment of having to publicize the dangers of the product. More importantly, however, thousands of innocent lives can be saved. Government spending also is reduced because any related government-funded health care or disability benefits are averted. The economy of the nation also benefits by saving the companies from financial disaster or from going out of business, thus preserving jobs for its people. As can be seen, the present invention is extremely useful and vital not only for the user, but also the manufacturer and the government, and it is quite inexpensively implemented, creating the reliable wide spread recall and information coverage system urgently needed.

Considering the crib as an example, the recalled product is a level 4 (meaning a fatal event can occur with the use of the product according to the information from the CPSC). MrsLK20@hotmail.com is then informed by not only electronic means but also using conventional communication techniques such as autodialing, paging, and the like. This is done to maximize the likelihood that the critical information about the deadly crib will reach the intended recipient. The system, as will be further described, may even prevent the death of the first child, by informing the user about the risk before the government even issues a recall.

In another embodiment, the GPI system 1 uses a PCT arrangement 156, which is a Public Computer Terminal, with bar code reading capabilities and connected to the GPI central server 10. The PCTs 156 are located in public places, such as post-offices, malls, grocery-stores, and the like. Thus, any product user, even those who do not have a computer and/or are not a registered user, can send information to the GPI central server 10 concerning the harmful effects of products being used. The user, for example, may enter only the name of the product or the establishment delivering the product, but preferably the UPI, which can be manually entered or scanned with a bar code reader. The user then fills out a simple standard form with type of effect B or H, and selects from a menu of types of injuries/illnesses caused by the product, types of problems according to product and the frequency of occurrence. The information then is transmitted to the central server 10 (or GPI). If a significant number of users report a harmful effect related to a certain product or establishment, the information is transmitted to the FDA 130, CPSC 132 or any other appropriate RIS computer 60. Anyone with access to the Internet could transfer product warning information by logging onto the GPI web site and by filling out the product warning form. In the case of the deadly crib, if a certain number of users send warnings identifying the crib as injuring a child, even if slightly, or as having unsafe features as observed by the user, the information could be transferred to all of the users of the crib as a GPI alert, not an RIS alert, allowing the user to better evaluate the product and, if applicable, take the necessary precautions in order to keep the product from causing injury.

An alternative exemplary embodiment can include a personal acquired medical database that includes beneficial, harmful, recall, and interaction data acquired that relates to the particular medical status of the user according to medical information and biological variables stored as well as any relevant past medical or allergy history. If, for instance, the user transfers blood glucose levels using appropriate devices which indicate that this patient has diabetes, then all products stored in the product database 506 for that user, and the biological variables stored in the biological variables database 508 for that user, as well as all beneficial, harmful, recall, and interaction data for that user that meet the criteria "diabetes" are also stored in the personal acquired medical database under "diabetes". Thus, if the user wants to know what product data, biological variables data, recall data, interaction data, harmful effects data, and beneficial effects data relates to the user's diabetes, the user can easily access the information which is stored under "diabetes" in the personal acquired medical information database. The user can also store any other personal medical information or acquired medical information in the personal acquired medical information database.

The product database 506 also can maintain for each UPI a plurality of document records, textual or multimedia, that are representative of the UPI stored. For example, the UPI for a certain drug has associated document records concerning the indications, known side-effects, known drug interactions, description, chemical formula, and the like, stored in the database for that drug UPI with the information being continuously updated by a remote manufacturer computer 148.

It is understood that the transfer of data/information can be performed using conventional encrypted transmission in order to increase the level of confidentiality of the information. The GPI central server 10 uses the communications interface 540 to communicate with the user and/or RIS 60 with interfaces that support standard or high-speed connections with the Internet. The GPI central server 10 transfers data to/from the user 90 and to/from the RIS 60 including exchanges of messages with attachments such as files, video, graphics and audio which are communicated in a variety of ways, including a network interface electronically connected with commercial on-line providers, or configured as a web site, electronic mailing address, World Wide Web interface, direct link, and the like along with other conventional physically wired and wireless communications and for the purpose of completeness conventional means such as facsimile, postal mail, voice means, pagers, and the like. Preferably, however, the electronic means are provided via a communications interface that transfers data over the Internet. It also is intended that conventional authentication means can be used in order to provide the authorized accessing and transferring of data. It also is understood that the database above described is only an illustrative system, and a variety of modifications, changes in database and field combinations can be made by those skilled in the art without departing from the scope or principle of the invention.

In accordance with an exemplary embodiment of the present invention, after the user acquires the UPI for a drug the UPI is electronically transmitted to the GPI server 10 and then to the product database 506 and drug memory area 6A. For instance drugs "D1", "D2" and "D3" are stored in the product database in the drug memory area 6A with their respective indications for the users of such drugs. For example UPI 4546478 corresponds to D1 and is associated with Mr.ABC@mailcity.com, Mrs.DEF@whitehouse.gov and Dr.FGH@navy.mil. When a medical device "M1" is used, the individual unique product identifier UPI141618486 and respective user 15,976 is stored in the product database in the medical device memory area 6E. In this case, as an example, the username or IP address is assigned a unique user number. When the user Mrs.Ethel@gpi.co.uk transfers information regarding two different types of cosmetics "C5" and "C10", the user Mrs.Ethel@gpi.co.uk appears associated with both "C5" and "C10" and this relationship is stored in the product database 506 in the cosmetic memory area 6B. When a baby product "B1" is used, the UPI code number is stored in the product database 506 in the baby-toy memory area 6C, and when a food product "F32" is used its individual identification number is stored in the product database 506 in the food memory area 6D, and so forth with its associated usernames and representative records.

The GPI system 1 can be used in a variety of environments, but since drugs, medical devices, cosmetics, toy/baby products, and food define the main sources of harmful products and recalled products, those are the ones referred to in this part of the description. This invention, of course, is not limited to such products, especially since virtually any product could be recalled or considered harmful, in which case, there would be a need to identify the affected users and locate and alert them as well, in accordance with the principles of the present invention.

Besides the common products described above, a variety of biological data or biological states or biological functions such as temperature, weight, visual acuity, blood pressure, eye pressure, blood glucose level, chemical analytes in the blood, DNA fragments, as described in patents by Abreu and the like, can be used as biological variables. Common products or medical devices which alter these biological states and biological variables also can be used according to the invention such as the implantation in living tissue of chemical substances, devices, artificial prosthesis, radio active seeds, and the like; the external placement on living tissue of devices such as hearing aids; the interaction of chemical compounds with living tissue such as cleaning and sterilizing substances; the manipulation or modification of living tissue such as with invasive surgical procedures and the like. It is also understood that any prosthesis, chemical substances, devices or the like will have appropriate identification number and codes which can be optically encoded for identification with subsequent acquisition by the IECLD 40 or GPI card 39A and then the data on a particular medical device transmitted to the GPI server 10 for storage in the database.

For example, if a certain type of prosthesis is later found to come from a lot which is contaminated, the patient would be sent a warning and instructions on how to proceed. The same would apply to defective material which could be found in intraocular lenses, defective circuits found in pacemakers, chemical substances implanted in the body such as altered silicone which was found to cause cancer, defective collagen implants used in cosmetic surgery which caused severe inflammation due to the material in that particular lot, defective sutures or staples used inside the body or outside the body which caused severe granulomatous reactions, stents used in vascular surgery that came from a particular lot and then later were found to easily crack and leak, defective X-rays and imaging devices which were used by a variety of patients and later found to have exposed the patients to a harmful amount of radiation, whitening gel to be placed on teeth while sleeping coming from a tampered lot which were found to cause severe allergic reactions and to be caustic, cream for the treatment of skin disorders which were later found to cause permanent skin thickening and potential severe skin reactions, cosmetics which were later found to come from a contaminated lot and caused corneal ulcer and blindness, color additives which were later found to cause severe neurotoxic reactions, certain food from a certain lot which was found to be contaminated with *E. coli* and caused severe disease and even death, ineffective vaccines which were later found to come from a tampered lot, and the like. It is understood that any products that have a particular identification number could be optically encoded, tracked, identified and located using the GPI system 1 with the individual user 90 being appropriately informed and instructed in regard to potential health hazards related to such product.

All of the biological variables and/or products (UPI) transferred by the user 90 to the GPI server 10 are stored in the GPI database 504 under the code or username for that user, allowing the information in regards to that user to be continuously updated by the user 90. If the user 90 deletes, for instance, drug Y from the list of drugs being used, that information is sent to the GPI server 10 which then will delete drug Y from the GPI database for the user 90, allowing the GPI server 10 to continuously update the GPI database, keeping track of new information which is added and old information that is deleted. For example, in another embodiment when a manufacturer of a pharmaceutical product or the FDA sends a warning to the GPI server 10 about a product P, all users of product P stored in the GPI database will receive the warning. When the user of product P logs into the GPI web site, the user receives automatically the stored messages in the GPI database on product P, or alternatively when the user of product P logs in the GPI website, the user is informed that there is a warning about product P stored in the GPI database 504 which should be retrieved or there is an e-mail alert on product P that should be retrieved. In accordance, a duplex communication channel can be created in which individuals using product P automatically receive information related to product P from the GPI server 10 and the individual using product P can receive automatically or interrogate the GPI server 10 in regards to any information which directly or indirectly relates to product P and that could have an effect on the health status of that individual. In this embodiment, the GPI System is used as a locator and information source which allows immediate delivery of information to individuals using product P. In case that post-market surveillance identifies a new side effect or new drug interaction, then all patients using drug product P, for example, automatically receive information related to the update. The electronic automated location and information system of the present invention allows millions of users at risk of life-threatening event related to the unintended harmful effect of drugs and other products, to simultaneously receive life-saving information using a timely, private, individual, confidential, orderly, precise, continuous, reliable, low-cost and cost-efficient system.

In another exemplary embodiment shown in FIGS. 5C-5F, the IECLD 40 is brought by the user to the point-of-prescription of the product or point-of-care or point-of-sale or point-of-receipt or point-of-transaction. For example, the user 90 will bring his/her IECLD 40 to the pharmacy where the user is purchasing a variety of products including drugs. The user 90 may decide that he/she only wants to acquire information on the drugs and cosmetics being purchased, but not on some consumable items as candy, milk, and other readily consumable food items. The invention thus allows the user to decide which products the user would be interested in receiving information and/or recall and/or alert information concerning. The user 90 can simply scan only the products of his/her interest to be stored in the GPI server 10. On the other hand, if all of the products purchased are being scanned at the point-of-sale by a clerk or at the point-of-care by a health provider, then applications can be used to select only relevant products to be transferred and/or stored in the GPI server 10. This alternative manual selection or automatic selection of products to be stored is useful in avoiding the storage of excess or useless data.

In an example for acquiring identification about a prescription drug for appetite control, the user brings his/her IECLD 40 to the pharmacy. The pharmacy has a table with various UPI bar codes for each drug, or preferably each package will have the newly created UPI identifier bar code imprinted or the pharmacist can manually type in and send the drug identifier code to the central server 10. The user enters his/her ID and password, and then the unique barcode for the drug is read and the data is stored and displayed in the display of the IECLD 40. Alternatively, the user may access the GPI web site and enter the bar code number directly to the GPI server 10 and database under the user's name. Alternatively the user may provide his/her code and enter his/her password and the data sent directly from the point-of-prescription (pharmacy) to the GPI server 10 station to be stored under the username. Alternatively, during a purchasing transaction and payment of goods, the bar code is scanned and the data is directly transmitted from the point-of-sale to the GPI server 10 station via conventional or electronic communication lines. Alternatively, the pharmacy (point-of-transaction) sends the UPI directly to the GPI server 10 when the patient fills a prescription regardless of the patient having a portable unit 40 as the IECLD 40. In this instance the user has all of the information stored in the server 10 with information directly transmitted from the pharmacy. In countries like Japan in which the doctor may act as a pharmacy and provide the drug directly to the patient, the doctor's assistant can enter the new data into the portable IECLD 40, and the information is transferred to the GPI server 10 at the point-of-care, in this case the doctor's office or alternatively the hospital. The IECLD 40 can be interfaced with a printer in the doctor's office and an updated drug regimen printed and given to the patient, and/or a prescription slip may be printed if needed.

In another embodiment the user may carry a smartcard 39A which can acquire and store the product identification data for subsequent transmission of the product information to the main GPI server 10. In another alternative embodiment the users carries their smartcard consisting of a GPI smartcard 39A which contains information on the user which identifies the user, and for instance when the user purchases a product such as drugs, at the point-of-sale during check-out at the cashier, the GPI smartcard 39A is entered or scanned, then products are scanned and the data on the drugs (or any selected products) being purchased is automatically transmitted from the point-of-sale to the GPI server 10 and stored under the username for the GPI smartcard 39A. Alternatively the GPI smartcard 39A is placed on a receptacle at the point-of-transaction for acquisition of the unique product identifier codes with the user being able then to later select what products or group of products stored in the smartcard 39A will be transferred to the GPI server 10 or CCC 80 for storage, thus allowing the user to later select, and then transfer the data. It is intended that any physical data memory device besides a card can be used to acquire the product identifiers such as floppy disks, hard disks, optical disks, opto-magnetic disks, tapes, CDs, cartridges, semiconductor medium, and the like for later transmission to the server 10 or to communicate with the server 10. Furthermore, any of the input/output devices can be connected to a printer 39F for printing a list of the selected product identifiers transmitted with or without an associated bar code printed. If the bar code is printed, the user can then take the printed bar code 39H and later scan the printed bar code at the user's domicile.

When the IECLD 40 interfaces with the home-monitoring devices (HMD) 50 and a connection is established between the user 90 and the GPI server 10, the user 90 can transfer the biological variables to the GPI server 10 with the data acquired being transmitted to the GPI server 10 and stored under the biological variables (BV) database 508 for that particular username. For instance if user Mr.XYZ has an eye pressure of 28, a blood pressure of 140/90, a blood sugar of 210, an average temperature of 98.6 F, and a weight of 250 lbs., then all of this data which is acquired from the home-monitoring devices (HMD) 50 is then transmitted to the GPI server 10 and stored under the BV database 508 for Mr.XYZ with address Mr.XYZ@TYG.net. The GPI server 10 then checks to see if there are any messages, warnings, information, recall or Web pages related to the product's UPI code or if there are any potential interactions between the biological variables stored and the products used by a particular username stored in the GPI database, with such information as what biological variables can interact with the effects of drugs, food, and the like, and vice-versa.

In accordance, in an exemplary embodiment, a patient is prescribed a drug called Dexfenfluramine (Redux®) as an appetite suppressor. In this particular embodiment the patient enters his personal and demographic data in his portable unit 40 or, alternatively, the patient can enter the same data by using any personal computer system 30, with the initial data including a username and/or IP address which uniquely identify the user. Although the patient could enter his own name, it is preferable that the patient enter a pseudo-name in order for the medical information to remain confidential and not be associated with the patient's real name. This is an advantage of the recall system as disclosed in the present invention which preferably uses the user's pseudo-name and Internet address to inform the user about a recalled product that the user is utilizing. Thus, the invention allows the user to remain anonymous during the entire process of acquiring, transmitting and storing his medical data and then receiving the recall information. Thus the patient Mr. Gerald M. M. Jones enters his name as Mr.XYZ@GPI.org or Mr.XYZ@TLJ.net or Mr.XYZ@Yale.edu and the like. Subsequently, the user, optionally, enters his age and other personal information, as well as type of health plan and medical information related to pre-existing medical conditions and current medical therapy and/or medical diagnosis. It is understood that although the patient can input as much personal/medical data as he/she wants, the system of the invention can be carried out, in the preferred embodiment, by simply having a username as defined by the principles of the invention.

In a preferred embodiment Mr.XYZ also has means to acquire data related to his biological variables and/or has home-monitoring devices 50 with IECLD-like features and means to transmit the data to the main GPI server 10 either directly from the home-monitoring devices 50 or by using the portable unit 40 which, in a preferred embodiment, acquires the signals from the various home-monitoring devices 50. Although the preferred embodiment uses biological variables acquired by home devices, it is understood that biological variables acquired in other places, other than the user's domicile, such as doctor's office, hospital, and the like, can be used with the data thus acquired and transmitted for storage in the main GPI server 10. Although the preferred embodiment uses acquisition, transmission, and storage of biological variables for the particular user, it is understood that the system of the invention can be carried out simply with the acquisition, transmission and storage of the products being utilized by the user.

After entering personal/medical data, the user is requested to choose a PIN or password and login name, preferably the username for example Mr.XYZ, with all of the above information being stored in both the portable unit 40 as well as transmitted for storage in the main GPI server 10, creating a file for Mr.XYZ in the GPI database stored in the user's personal information database 514. Subsequently, the GPI central server 10 is ready to acquire, process, transmit and receive any data or information concerning products being used and/or biological variables being acquired on Mr.XYZ according to the principles of the invention. In the exemplary embodiment, Mr.XYZ was prescribed Dexfenfluramine (Redux®), and thus the Dexfenfluramine UPI, which uniquely identify that particular package and specific contents of that package, is acquired by reading the bar code symbology with a bar code reader of the portable unit IECLD 40. The data acquired by the portable unit 40 is then transferred to Mr.XYZ computer system 30 which in turn is connected to the Internet 100 and the data further transmitted to the GPI server 10 for storage as, for instance, under Mr.XYZ@GPI.org in the drug database 6A having file Dexfenfluramine and/or code 090911919.

Although the use of optically-encoded symbology provides the most time-efficient, orderly and virtually error-free system as used in the preferred embodiment, it is understood that the user can enter and transmit this data in a variety of ways including wireless acquisition and transmission, keyboard entry, physically wired connection, and the like, and alternatively the pharmacy or any point-of-transaction can transfer the information. In some cases the user of the product can use the serial number of the product which is already in the package and manually enter the data into a conventional computer system for transmission to the GPI server 10.

A further example will illustrate the value of the present invention. Mr.XYZ has moved to another state or country and has about a year's supply of his Dexfenfluramine (Redux®) or, in another scenario Mr.XYZ will be on a trip abroad for the next 4 months. Suddenly, during post-market surveillance, the FDA uncovers potentially fatal adverse reactions caused by this drug Dexfenfluramine (Redux®) and issues a recall. The drugs from the pharmacies are recalled, but the ones already being used are still out there being used by millions of patients across the world. Expensive printed matter to health care providers and institutions are distributed, but there are no means in the prior art to address and identify the actual individual unique user of the product, and thus unfortunately the actual user cannot be directly addressed and is at risk of injury/illness and death. As mentioned, public announcement recall through media is used in order to alert patients to stop using the drug with the dire financial consequences to the manufacturer and distributor who now have to go public and basically admit that they have made a product that may harm or kill people. Furthermore, this system is quite ineffective and neither identifies the individual user nor identifies all the users of the product. With the present invention, as soon as the FDA 130 issues even a warning or a recall for the drug Dexfenfluramine, the recall information is immediately and preferably electronically transmitted to or acquired by the GPI server 10 as Dexfenfluramine code 090911919, and the GPI server 10 automatically stores the recall information acquired in the alert database 512. Each time the server 10 receives product information, the server 10 checks its database for users of the product. In the case described regarding the recall of Dexfenfluramine, the server 10 searches its database to identify all users of Dexfenfluramine code 090911919 and, after the users are identified, the recall notice is instantaneously and automatically and electronically and privately sent to all users of the drug alerting them about the fatal risk involved with the use of the drug, with electronic transmission preferably done using conventional e-mail. The system of the invention can then timely locate and alert all of the users using immediate electronic transmission of information regardless of the user's physical address or even if the user has moved and/or is lost to medical follow-up or is on a trip abroad in Mongolia. The system thus provide means to locate each user individually by using an exclusive unique name and address, as the Internet address. The real name of the user of the drug remain confidential and the name of the company with the recalled product has minimal public exposure since it can privately address the users of the recalled product and thus preserve the company's name.

Returning to the example of Mr.XYZ, he is travelling abroad and has basically no means to know about the recall in his country of origin. However, Mr.XYZ can have continuous access about recalled products that he is using by either using his portable IECLD 40 unit with connection to the Internet 100 or has means to connect to the Internet 100 with conventional computer terminals 30. Then as soon as Mr.XYZ either checks his regular e-mail; or web-based GPI site e-mail; or logs in the GPI website and enters his password, the specific information (not random) on the recalled drugs that Mr.XYZ is using is disclosed and displayed on the display of his computer device.

The GPI system 1 thus allows any remote user to access the information on potentially harmful products being used by the user. Besides warning about the fatal risk with the drug, the system also instructs the patient on how to proceed. In this case a particular formulation of the drug-type Dexfenfluramine was later found out, after almost two years on the market, to cause severe and potentially fatal heart disease by affecting the valves of the heart. In response to that, the GPI system 1 instructs the patient about alternative products, actions to be taken including how to stop the drug, and the need to see a heart specialist and to have an echocardiogram done. The GPI system also automatically contacts the patient health care provider and schedules an appointment, contacts the hospital and laboratory and schedules the test (echocardiogram), and contacts the patient's health plan for approval if needed for the tests and appointments. The GPI system 1 sends information on the recall to the health care provider (doctor) with the name of a replacement for the recalled drug and a list of patients using the drug with the phone number of the pharmacy for each patient. This GPI function provides an important service to the doctor. The doctor receives the names of patients, thus the doctor does not have to review charts to try to find out if any patient is using a recalled drug. In addition, as mentioned before, this is impractical. The doctor also receives the phone number of the pharmacy for each patient, and thus the doctor does not need to call patients and search to find out what pharmacy to call for prescription concerning the replacement drug. Simultaneously the patient using the recalled drug receives a message that the his/her doctor has been contacted and a prescription filled at his/her preferred pharmacy, including a message to "call the pharmacy to find out if the replacement drug is available for pick up". The GPI Safety Program thus provides a complete, efficient and low-cost comprehensive prevention and treatment of illness/injury caused by a harmful product. Furthermore Mr.XYZ will have an option to fill out an electronic questionnaire about cardiopulmonary symptoms and other symptoms in order to better assess the level of urgency for medical therapy since Mr.XYZ is travelling abroad. The present invention also provides a complete set of instructions according to official and medical recommendations such as the need for antibiotic prophylaxis when Mr.XYZ undergoes a dental or medical procedure in case he has the heart valve disease caused by the harmful drug.

The GPI system 1 has the ability to continuously locate a patient and alert the patient about potential problems with the products they are using. For instance, patients who have had permanent implants are often lost to follow-up, with the doctor being unable to locate the patient and inform about the complications related to the product being used or implanted. Even if the patient moves, change addresses, or simply cannot be reached, an update about the prosthesis permanently implanted could be sent to the patient as long as they have their IECLD 40 or access to the Internet 100 and log onto the free GPI web site. If the patient has access to the Internet 100 and knows the UPI code number or name of the product, then the data can be entered using a keyboard and the patient can access its GPI server 10 file or general recall information at the GPI web site. Patients usually carry a card identifying the number of the prosthesis which was implanted and can check the information related to the prosthesis. The same also would apply for patients receiving living issues such as kidneys or any other type of transplant. If the subject who donated the organ was later identified as having a transmissible disorder such as viral disorders, the recipient of the organ could be notified and instructed how to proceed.

If the user is buying or using a product which does not have a UPI, the user can enter the name of the product and, if a recall notice has been issued for that product, the GPI system 1 will match the name against its database and identify the product with the consequent recall alert sent to all of the users of the product. If for instance the user is buying products over the Internet, then the product purchased can be transmitted to the GPI server 10 using conventional applications. For example, if a vitamin being sold over the Internet were being recalled, the user of the GPI system 1 could, before actually purchasing the product, send the information to the GPI server 10 which would return any recall or information available on the product. Thus, by alerting the user before the user purchases the potentially harmful product, the user saves money and avoid health risks.

While the system is being described in connection with human use, it is understood that veterinary and other non-human use is another alternative application of the current invention in regards to identification and location of harmful or recalled products.

One aspect of the invention provides a system composed of HTML documents and information transfer using Hyper Text Transfer Protocol (HTTP). Although the exemplary embodiment uses data communication using HTTP, other protocols such as FTP, Gopher, XML and other emerging protocols can be used to transfer recall, harmful or beneficial information on particular products being used by a particular user and biological variables for the user. Although the exemplary embodiment uses HTML documents, it is understood that many other types of documents can be used, including but not limited to Adobe PDF, motion pictures, still pictures, voice or any other means related to the provision of information about potentially harmful or beneficial products, recall and interaction information.

Figure 7A:
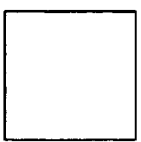
FIG. 7 is a menu diagram illustrating exemplary product recall and information menus that can be displayed in an open display window on a user's personal computer in accordance with the embodiment depicted in FIG. 6.
Figure 7B:
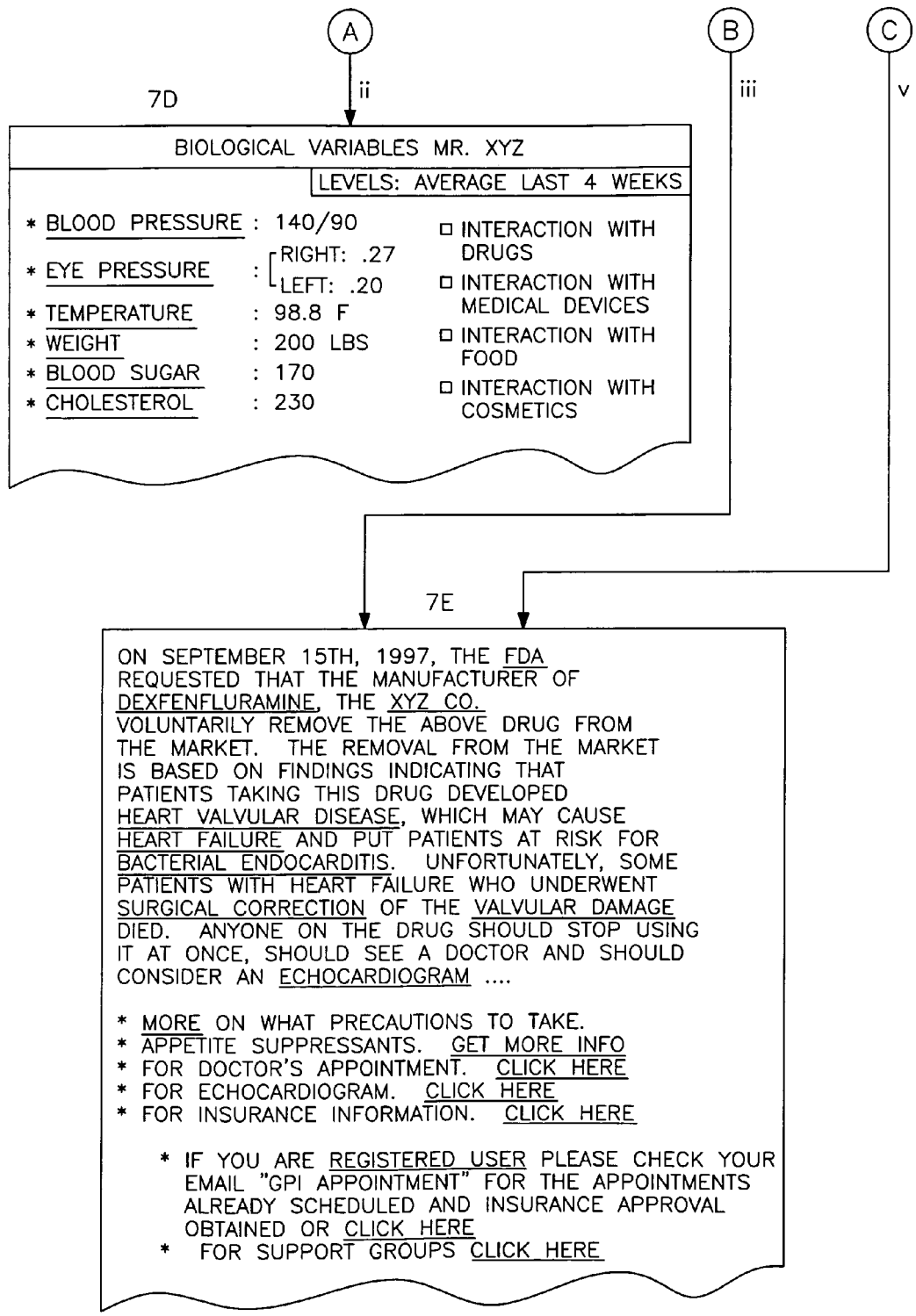

FIGS. 7A-7E are exemplary diagrams showing second, third and fourth windows opened on a user's computer. FIG. 7A shows electronic information converted to an HTML document depicting an exemplary home web page for the free web site, GPI Recall, Location and Information System, as it appears on a computer system 30 display screen or a portable IECLD 40 device with Internet and HTML capabilities for both registered and non-registered users. FIG. 7B is an exemplary diagram of the electronic alert and recall documents with hyperlinks displayed on a computer of a registered user. A secured page "GPI Products Alert/Recall" (accessed only by the user of products presented in that page, after appropriate identification is confirmed) with information on products used, biological variables, and information on recall and effects (harmful and beneficial) is shown. The information about the various products used by the user and associated hyperlinks are displayed on the document. To illustrate in more detail this particular document, the "GPI Products Alert/Recall" document shows a box with the itemized product groups being used by Mr.XYZ which can be individually accessed by point-and-click. A second box in the same document shows the current information on recall or warnings for the products used by Mr.XYZ with the product name and group in one column and the information about the product in a second column with its associated hazard degree code, all of which accessible by point-and-click. FIG. 7C is an exemplary diagram of a non-restricted document on recall and alert, displayed on a computer of a non-registered user. FIG. 7D is an exemplary diagram of biological variables with hyperlinks, displayed on a computer of a registered user. In FIG. 7D, a portion of the secured document Biological Variables for the particular user is shown with the values measured and the links to the various potential interactions of products being used with the biological variables measured. FIG. 7E is an exemplary diagram of a document displayed on a computer of a registered user with a variety of hyperlinks to manufacturer and government computers. A portion of the page, Recall Info, shows text and HyperText illustrative of recall of a certain drug with links to documents relevant to the recall such as, to the manufacturer, to the recall government agency, and links to support groups, information on the medical condition, how to get a doctor's appointment (with both doctor's located in brick-and-mortar offices or Internet offices) and scheduling of laboratory test (echocardiogram) and insurance information. The portion of the document, Recall Info, also has links for registered users to access personal and confidential information such as previously scheduled appointments and insurance approval.

The registered user can access the personal and private information on recalled products used in different ways. One preferred way includes the user checking his/her GPI web-based e-mail, and in this case the user receives in his/her e-mail box all of the secured pages related to warning and recalled products such as GPI Alert/Recall document (7B), Biological Variables document (7D), Recall Info document (7E), appointment and insurance information, and the like. Another way is for the user to log onto the GPI web site and with his/her password access the same personal/private information, as described above, on products being used, biological variables measured and alert/recall information on these products. A further way to retrieve the personal/private alert/recall information is by reading his/her conventional text e-mail messages.

The information on products used, biological variables and personal appointment information is in a secured area accessible only by the user of the products. Alternatively, the page Search and Recall Info (FIG. 7C) represents non-secured documents and can be accessed by anyone simply by logging onto the GPI web. Thus, the GPI system provides a free service to both registered and non-registered users. However, the registered user does not have to search for recalled products or warning or information on products being used, since the GPI system 1 delivers such information on products being used to registered users automatically. This is in addition to all of the other numerous additional advantages such as information on the beneficial effects of products being used.

This system helps companies reduce their exposure to the financial disaster that may occur as a result of publicly announced recalls through the media as previously explained. Moreover, the companies and government agencies avoid the significant costs associated with conventional printed, televised and audio recall and warning about potentially harmful products.

The system of the invention searches and/or acquires data from the various RIS 60 not only about the harmful effects of products, but also the newly found beneficial effects of products. For instance in FIG. 7 the document Alert/Recall 7B shows in the product column D1—"Verapamil" and under information "beneficial". In this particular case, a RIS Research Institution 60 and a RIS Medical Institution 60 transferred information that verapamil was found to decrease eye pressure. This patient has hypertension and is using this drug verapamil to treat his hypertension. This patient also has abnormal and elevated eye pressure. The information indicating that verapamil decreases eye pressure is checked against the users' database, and since this user has glaucoma with increased eye pressure, the interaction product-biological variables is considered beneficial and the information is transmitted back to the user as previously described.

The GPI website also offers a unique feature called "Spend more time with your doctor". Doctors have an enormous amount of knowledge and information, but in the U.S. patients only spend an average of 8 minutes with their doctors. Thus, many questions and concerns about drugs prescribed or other products used go unanswered. As soon as the product is added to the users' usage record in server 10, the information on the product is transmitted to the user 90. The information that could have been acquired by talking to the doctor is sent to the user, giving virtual extra time with the doctor. This is done at the user's discretion and the user may choose not to receive such of product information.

FIG. 7 also shows the GPI home page 7A linked to the GPI AlertRecall page 7B by means of link (i) which in turn is linked to document Biological variables 7D by link (ii). Document GPI Alert/Recall 7B is also linked to page Recall Info 7E by means of link (iii). Home page GPI 7A is linked to Search page 7C by means of link (iv), which in turn is linked to page Recall Info 7E by link (v). Although the links shown relate to text document only, it is understood that images, videos, sound, programs or any binary data link can be implemented and used. For example, the HyperText surgical correction can be linked to an actual video of a heart surgery with valve replacement, which gives more information for the user of recalled products while allowing the users to seek immediate therapy and better evaluate all of the potential aspects related to the delivery of health care for his/her medical condition caused by the harmful product. It can be easily appreciated that the principles disclosed in this section can be applied to any product including but not limited to the main product groups (drugs, cosmetics, food, medical devices, toys/baby products, and miscellaneous) and the user informed about the potential hazards and recalls associated with the products being used. It is clearly also noted that the figures presented are simply a way to illustratively describe one of the embodiments of the present invention, but obviously there are numerous other ways to display and deliver the information and many variations all of which can be used in the present invention. Moreover, in accordance with the principles of the present invention, user applications such as a web browser can set up a connection to the remote GPI server 10 in order to retrieve the information on potentially harmful products that is requested by a user. As an example, a user browser application displays a hyperlink associated with documents related to the recall/warning and information system for a unique user, which can be selected with another document being retrieved over the Internet from the GPI server 10 in which case the GPI server 10, acts as a HTTP server 10. It is understood though, that the present invention can be employed with other types of user and GPI server 10 applications allowing access to certain sources and certain data over the Internet 100 with the data and/or sources relating to harmful/beneficial products and/or recall/warning information. It is also understood that the user 90 and server 10 computing systems according to the present invention can include a variety of operating systems and commercial applications to assist the implementation of the needed acquisition and transfer of information related to the potentially harmful products with creation and transmission of messages.

Besides informing the user about the harmful effects of products, the GPI system also informs the user about the potential beneficial effects of the products being used. If Mrs.XYZ has stored in the GPI database that she is age 50 and using estrogen replacement, the GPI system 1 identifies that association as beneficial since during post-market surveillance the GPI system 1 has acquired from RIS 60 information indicating that estrogen use in post-menopausal women reduces death from cardiovascular disease.

In another embodiment the user has stored in his/her personal information database that he/she has a family history of Alzheimer's disease. Information about a drug that helps Alzheimer is transferred from the RIS 60 to the GPI system 1, indicating "low doses of risperidone, regularly prescribed for schizophrenia was found to help relieve symptoms in Alzheimer's patients and may delay hospitalization. Please consult your doctor." In this instance, although the user does not have Alzheimer, since he/she has a family history of Alzheimer the information is sent to said user which allows the user to better care for a family member with the disease. This information could also be useful to the doctor who may not be aware of the potential beneficial interaction, and the information is also passed on to the doctor.

Another embodiment relates to use of the system not only by patients, but also doctors, medical institutions, and the like. In an exemplary embodiment, doctors who prescribe certain drugs and medical institutions which use certain devices could easily acquire the unique UPI for the drug or device and send the unique UPIs to the GPI server 10, allowing the doctors and medical institutions to have updated information in regards to the products being used by the practitioners and/or institutions. Furthermore, although the present invention can be preferably used by an individual user of a certain product, alternatively the current invention can be used by the provider prescribing the product or the institution delivering health care or the establishment selling the product. In this alternative embodiment the hospital, providers, establishments, seller, distributor, and the like send the information on the products to the GPI server 10 and receive feedback specifically tailored to the products being used or delivered or sold by the practitioners and establishments. For example, if a doctor prescribes risperidone on a daily basis, then the doctor transfers the UPI according to the principles of the invention described, and the information is stored in his/her database. In this embodiment the UPI stored relates to drugs being prescribed by the doctor, and not the UPI for drugs personally used by the doctor. Then when new information related to risperidone such as beneficial effects, harmful effects, and recall information is transferred from the RIS 60 to the GPI server 10 according to the principles of the invention, the information is then automatically electronically sent to the doctor as an alert message. Naturally, the same information and updates would apply to all of the commonly used prescribed drugs by the doctor which are stored in the user database as products being used. In addition the GPI server 10 can send Safety Alerts and labeling changes for drugs according to the doctor prescription pattern. Thus this alternative embodiment is an incredibly useful tool for any doctor helping to deliver the specific information that the practitioner needs according to his practice and prescription patterns. In this case the doctor could have two registered names: Dr.X20@GPI.org in which the user/doctor stores in the product and user database the names of drugs commonly prescribed, and then have another registered name Mr.X20@GPI.org in which the doctor stores in the user and product database his personal list of drugs and other products being used. This thus allows the GPI system to meet both the personal as well as the professional needs of the user.

If a product that is uniquely identified with a code or its name is transferred to the GPI database by a registered user, that code or name can be stored in the Miscellaneous database 6F. Then the registered users of the products, according to their preference, will receive updates tailored to the products stored under their username, such as but not limited to, software downloads and updates related to the recalled product stored in the GPI database, links to Internet resources related to the product stored in the GPI database, and the like. This same alternative embodiment could be used by a merchant or medical institution interested in receiving updates and information about a particular group of products being sold or delivered. In an exemplary embodiment, a restaurant serving fish will have in the products database Food the types of fish being served by the restaurant, and then if any of the RIS 60 send information for example stating "cod found to decrease blood pressure", then that information could be used for the benefit of the customers eating at that restaurant. The restaurant can disclose in the menu that according to source FDA 130 cod was found to reduce blood pressure. Then a customer with high blood pressure can make an educated choice concerning his/her health and choose cod and thus better control his/her blood pressure. On the other hand, the customer with low blood pressure or taking drugs to lower blood pressure can make an educated and healthy choice of not eating cod since that could aggravate his/her status, potentially leading to lower pressure, dizziness, and even a car accident due to the exceedingly low blood pressure caused by eating cod. In another exemplary embodiment, a farmer using a certain fertilizer will have in the product database Miscellaneous a memory area for chemicals, or alternatively the drug area memory can be used as chemicals and drugs. Then the RIS 60 provides information concerning the type of fertilizer used by the farmer stating "fertilizer FZ found to be mostly beneficial in crops, such as corn, and actually detrimental to wheat." In this case the farmer then can use the information to optimize production since the GPI System 1 delivered valuable information for increasing crop production specifically tailored to that individual user. Since the GPI system 1 only uses well-founded and proven information and data from well recognized established government and private institutions, the information acquired from the RIS 60 can be considered sound and valid, and thus very useful.

Although much less frequent, harm by a product can occur in a very odd manner, and the present invention can prevent even these unusual harmful events. More specifically, a book purchased in the USA by a user who went back to China had a printing error that could cause harm. Without the present invention, the user would never learn of the harmful printing error. However, with the present invention the user in China receives the Alert message stating that "the combination proposed for experiment 12 about x-ray may pose a serious radiation hazard, please refer to the enclosed information for the correct sequence for the experiment". Although, only a few exemplary alternative embodiments are disclosed herein, it is intended that the current invention can be used with any product, subjects, articles, and the like, tangible or non-tangible items, which have an identifier indicia, belonging to or delivered or acquired by any individual, establishment, entity, and the like, with data and information preferably transmitted to the user via the Internet or a public network according to the principles of the invention.

The GPI system 1 is also designed to acquire information from the user 90 which may be significant from a warning or recall standpoint. The GPI system 1 uses biological variables to determine if a certain UPI product has been consistently and temporally associated with an abnormal biological variable. In the case that hundreds of users using a certain drug PPS transfer biological variables consistent with abnormal heart rate, then the data meet the criteria for potential harmful effect of the drug PPS. This information can then, for example, be transferred to the RIS 60 as "drug PPS potentially implicated with abnormal heart rate". In this scenario the GPI system 1 acts as an auxiliary in the detection of harmful products. The same approach applies to the detection of a certain plant number or lot numbers causing widespread illness or injury. The information thus can be used for locating plants for inspection. The system 1 can also identify contaminated food before an outbreak occurs. The users can transmit information to the GPI system 1 about their symptoms and comments on the product such as labeling, appearance, questionable ingredients, and the like. When a certain number of users report similar symptoms after ingesting the same food, the GPI system 1 identifies a potential outbreak. The system GPI 1 then can transfer this information back to the RIS 60.

As previously stated, the GPI arrangement is designed to be a completely free-of-charge system to any user of any product, but for the sake of completion of the description of the invention, a few exemplary compensation methods are described. Naturally the transfer of UPI or biological variables or receipt of keys may only occur after the occurrence of appropriate transfer of funds to the GPI server 10 and/or to a third party. Furthermore, appropriate transfer of funds to the GPI server 10 and/or a third party may be required at any time and may occur at any of the steps described in this whole specification. It is also understood that a tracking arrangement for the number of requests and/or information delivered or acquired by either the user or/and the RIS 60 can be used as a means to quantify and charge for the utilization of the system. There are herein described only a few embodiments and modifications concerning environmental as well as compensation issues, but it is understood that the invention is capable of use in various other environments in conventional messaging and broadcasting, as well as in any 'cyberspace" environment based on the Internet and using a variety of payment methods and account databases. Naturally it is understood that the user can block receipt, or select products and conditions for which the user wants to receive information, messages and/or web pages.

The system is constructed as a pure electronic system with no inventory, nothing to ship, and no warehouse. The system can provide personalized advertisement according to product identifiers and sales of replacement products as substitutes for the recalled products. Participant companies interested in offering the GPI Safety Program to their customers can benefit by being able to sell alternative replacement products to the customers who purchased a harmful or recalled product. In an exemplary embodiment a company recalling a harmful product can offer, in the Alert Message or in any electronic means to report the recall alert, an alternative product that is proven to be safe or a newer more advanced model. In case the company recalling the product does not have an alternative product, the GPI system 1 will offer replacement products from other participating companies or non-participating companies.

The above financial benefit offering a new source of revenues should further encourage companies to offer the free-of-charge GPI protection program to customers. The GPI system 1 can be maintained by charging a fee according to replacement products sold by the participant companies or by receiving a fee according to the number of recalled products identified, located, or removed from the market or alternatively according to the number of users identified. Yet every company which offers replacement products can be charged a fee. The companies can have their product information directly reach consumers who need the replacement product. The embodiment involves partnering with GPI member companies for sales of their replacement products and direct to customer activities with personalized sales. Offer of an alternative product is triggered by the product recalled. For each product recalled an alternative replacement product is offered, preferably at a discount rate by the manufacturer of the defective or harmful product. In addition, the GPI server 10 can provide via the IECLD 40, besides alternative products and drugs, reminders about taking medication and reminders for filling or refilling a prescription.

Figure 8A:
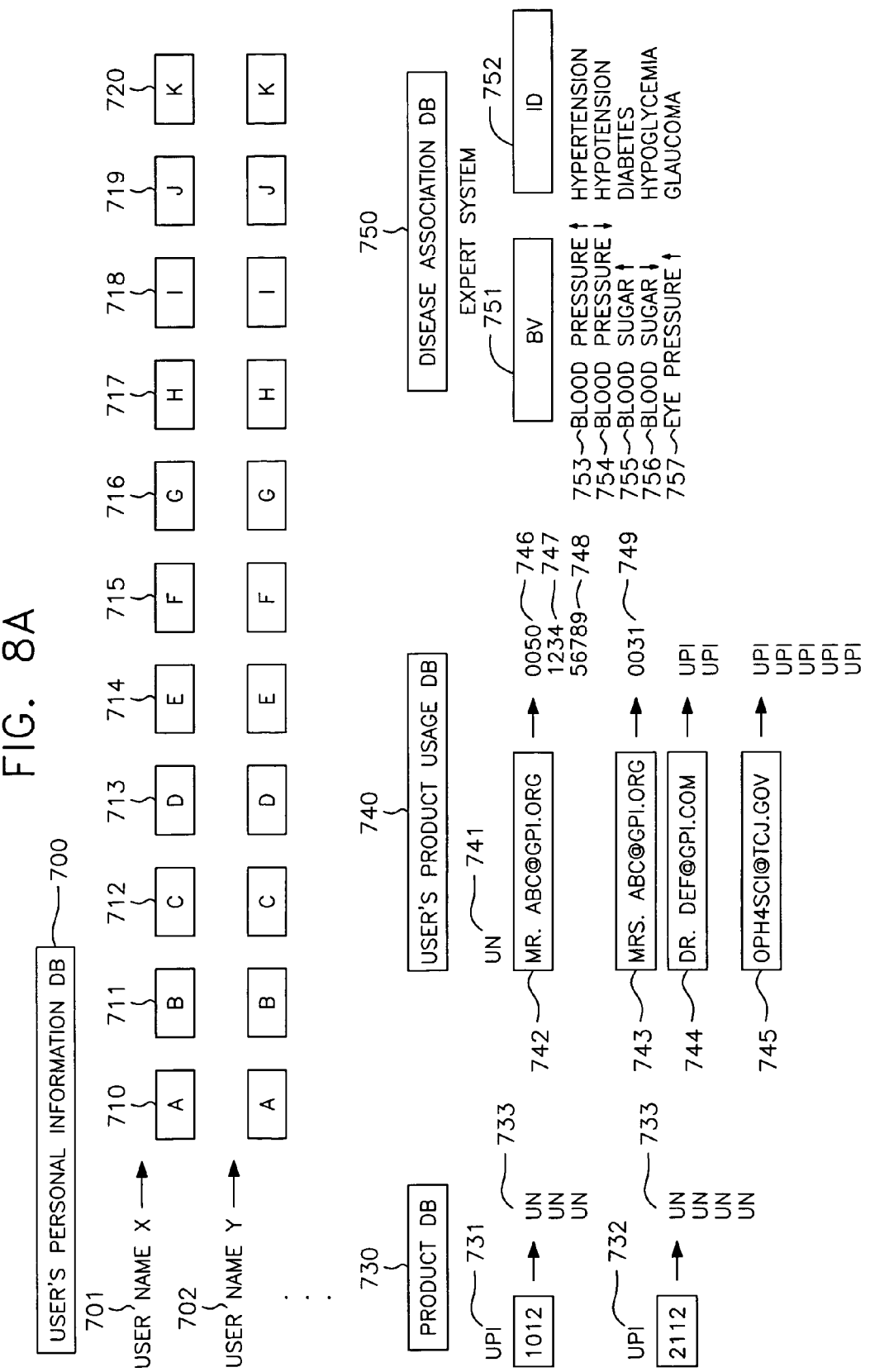
Figure 8C:
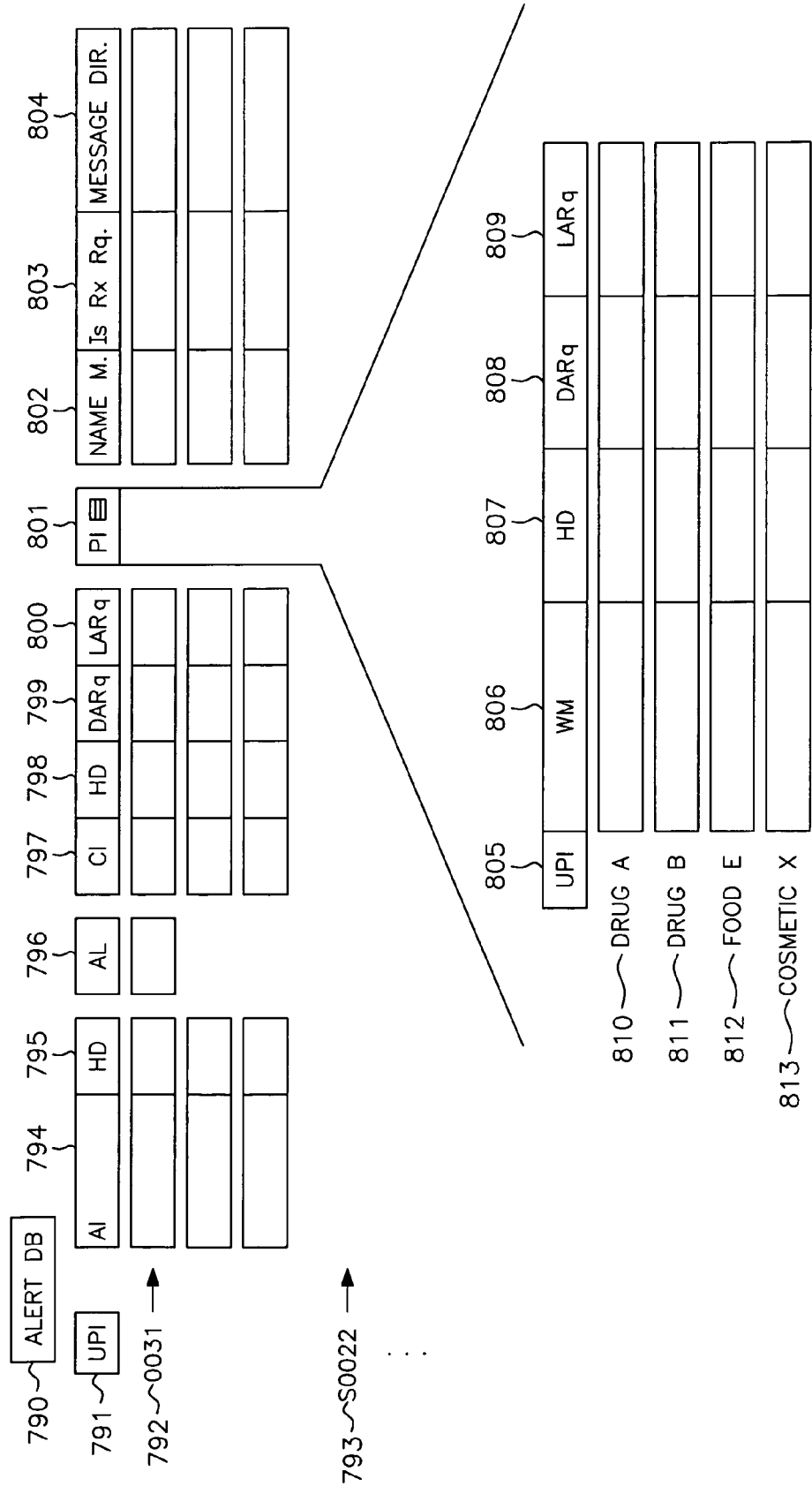

FIGS. 8A to 8C present a schematic view of an exemplary memory, fields and record arrangement for carrying out the principles of the invention. FIG. 8A shows the user's personal information database 700 which is keyed on the username 701, 702 and contains: field A (demographic information such as name, address, occupation, date of birth) 710, field B (password and other security data) 711, field C (doctor's information) 712, field D (laboratory information) 713, field E (pharmacy information) 714, field F (insurance information) 715, field G (current illnesses) 716, field H (range of normal biological variables) 717, field I (timely monitoring period) 718, field J (hazard with untimely monitoring) 719, and field K (inform doctor of abnormal value) 720. The product database 730 is keyed on the product identifier (UPI) 731, 732 and contains field username (UN) 733. The user's product usage database 740 is keyed on UN 741 preferably described as a full Internet address 742, 743, 744, 745. For each UN record there are associated one or various UPIs 746, 747, 748, 749. The databases 700, 730, 740 are primarily updated by the user. The disease association database 750 includes an expert system with fields biological variables (BV) 751 and indicated diseases (ID) 752. The BV field 751 contains the status of the biological variable such as the abnormal values for each biological variable 753, 754, 755, 756, 757, with the disease indicated by the abnormal values contained in the ID field 752.

FIG. 8B shows the product information database 760 which is keyed on the product identifier (UPI) 761 (as example 762, 769) and contains fields (GI) general information 763 (description of the product, precautions, how to use, warnings, and in case of drugs, also includes the indications and usage, effects, side-effects, adverse reactions, and in some cases dosage and administration, chemical and clinical information), contraindication (CI) field 764 with its associated hazard degree (HD) field (Recall, Harmful 1 to 5, Beneficial) 765, doctor appointment required field (DARq) 766, and laboratory appointment required field (LARq) 767. The product information database 760 also contains the product interaction (PI) field 768 with its associated product identifier field 830 with, for example, interaction of product identifier 762 with drug M (product identifier 831) and interaction with food F (product identifier 832). The PI field 768 also contains its associated warning message (WM) field 833, HD field 834, DARq field 835 and LARq field 836.

As an example, product identifier 762 is aspirin with the aspirin UPI 0031 also stored under numerous UN 741 in user's product usage database 740, and product (drug M)_831 is warfarin. Drug M 831 warfarin interacts with aspirin 762. The WM 833 is then "aspirin-warfarin increases risk of bleeding", the HD 834 is H4, DARq 835 is "yes", and LARq is "yes" with coagulation profile required.

The product information database 760 is primarily updated by the manufacturer of the product. The biological variables database 770 is keyed on the UN 771 as example addresses 772,773 and contains parameter field (PAR) 774 (biological status evaluated), value (VA) field 775 (values for each biological function), and time/date (DA) field (time and date at which biological function was transferred going from most recent to least recent). Sample parameters within PAR 774 include eye pressure 777, glucose 778, liver enzymes 779, triglycerides 780, and weight 781. The biological variables database 770 is updated primarily by the user.

FIG. 8C shows the alert database 790 which is keyed on the product identifier (UPI) 791, as example 792, 793, and contains the alert information (AI) field 794 and its associated HD 795 as well as alert level (AL) field 796. The alert information field 794 contains the information acquired from the RIS 60 such as FDA 130. For example, the UPI for Redux® contains in the AI field 794 "patients taking this drug are at risk of damaging the valves of the heart which may cause heart failure and infection of the heart valves which can be fatal", and its associated HD 795 is H4. The AL 796 is R for recall.

The alert database also contains the CI field 797, HD field 798, DARq field 799 and LARq field 800 in a similar structure as the product information database 760 but with the information being related to recall and harmful/beneficial effects and derived primarily from government and regulatory RIS 60. The same UPI 0031 is present in the product information database 760 and alert database 790, but for instance CI 764 relates to established contraindications and CI 797 relates to contraindications newly identified by regulatory agencies. Alert database 790 also contains PI field 801, with its associated product identifier field 805 with, for example, interaction of product identifier 792 with drug A (product identifier 810), interaction with drug B (product identifier 811), interaction with food E (product identifier 812), and interaction with cosmetic X (product identifier 813). The PI field 801 also contains its associated warning message (WM) field 806, HD field 807, DARq field 808 and LARq field 809. The same UPI 0031 in the product information database 760 is known to interact with drug M 831 and food F 832 which are established interactions. On the other hand the same UPI 0031 in the alert database 790 interacts with new products such as drug A 810, drug B 811, food E 812 and cosmetic X 813. These are new interactions found during post-market surveillance which were acquired over time during years of use of the product. As new information from the RIS 60 is acquired, the alert database 790 adds the new interactions found and transfers information to the user of the product, but only to the specific user of the product, thereby optimizing the transfer and use of information. The alert database 790 also contains the fields name of medications (name M) 802, is prescription required (Is Rx Rq) 803, and instructions and directions, including alternative drugs or products (Message Dir) 804 which contains the information needed by the user in regard to drugs and instructions necessary to treat or prevent the harmful effect of the product.

Figure 9:
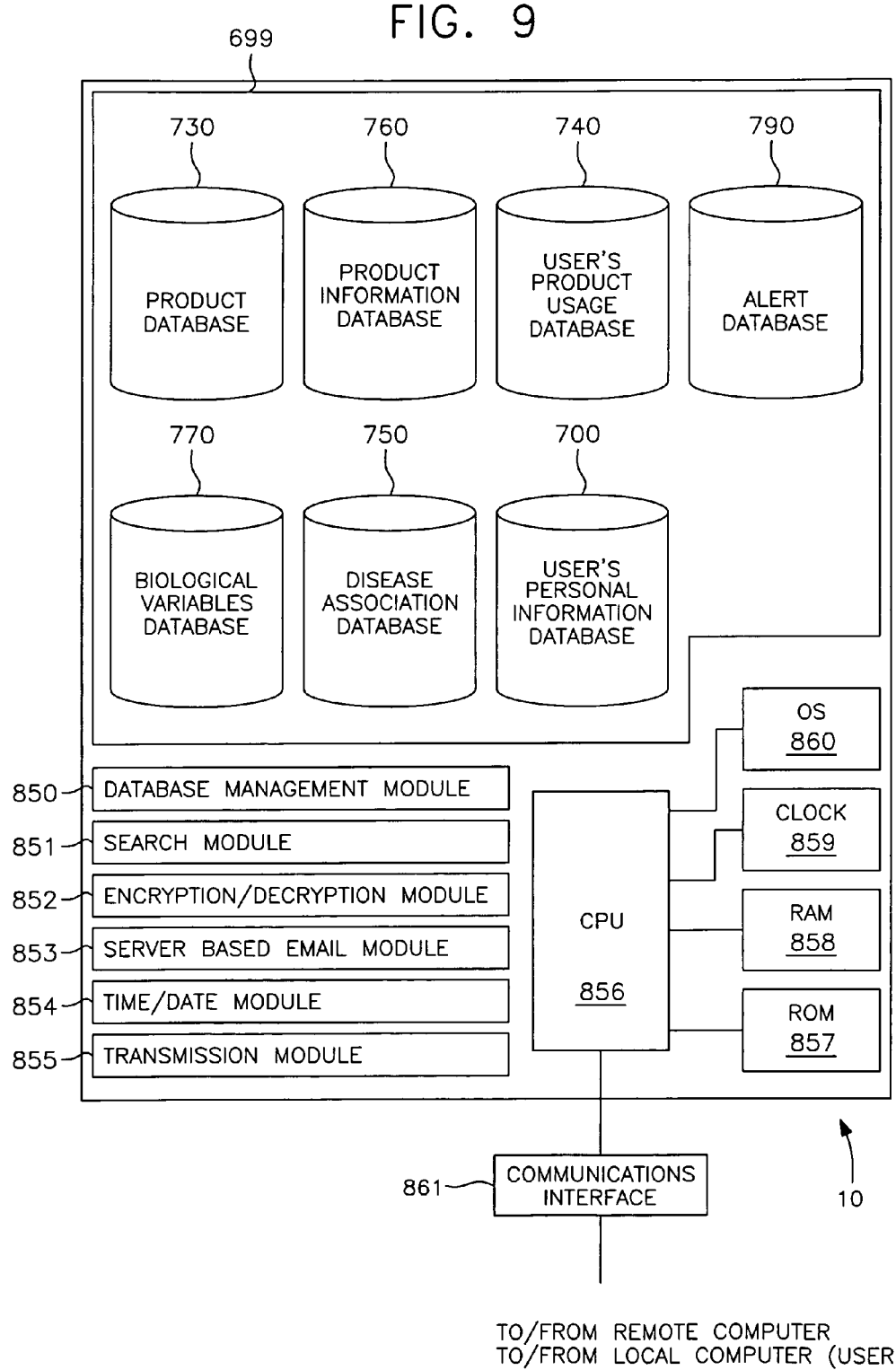
FIG. 9 is a block diagram showing an exemplary embodiment of a central server in accordance with the embodiment shown in FIG. 8.

FIG. 9 is an illustration of an exemplary embodiment of the central server 10 in accordance with FIGS. 8A through 8C and the associated algorithmic logic flow diagrams in accordance with the principles of the current invention. The depicted central server 10 includes data storage device 699 with a product database 730, product information database 760, user's product usage database 740, alert database 790, biological variables database 770, disease association database 750 and user's personal information database 700. The central server 10 also includes a CPU 856, operating system 860, RAM 858, ROM 857, clock 859, and modules to carry out and configure the applications such as general administration module and database management module 850, search module 851, encryption/decryption module 852, e-mail module 853, time/date module 854, transmission module 855, as well as communications interface 861.

The product information database 760 is primarily the result of information derived from a certain type of RIS 60, namely the manufacturer of the product 148. The alert database 790 is primarily the result of information derived from another RIS 60, namely government agencies such as the FDA 130 and the like.

An exemplary GPI server 10 infrastructure includes: (1) High availability server (HA), Rad 5, disk clustering, disk mirroring, and disk shadowing, (2) Redundant gigabit network (OC3), (3) SAN (storage area network) with a Tivoli system, (4) web server (5) Demilitarized zone (DMZ) with double firewall (6) Server hardware such as Compaq ES 40, or alternatively the IBM RISK 2000, with multiple processors and UNIX operating system, (7) Database Management Product such as Oracle 8 or higher, (8) UPS (uninterruptable power supply), (9) multiple modem lines with autodialers, (10) fax modem, (11) IVRs.

FIGS. 10 through 20 show algorithmic logic flow diagrams to carry out the operation in the most efficient way while optimizing time spent online, according to the principles of the invention. It is to be understood that changing the amount of time online and/or continuous coupling between local computer (e.g., IECLD 40, computer system 30, or the like) and the server 10 and other connections/processing variations are considered alternative embodiments, but do not optimize the use of communications medium.

Figure 10:
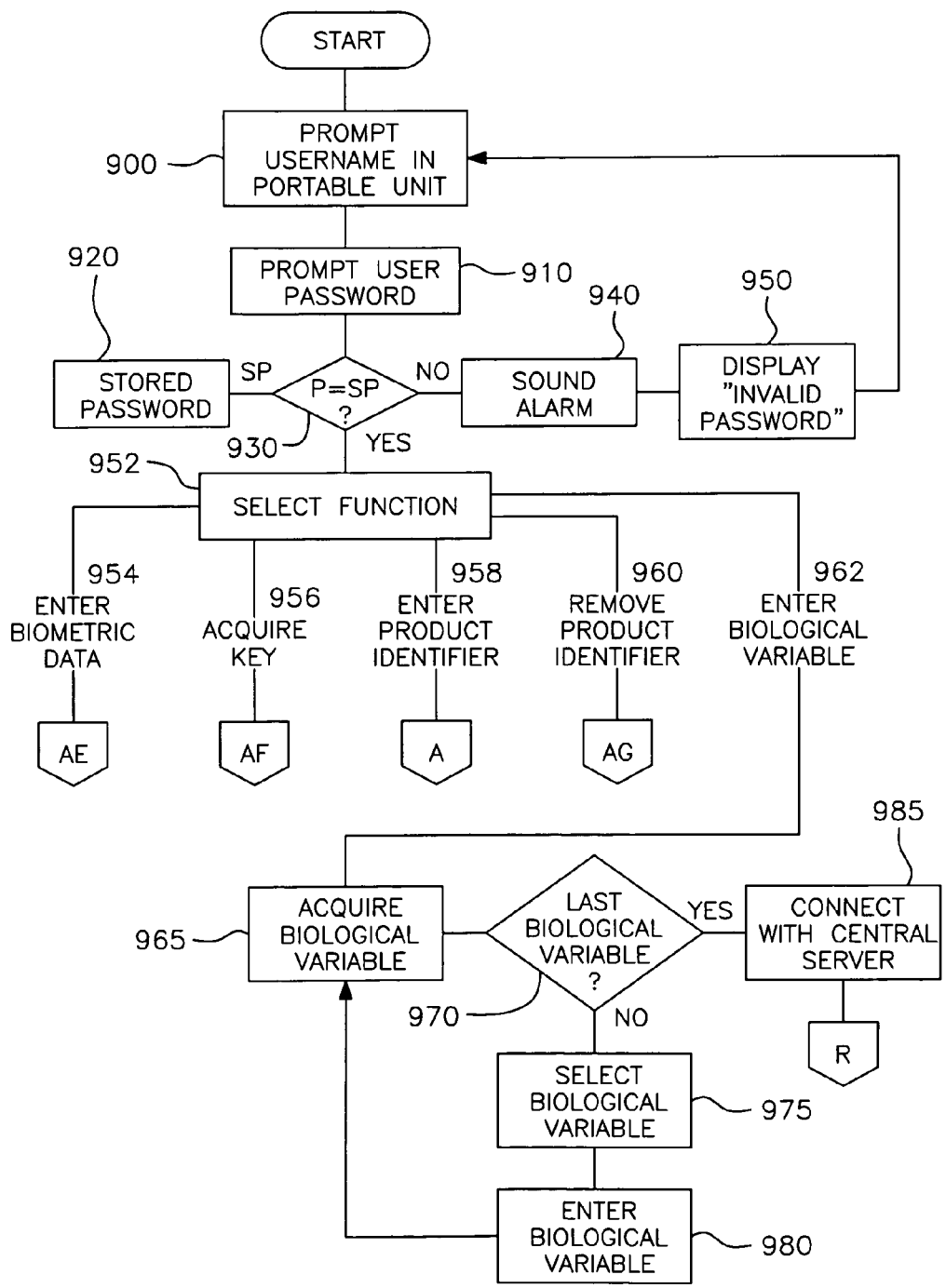
FIG. 10 is a flow chart illustrating initial processing according to the principles of the invention.

In reference to FIG. 10 there is shown a flow chart of an exemplary data acquisition procedure in the current invention by the portable IECLD 40, and with options for subsequent transmission of data. The illustrative steps depicted refer to a preferred embodiment where the user acquires optically encoded unique product identifiers using a bar code reader mounted in a portable hand-held programmable microprocessor such as for instance the IECLD 40. It is intended that other manual or automatic means of acquiring the unique product identifier can be used, such as manual keyboard entry, verbal entry, RF, optical, satellite, cable, telephone lines as well as any other wired or wireless means. Telephone lines, for instance, can be used for acquisition of UPIs at the point-of-sale. It is easily appreciated by one skilled in the art that the user can enter and transfer unique product identifiers using standard computer systems 30 previously described and thus bypass the IECLD 40. The GPI system 1 can also work using different links such as on-line connection, off-line connection, direct link, and the like, and the few following examples will better demonstrate the options. For instance, the user can transfer the UPI and remain connected with the GPI server 10, receiving immediate product recall/information feedback, or the user can send the UPI and biological variables, and then disconnect from the GPI server 10. As another example, the user can remain online but if there is no information in the GPI server 10 for the UPI transmitted by the user, then the user disconnects and in this later case as soon as the information on the UPI is transferred to the GPI server 10 by the RIS 60, the recall/product information is transmitted to the user who may be connected or disconnected to/from the GPI server 10. Alternatively, the user may only receive information by conventional e-mail from the GPI server 10 after transmitting biological variables and/or UPIs, and so on. The e-mail Alert Message can connect the user with the GPI website for further information on the recalled product.

In the exemplary embodiment of FIG. 10, the user activates the IECLD 40 and the first step during the process is to prompt the username at step 900 and password at step 910. The user then enters his username and password in the standard manner. The password is stored in the portable unit 40 and compared with a corresponding stored password 920, preferably stored within another memory unit in the portable unit microprocessor. If there is a positive match between the entered password and the stored password at step 930, then step 952 proceeds to the next operation. If there is no positive match an alarm will sound, step 940, informing the user that the password is invalid, step 950. It is understood that a variety of other means to ensure security and password systems are described in the prior art and can be used in the invention.

Once the password is validated, a Select Function screen is displayed, step 952, allowing the user to select the desired function. These functions include enter biometric data 954, acquire key 956, enter product identifier 958, remove product identifier 960, and enter biological variable 962.

Figure 11A:
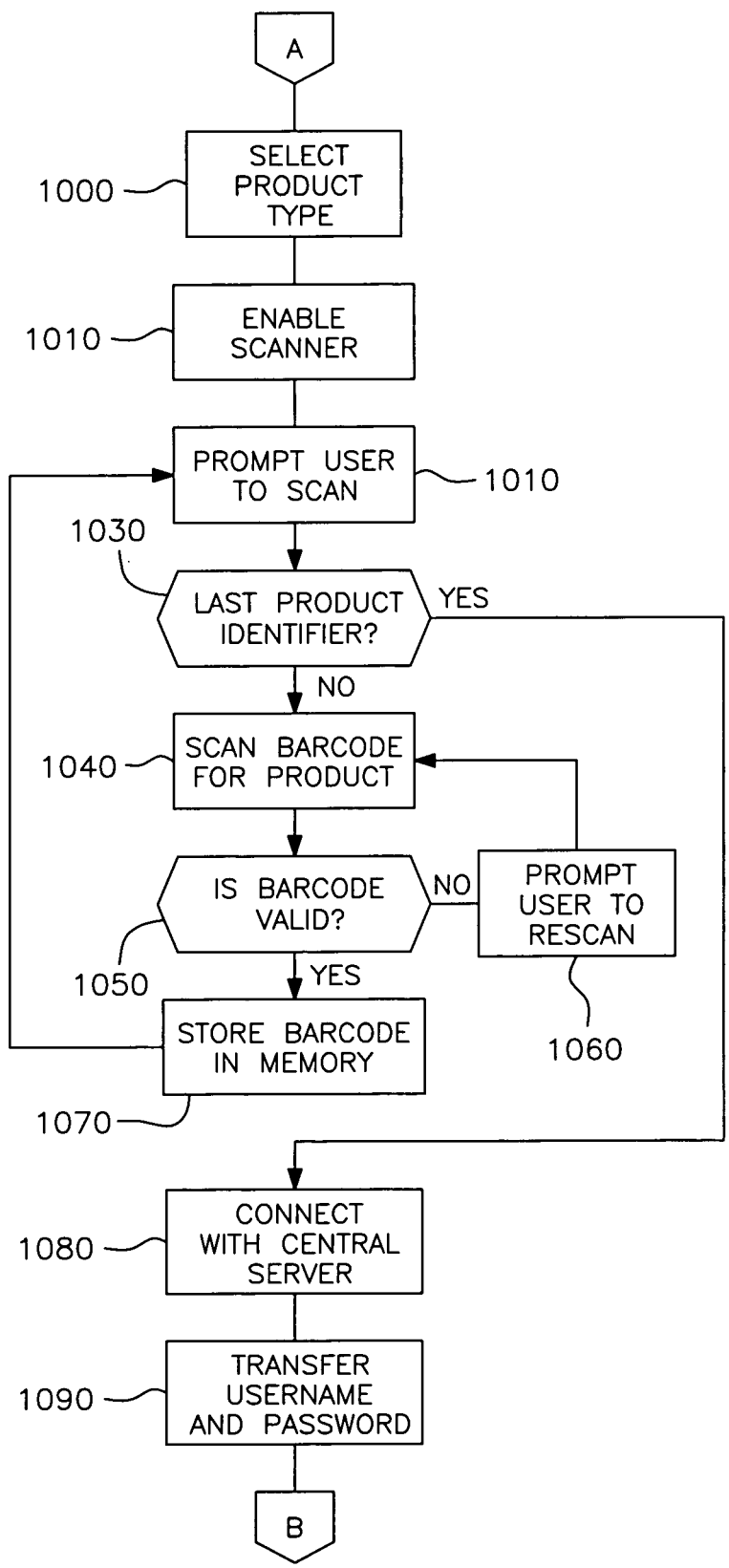

When the enter product identifier function is selected, step 958, the user can select a product type at step 1000, shown in FIG. 11A. Upon selection of a product type, the scanner is enabled at step 1010 and the user is prompted to scan the bar code at step 1020. Step 1030 determines if the product identifier is the last one to be scanned. If it is not the last product identifier, the bar code for the product identifier is scanned at step 1040. The next operation, step 1050, determines if the bar code is valid. If it is valid, processing continues to step 1070 and the scanned unique bar code for the product is stored in the portable unit memory. If the bar code is not valid, the user is prompted to rescan at step 1060. Next, the user is prompted to scan another bar code related to a new product identifier and the process repeats until the last product identifier is scanned. After the last product identifier is scanned, step 1030, the next operation connects the portable unit 40 with the central server 10 at step 1080 and username and password are transferred at step 1090. Although the above description refers to the acquisition of UPIs using the portable unit 40, it is understood that similar processing can be used at the point-of-sale when using the GPI cards 39A for acquisition and transfer of UPIs to CCC 80.

Referring now to FIG. 11B, upon valid verification and authentication, the encrypted product identifier is transferred to the central server 10 at step 1100. Then step 1110 searches product information database 760 for product identifiers transferred. Next, step 1120 checks the product information database 760 to determine whether there is any data on product identifier transferred. If not, then a list of product identifiers without data is created, step 1130, and a message "No data. Rescan in 24 hours" is transferred to the portable unit 40, step 1150. The list is then used to search for the data related to the product identifiers transferred by users. If there is product identifier data, step 1120, such data in any of the fields 763, 764, 765, 766, 767, 768 is retrieved, step 1140. Next the product information data about product identifier is transferred to portable unit 40, step 1160. The data about product identifier is then stored in the portable unit memory and displayed, step 1170.

Figure 11C:
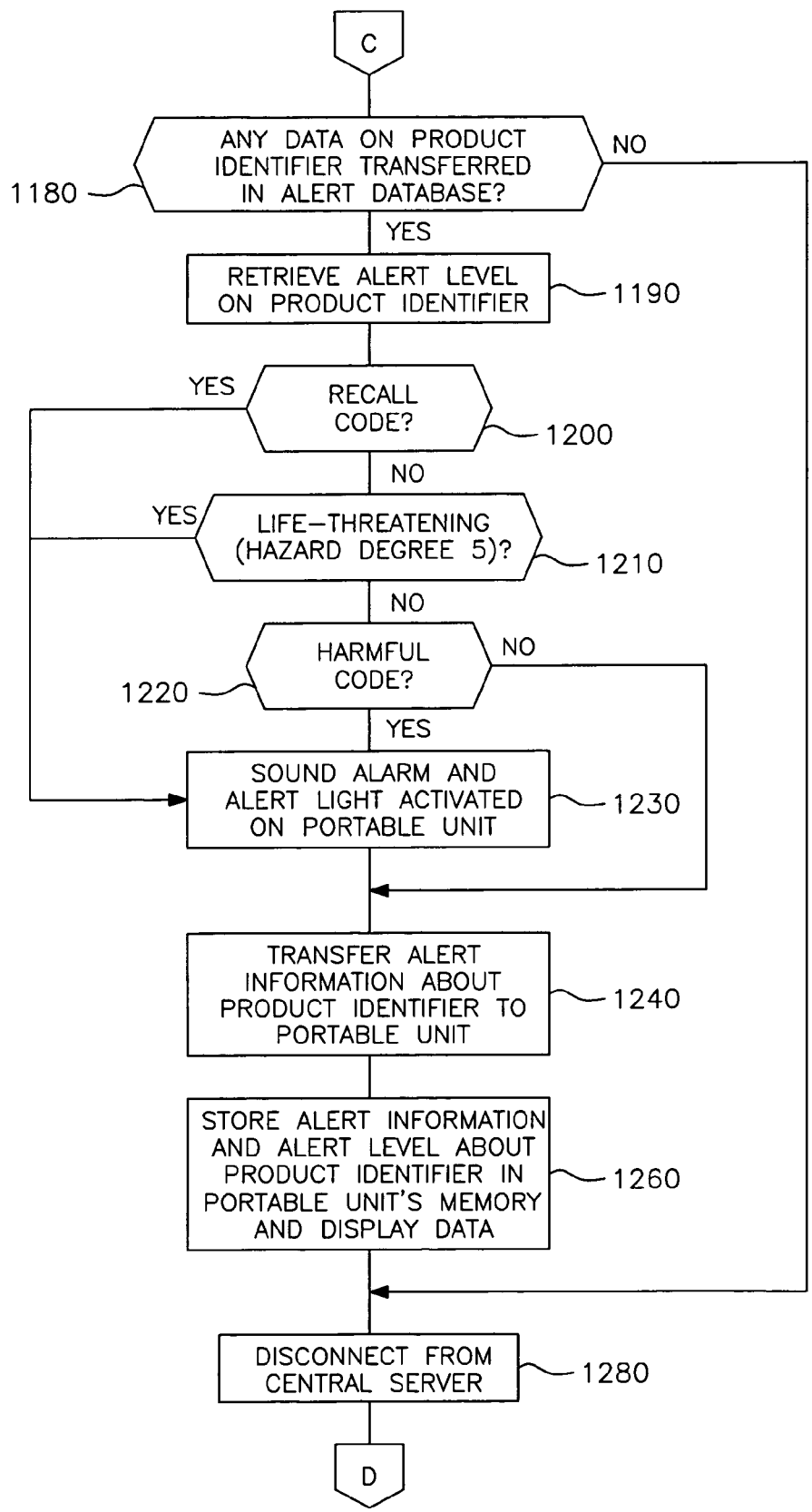

In FIG. 11C, step 1180 determines whether there is any data on the product identifier transferred which is present in the alert database 790. If yes, the alert level 796 on product identifier is retrieved, step 1190; otherwise the process proceeds to step 1280 and disconnect from central server 10. Following retrieval of the alert level, step 1200 determines if the alert level 796 is a recall code. If yes, then an alarm sounds and an alert light is activated in portable unit 40 at step 1230. If the alert level is not a recall code, step 1210 determines if the alert level is a hazard degree 5 (life-threatening). If yes, the process proceeds to step 1230; if no, processing continues to step 1220 to determine whether the alert level is a harmful code. If yes, appropriate audio and visible signs are activated in the portable unit 40 at step 1230. If the alert level is not a harmful code, alert information 794 on product identifier is transferred, step 1240, to portable unit 40. Then alert level 796 and alert information 794 with hazard degree 795 about product identifier are stored in the portable unit memory and displayed, step 1260. At step 1280 the central server 10 is disconnected from portable unit 40. Although in the above description the product information is displayed on the portable unit 40, it is understood that the information can be displayed on other devices such as the point-of-sale terminals, screen of telephones, watches, and the like.

Figure 11D:
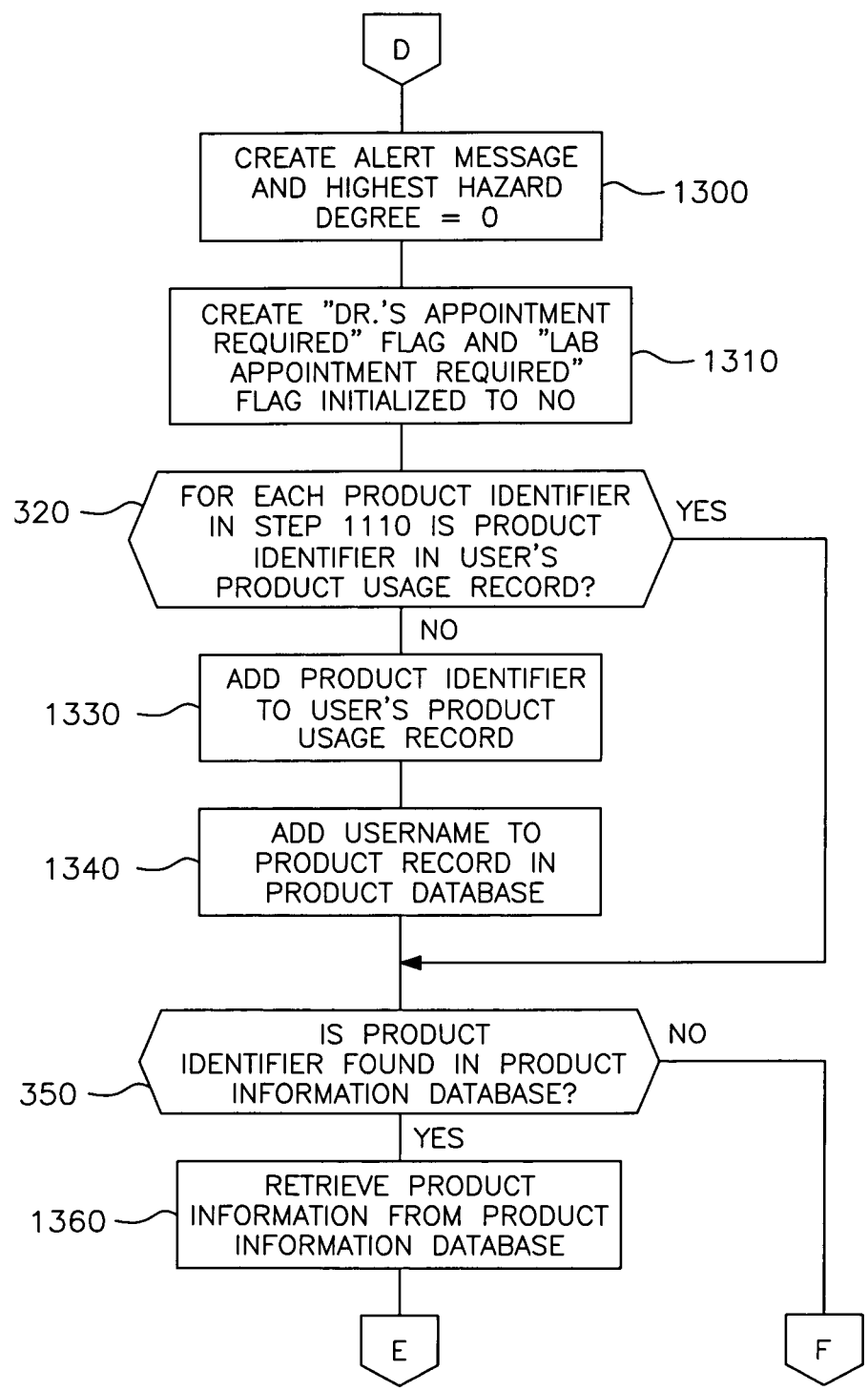

FIG. 11D shows operation continuing to step 1300 to create an alert message and highest hazard degree=0. Next, "doctor's appointment required" and "lab appointment required" flags are created and initialized to NO, step 1310. Then step 1320 determines whether for each product identifier in step 1110 there is product identifier in the user's product usage record in the user's product usage database 740. If not, then the product identifier transferred is added to user's product usage record at step 1330 and the username is added to product record in product database, step 1340. If there is product identifier in user's product usage record, operation proceeds to determine, step 1350, whether there is product identifier in product information database 760. If there is, then step 1360 retrieves product general information 763 from product information database 760 and step 1370 attaches product general information 763 to alert message, as shown in FIG. 11E. If there is no product identifier, or following attachment of the product general information to the alert message, the process proceeds to the step 1380 to determine if for each product identifier in step 1110 there are contraindications 764 listed in its product information record in product information database 760. If yes, contraindications 764 are retrieved, step 1390, from product information record in product information database 760; otherwise the process proceeds to step 1550.

Figure 11F:
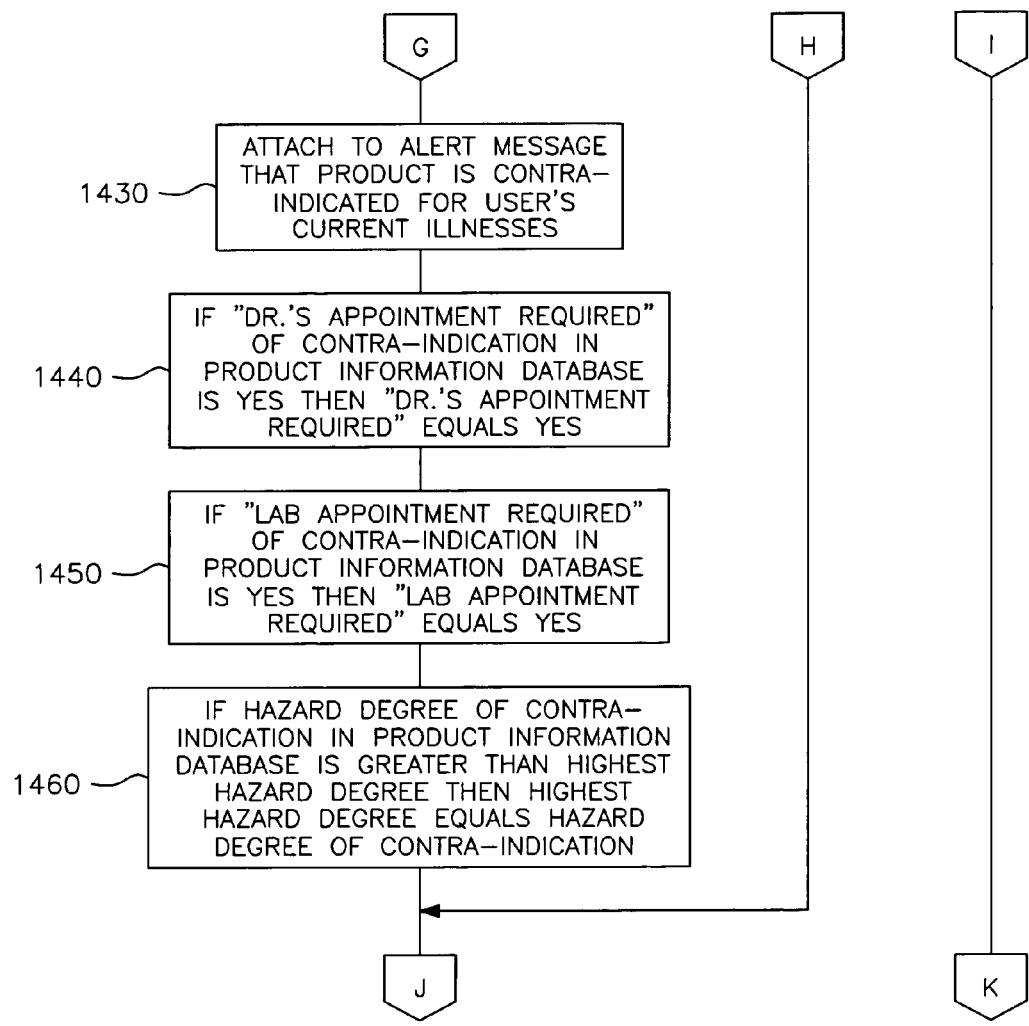

Once contraindications have been retrieved, step 1400 determines for the username in the user's personal information record whether there are current illnesses 716 listed. If yes, then current illnesses 716 are retrieved, step 1420. If not, the process proceeds to step 1480. Once current illnesses have been retrieved, step 1420 then determines whether any of the current illnesses 716 match contraindications 764. If yes, step 1430 attaches to alert message that product is contra-indicated for user's current illnesses 716, as shown in FIG. 11F. Processing then continues to step 1440, in which if "doctor's appointment required" 766 of contraindication 764 is "Yes" then "doctor's appointment required" equals Yes. Next, step 1450, if "laboratory appointment required" 767 equals "Yes"

then "lab appointment required" equals Yes. At step 1460, if hazard degree 765 of contraindication 764 in product information database 760 is greater than highest hazard degree, then highest hazard degree equals hazard degree of contraindication.

Figure 11G:
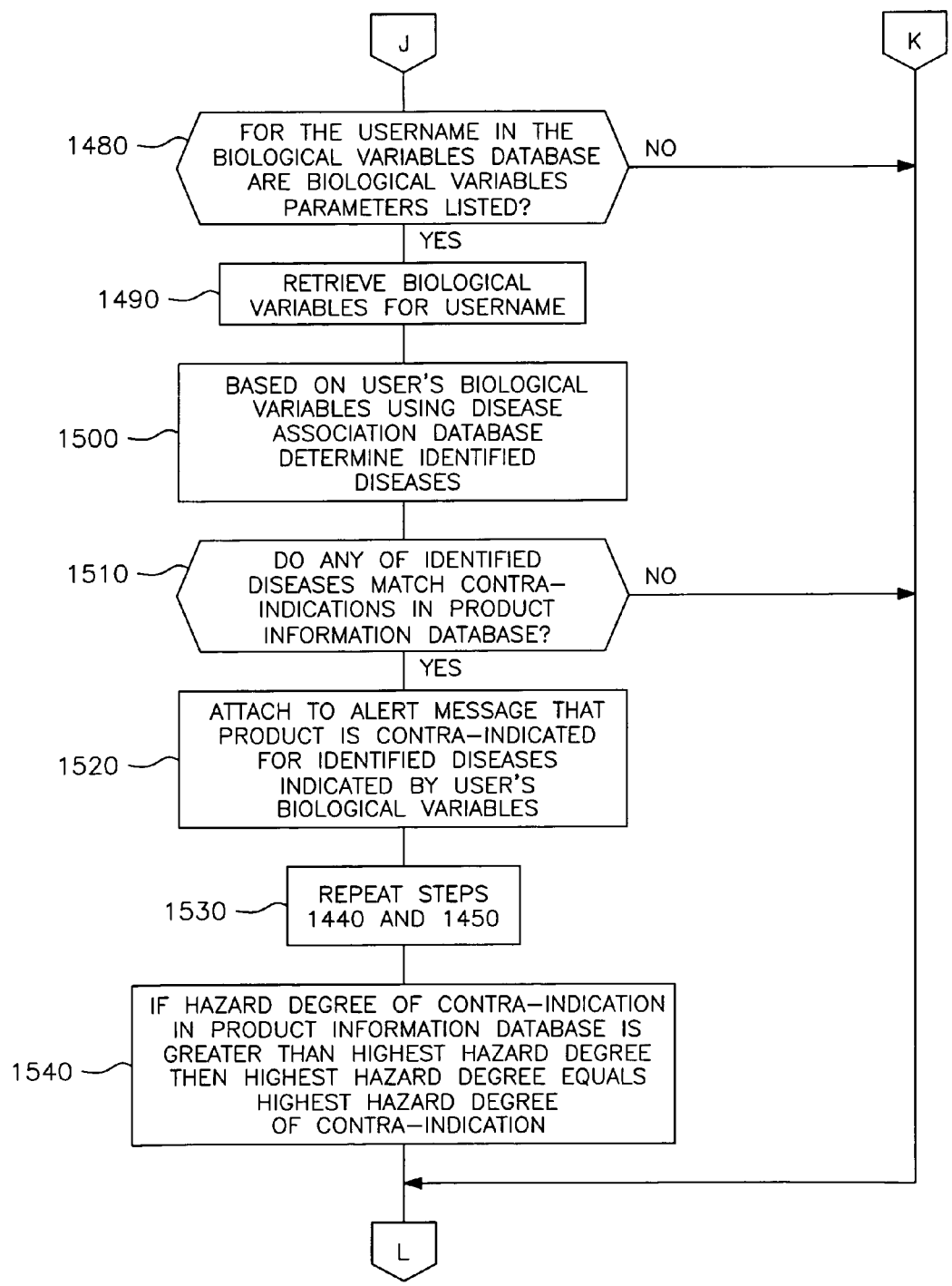

Referring now to FIG. 11G, step 1480 determines whether for the username 771 in the biological variables database 770 there are biological variables parameters 774 listed. If yes, step 1490 retrieves biological variables parameters 774, values 775 and time/date 776 from biological variables database 770. If no, the process proceeds to step 1550.

Once the biological data has been retrieved, identified diseases are determined, step 1500, based on user's biological variables parameters 774 and values 775 using disease association database 750. Step 1510 then determines if any of the identified diseases 752 match contraindication 764. If no, the process proceeds to step 1550. If yes, step 1520 attaches to alert message that product is contraindicated for identified diseases 752 indicated according to the user's biological variable values. Next, step 1530, steps 1440 and 1450 are repeated to determine if doctor's appointment or lab appointment is required according to contraindication 764 information in product information database 760. Then at step 1540, if hazard degree of contraindication in product information database is greater than highest hazard degree then highest hazard degree, equals highest hazard degree of contraindication.

Figure 11H:
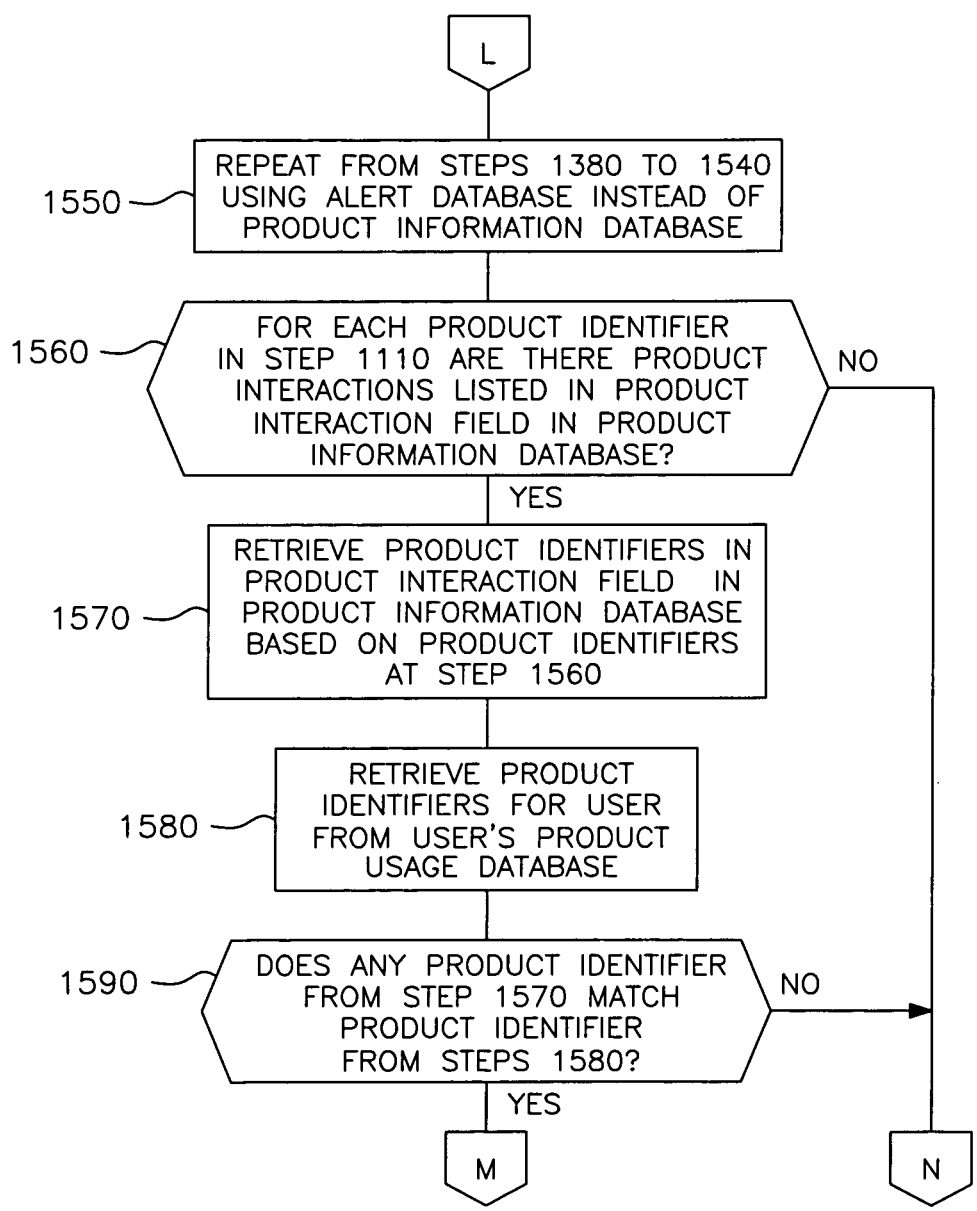
Figure 11I:
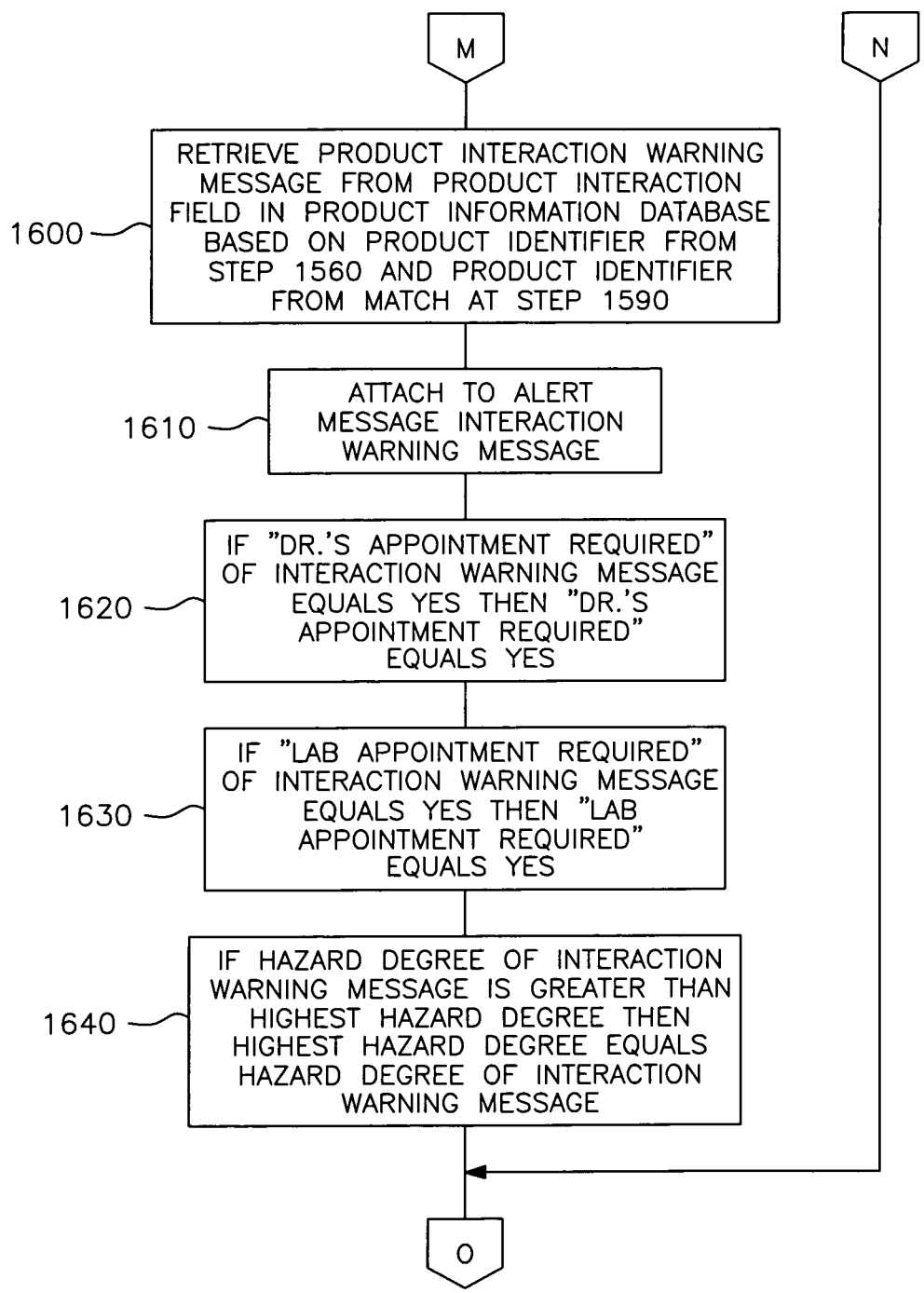

Referring now to FIG. 11H, step 1550 repeats the steps of 1380 to 1540 using alert database 790 instead of product information database 760. The routine allows the identification of the hazard degree, need for doctor or lab appointment according to the contraindication in both databases, product information database 760 and alert database 790. For instance, in case the user is utilizing a product and then later changes occur in the user's health status according to the user's biological variables, the GPI system 1 identifies the contraindication with its hazard degree and the need for doctor or laboratory evaluation according to the information in the product information database 760. In case the use of the product is contraindicated according to the health status of the user, the GPI system 1 informs the user about the hazard and the action that the user should take.

The method continues with step 1560 which, determines whether, for each product identifier in step 1110, there are product interactions listed in product interaction field 768 in product information database 760. If yes, step 1570 retrieves product identifiers in product interaction field 768 in product information database 760 based on product identifiers at step 1560, identifying thus known product interactions concerning the products which were transferred. If not, processing continues with step 1660.

After product identifiers in product interaction filed have been retrieved, step 1580 retrieves product identifiers for the user from the user's product usage database 740 thus identifying the products currently being used. Step 1590 then determines whether any product identifier from step 1570 matches product identifier from step 1580 in order to determine product-product interaction or, more precisely, interaction between products transferred and products being used. If there is no match, now referring to FIGS. 11I and 11J, processing proceeds to step 1660. For example as described above, the heart rate and rhythm of a patient who has an implanted pacemaker is being monitored and the data is sent to the GPI server 10 via the Internet. In this case the HMD 50 consists of a heart monitoring device used at home with continuous 24 hour monitoring. If momentarily the heart rate slows down, the information is identified as bradicardia and if the user also has in his/her database a product identifier for verapamil and furthermore a product identifier for grapefruit juice, then the system identifies the product as interacting with verapamil as previously described, in which grapefruit juice could be potentially increasing the effect of verapamil which in consequence increases its heart blocking properties which ultimately is responsible for the slow heart rate transferred. In this case a simple change in the diet and/or other drug can fix the problem. Using the prior art, most likely the doctor may have a tendency to consider a malfunctioning pacemaker or interaction of the pacemaker with verapamil and then great effort, time and expense is used in checking and fixing the pacemaker and/or changing the drug regimen, not knowing that potentially a small change in diet could have fixed the problem.

Referring again to FIG. 11I, the next step 1600 retrieves product interaction warning message 833 from product interaction field 768 in product information database 760 based on product identifier from step 1560 and product identifier from match at step 1590, thus precisely informing the user about the potential injury or illness caused by the concomitant use of products acquired or stored for the user. Then, step 1610, the interaction warning message 833 is attached to alert message. Next, at step 1620 if "doctor's appointment required" 835 of interaction warning message 833 equals "yes" then "doctor's appointment required" equals "yes". At step 1630 if "laboratory appointment required" 836 of interaction warning message 833 equals "yes" then "laboratory appointment required" equals "yes". Next, at step 1640 if hazard degree 834 of interaction warning message 833 is greater than highest hazard degree, then highest hazard degree equals hazard degree of interaction warning message.

Figure 11J:
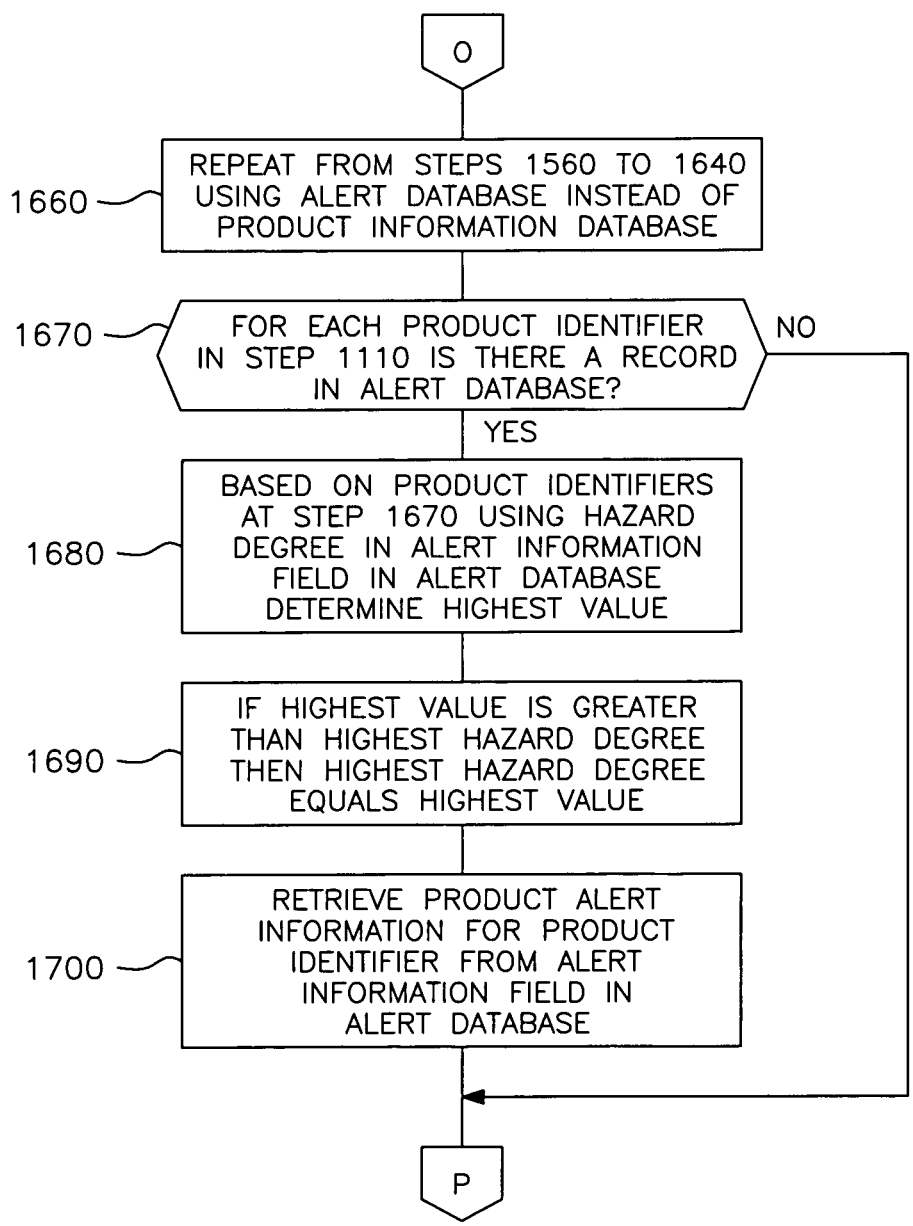

Referring now to FIG. 11J, step 1660 then repeats the steps of 1560 to 1640 using alert database 790 instead of product information database 760. According to the exemplary embodiment, the product information database 760 provided information derived from the manufacturer indicating that product UPI 0031, for instance a pain killer (aspirin), interacts with drug M 831 and food F 832 while the alert database 790 provided information derived from post-market surveillance by the FDA 130 indicating new interactions that were later discovered after the drug had been on the market; the newly discovered interactions include drug A 810, drug B 811, food E 812 and cosmetic X 813. The user is then informed about potential interactions involving established information as well as new information acquired during post-market surveillance, for example. The processing then continues to address another important area of recalled products and harmful products according to information provided by the RIS 60.

Step 1670 determines whether, for each product identifier in step 1110, there is a record in alert database 790. If not, processing proceeds to step 1710. Otherwise, the highest hazard degree value is determined, step 1680, based on product identifiers at step 1670 using hazard degree 795 in alert information field 794 in alert database 790. Then if the highest value is greater than the highest hazard degree, then highest hazard degree equals hazard degree, step 1690, thus informing of the user the highest hazard degree related to a recall and the information related to the recall. Step 1700 then retrieves product alert information for product identifier from alert information field 794 in alert database 790.

Figure 11K:
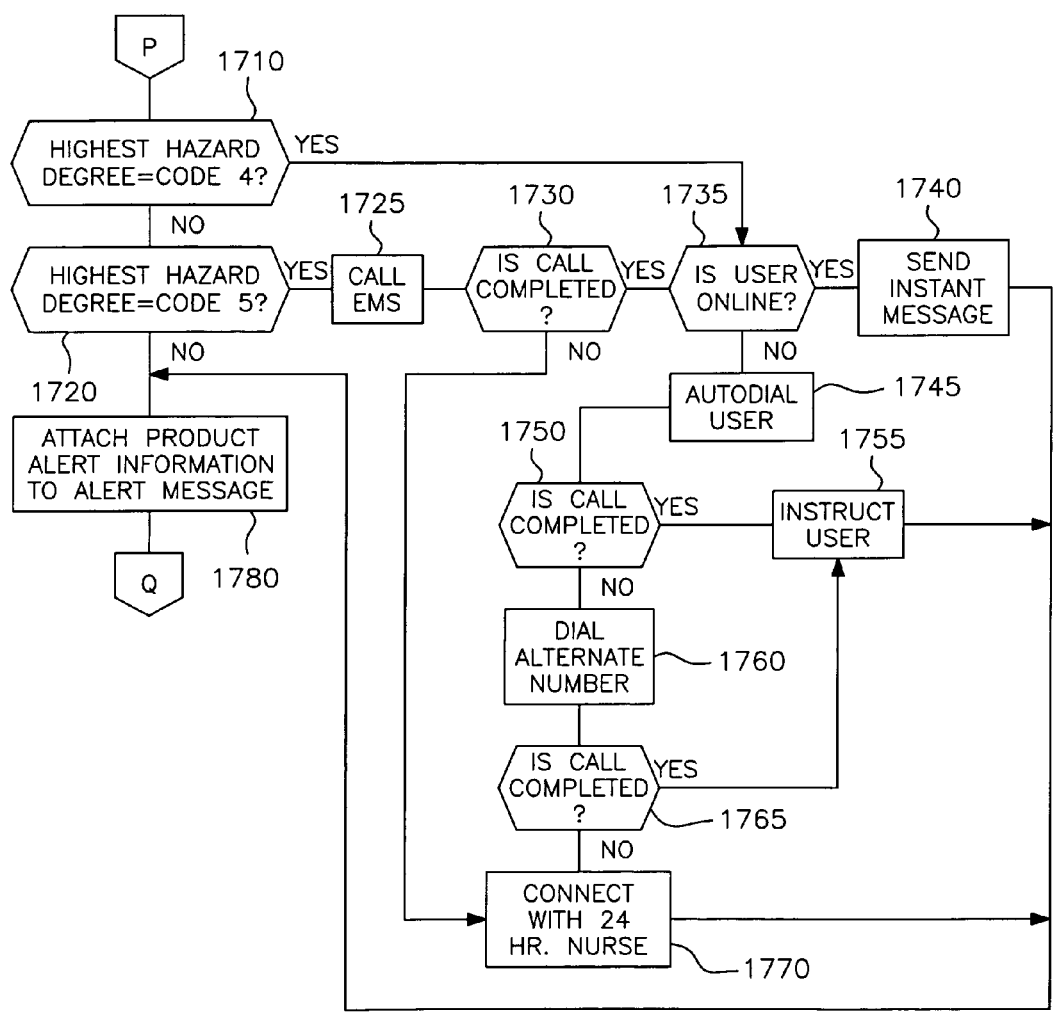

Upon that, and referring now to FIG. 11K, processing at step 1710 determines if highest hazard degree equals code 4. If yes, then step 1735 determines if the user is online and, if so, an instant message is sent to the user, step 1740. If the highest hazard degree is not equal to code 4, step 1720 determines if highest hazard degree equals code 5. If not, the process proceeds to step 1780; otherwise at step 1725 EMS or ambulance service 72 is called and step 1730 determines if the call is completed. If yes, processing continues with step 1735 to determine if the user is online and, if the user is online, an instant message is sent, step 1740. If the call is not completed, then step 1770 connects with a 24-hour nurse or auto dial 911 if in the USA. After an instant message is sent, product alert information 794 is attached to alert message, step 1780.

If the user is not online, in order for critical and life-saving information to reach the user, step 1745 autodials the user. Step 1750 then determines if the call is completed. If yes, step 1755 instructs the user; otherwise an alternate number is dialed, step 1760, according to information from the user's personal information database 700. Next, step 1765 determines if the call is completed for alternate number. If yes, processing proceeds with step 1755 and the user is instructed; otherwise step 1770 connects with a 24-hour nurse and then proceeds to step 1780. After instructing the user, processing continues, step 1780, with the product alert information 794 being attached to alert message.

Figure 11L:
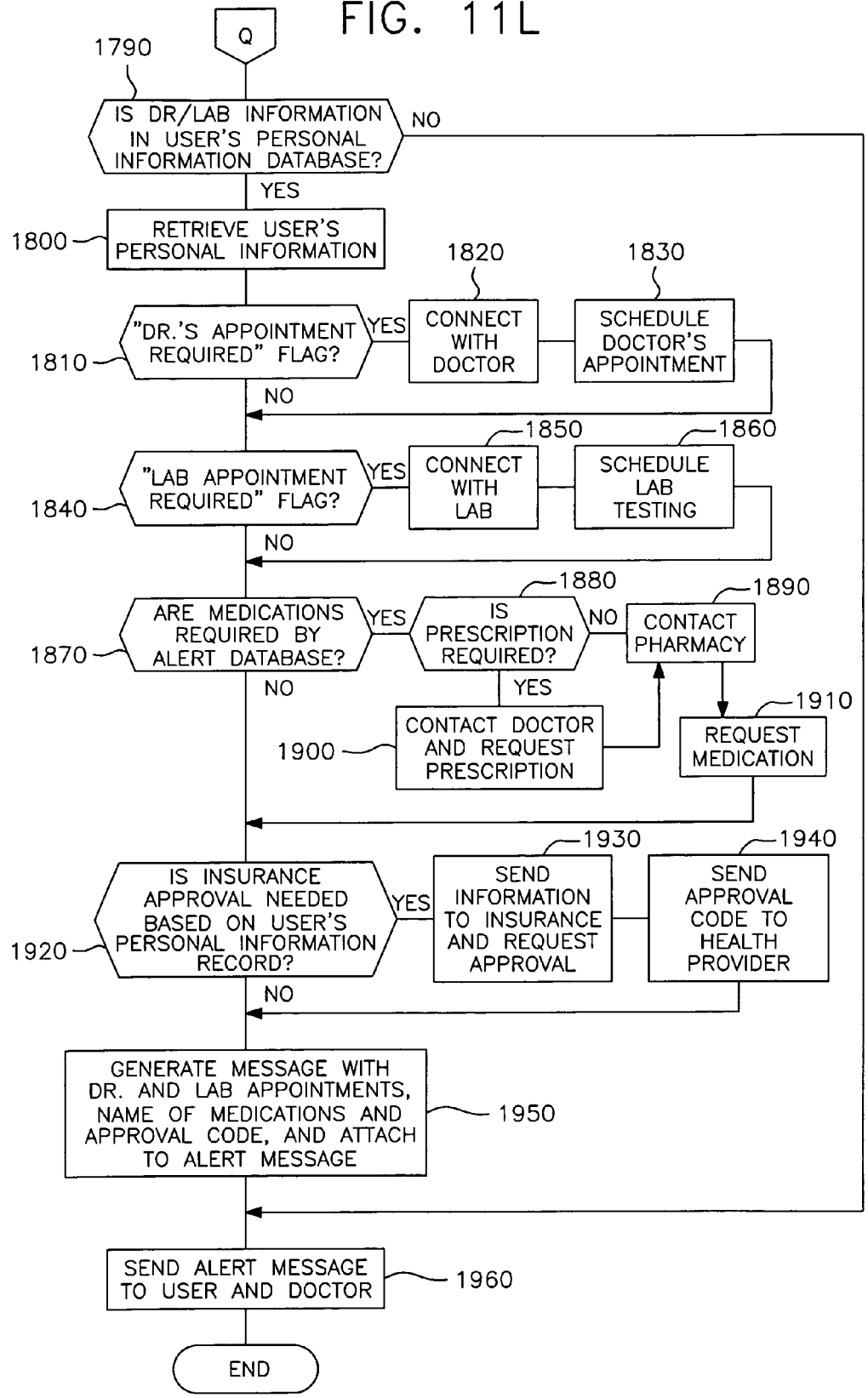

Referring now to FIG. 11L, step 1790 determines whether there is doctor information, 712 or laboratory information 713 or pharmacy information 714 in the user's personal information database 700. If yes, step 1800 retrieves user's personal information; otherwise the operation proceeds to step 1960. Once the user's personal information has been retrieved, "doctor's appointment required" flag is tested at step 1810. If the flag is set, step 1820 connects with doctor and an appointment is scheduled, step 1830. If the flag is not set, the process determines, step 1840, whether the "laboratory appointment required" flag is set. If yes, step 1850 connects with laboratory and an appointment is scheduled, step 1860. If the laboratory flag is not set, step 1870 determines if medications are required 802 according to alert database 790. If not, processing proceeds to step 1920. If medications are required, step 1880 determines if a prescription is required 803. If yes, doctor is contacted and prescription is requested, step 1900, and the pharmacy is contacted, step 1890. If prescription is not required, then pharmacy is contacted at step 1890 with medication requested at step 1910.

Step 1920 determines if insurance approval 715 is needed based on the user's personal information record. If not, processing continues with step 1950. If approval is required, step 1930 sends information to the insurance company and requests approval according to insurance information 715 in the user's personal information database 700. Then if for example a drug as Dexfenfluramine (Redux®) as previously described was used and since the recommendations by the FDA include heart evaluation by a doctor, then the user of the UPI Dexfenfluramine (Redux®) is automatically scheduled for an appointment with a suitable doctor in the user's domicile area. Then if for example a drug as Dexfenfluramine (Redux®) was used and since the recommendations by the FDA include laboratory evaluation with an echocardiogram, then the user of the UPI Dexfenfluramine (Redux®) is automatically scheduled for an echocardiogram in a suitable laboratory or medical institution in the user's domicile area according to the user's record in the user's personal information database 700. After the laboratory tests are performed, the results of the laboratory tests are electronically sent to the GPI server 10 and the data is stored in the biological variables database 770 for the user who underwent the laboratory evaluation. If a prescription is needed, as recommended by, for instance, an RIS 60 such as FDA 130, then the doctor is contacted and a prescription sent to a pharmacy in the user's domicile area. If there is need for insurance approval according to the user's record, then the approval code is acquired, step 1940, and transferred to the various health care providers. Next, step 1950 generates a message with doctor appointment and laboratory appointment, approval code from insurance, name of medications 802 and directions, alternative medications, and instructions 804 and attaches this information to alert message. Next, step 1960 sends alert message to user and doctor, and processing ends.

Returning to FIG. 10, the transfer of user's biological variable to central server 10 occurs once the password is validated. Upon that, a Select Function screen is displayed at step 952, allowing the user to select the desired function.

After selecting enter biological variable 962, processing continues with step 965. Biological variables can be acquired in various ways as previously described. After acquisition of the biological variable, step 970 determines if it is the last biological variable. If yes, then connection with central server 10 is established at step 985. If it is not the last variable, processing continues with selection of a biological variable, step 975, and entry of biological variable at step 980. Next, step 965 acquires biological variable and, if it is the last biological variable, connects with central server 10 at step 985.

Upon that, and now referring to FIG. 12A, step 2000 transfers parameters 774 (for example: eye pressure, blood pressure, heart rhythm, blood analytes such as glucose and cholesterol, and the like) and values 775 of biological variables to central server 10. If continuous heart rhythm or continuous eye pressure is being transferred, in an alternative embodiment, the central server 10 for continuous mode receives the information and is set up to send an alert message according to specific criteria such as peak in eye pressure above 30 or heart rate faster than 100 or slower than 50 and the like. In the current embodiment, after parameters 774 and values 775 are transferred, the portable unit 40 disconnects from the central server 10 at step 2010. Next, step 2020 creates an alert message. Step 2030 then retrieves parameters 774 and values 775 for the biological variables for username 771 from biological variables database 770. Next, step 2040 determines if the transferred biological variable parameter 774 is in biological variable record for user in biological variables database 770. If not, step 2050 adds the biological variable parameter for user. If the variable is in the record, processing proceeds to step 2060 and adds time/date stamp to field 776. Next biological variables database is updated to reflect the new data transferred, step 2070, and the new values 775 transferred are attached to alert message, step 2080.

Referring now to FIG. 12B, step 2090 retrieves from user's personal information database 700 the normal range of biological variables 717 for the user, such that the information is precisely crafted according to the individual health status and needs of each individual user. Step 2100 then determines if transferred biological variables are within the normal range. If yes, step 2110 attaches a message indicating that biological variable values are normal to the alert message and proceeds to step 2370.

If the values are not in the normal range, the timely monitoring period 718 is retrieved, step 2120, from user's personal information database 700. Next, step 2130 retrieves from biological variable database 770 the time/date 776 the biological variable was last transferred. Then, step 2140 determines if today's date minus date of last transferred biological variable is less than timely monitoring period. If yes, step 2150 attaches a message indicating the value abnormal but timely monitored to the alert message, and then continues to step 2260. If the difference is greater than the timely period, step 2160 attaches a user instruction on timely monitoring to the alert message.

Now referring to FIG. 12C, step 2170 retrieves from user's personal information database 700 hazard associated with untimely transmission 719 and attaches, step 2180, hazard to alert message. Step 2190 then retrieves from user personal information database 700 the message indicating "inform doctor of abnormal value untimely transmitted" 720. Then processing proceeds to test "inform doctor of abnormal value untimely transmitted", step 2200. If doctor is not to be informed, then operation proceeds to step 2260. If doctor is to be informed, the doctor is contacted, step 2210, and priority appointment scheduled, step 2220. This previous embodiment relates to the timely intervention and appointments scheduling according to the transmission of biological variables and products being used. Patients sometimes come to their doctor at a critical stage of their medical condition in which sometimes irreversible damage or life-threatening complications have already occurred. It is very difficult to evaluate with certainty when an appointment is needed for a certain patient or certain condition. Sometimes if the patient had come just a few days earlier, a life could have been saved or irreversible and costly complications avoided. For instance patients with history of renal failure or heart failure need a very strict control of their body weight to avoid potentially fatal complications such as acute heart failure and/or pulmonary edema. Patients may call the doctor's office for an appointment, but most of the time if they do not have any clearly warning symptoms, the appointment is scheduled according to the openings in the doctor's schedule or according to a pre-set time period for instance every 4 months. Unfortunately in either case as the appointment is scheduled randomly, when the patient comes to the doctor's office complications could already have occurred. According to an exemplary embodiment an electronic scale or any other medical monitoring device transfers the information about the patient's weight which is evaluated against values which are considered safe for the patient. If the monitored weight is not within normal limits for the patient and timely transferred, a priority appointment can be scheduled before serious complications occur.

Figure 12D:
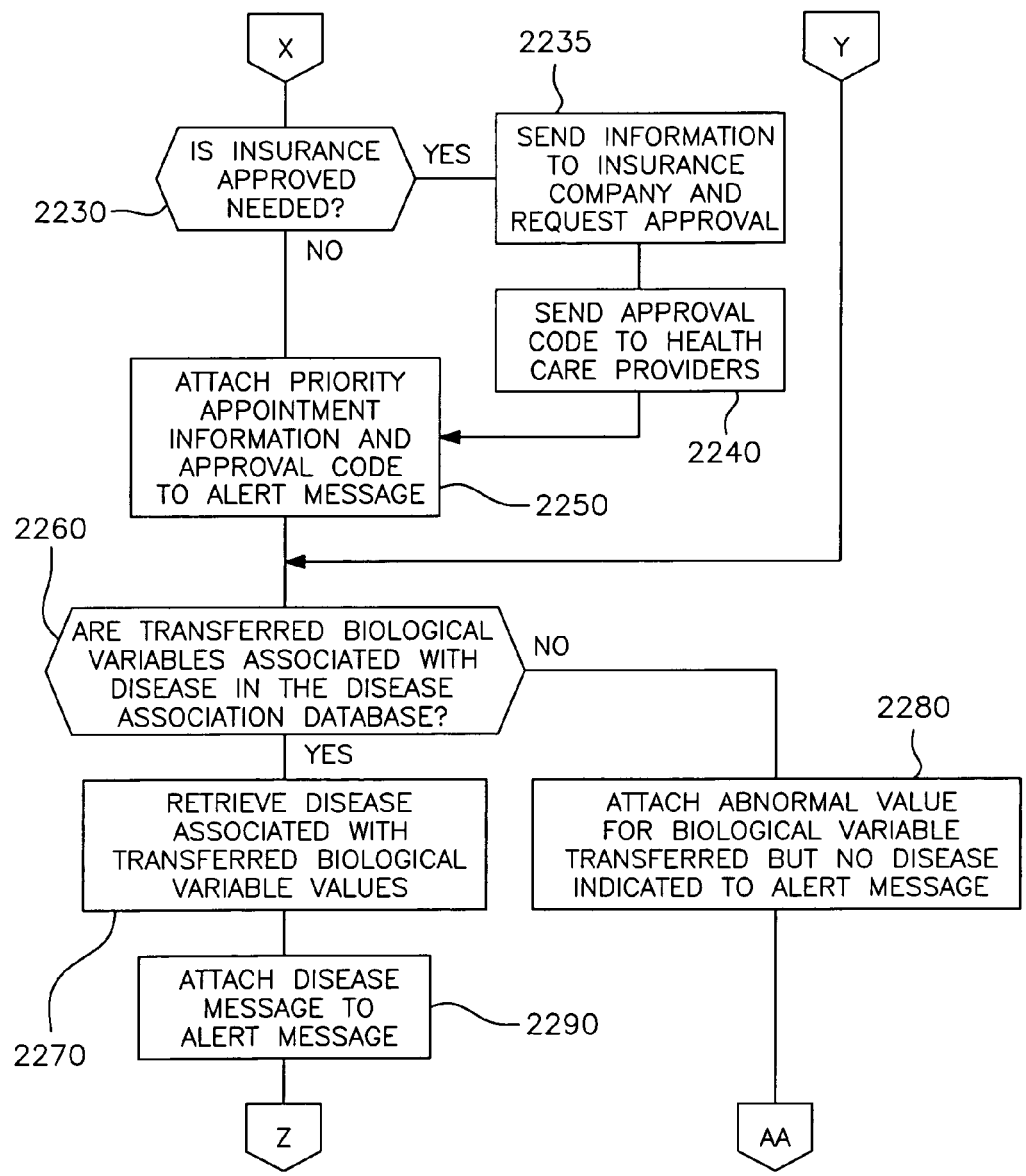

Next, processing continues to evaluate the need for insurance approval. Referring now to FIG. 12D, step 2230 determines if insurance approval is needed according to record 715. If yes, step 2235 sends information to insurance company and requests approval. Next the approval code is sent to health care provider for the user, step 2240. If approval is not needed, step 2250 attaches priority appointment and approval code to alert message. Next, step 2260 determines if transferred biological variable values are associated with disease 752 in the disease association database 750. If not, step 2280 attaches to alert message "abnormal value for biological variable transferred but no disease indicated" and then proceeds to step 2370. If transferred values are associated with a disease, then step 2270 retrieves disease 752 associated with transferred biological variable values 751. Then, step 2290 attaches disease message 751, 752 to alert message.

Figure 12E:
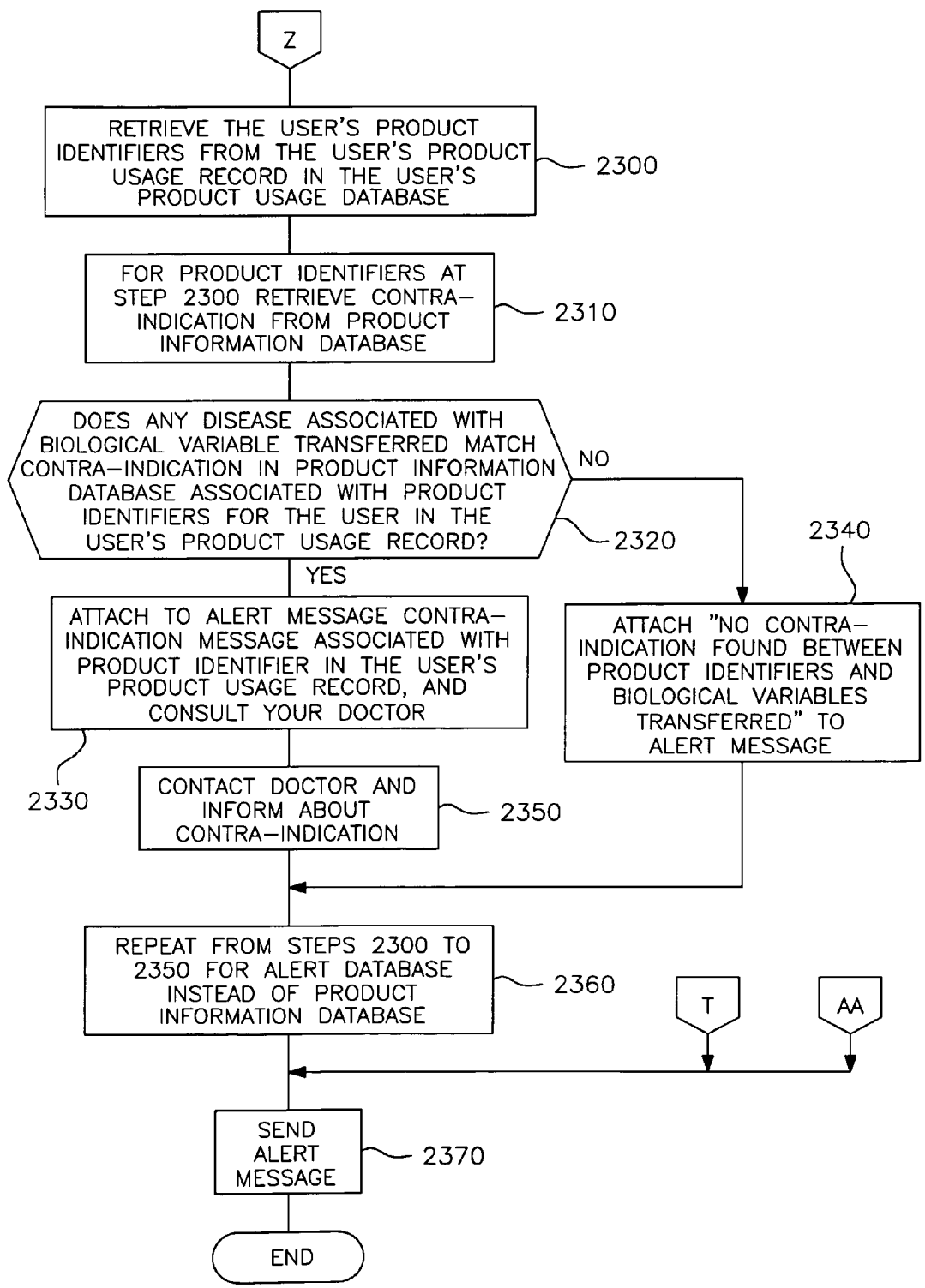

Now referring to FIG. 12E, step 2300 retrieves the user's product identifiers 749 from the user's product usage record in the user's product usage database 740. At step 2310, contraindications 764 from product information database 760 are retrieved for product identifiers at step 2300. Next, step 2320 determines whether any disease 752 associated with biological variables transferred matches contraindication 764 in product information database 760 associated with product identifiers 749 for the user in the user's product usage record.

If yes, then step 2330 attaches to alert message "contraindication associated with product identifier in the user's product usage record", and "consult your doctor". Processing thus precisely determines interaction between unique products used by each individual user and health status of each individual user. Next, step 2350 contacts doctor and informs about contraindication. This message to the doctor allows the practitioner to evaluate the interaction between a drug prescribed and a change in the health status of the patient who is now at risk of harm by using the drug. If there are no diseases associated with the transferred variable, then step 2340 attaches to alert message "no contraindication found between product identifiers and biological variables". Next, processing addresses information related to contraindication received from RIS 60 such as government agencies, with the information stored in alert database 790. In accordance, step 2360 repeats the steps of 2300 to 2350 for the alert database 790 instead of product information database 760. Next, an alert message is sent, step 2370, with the information acquired, to the user and operation ends.

Figure 13B:
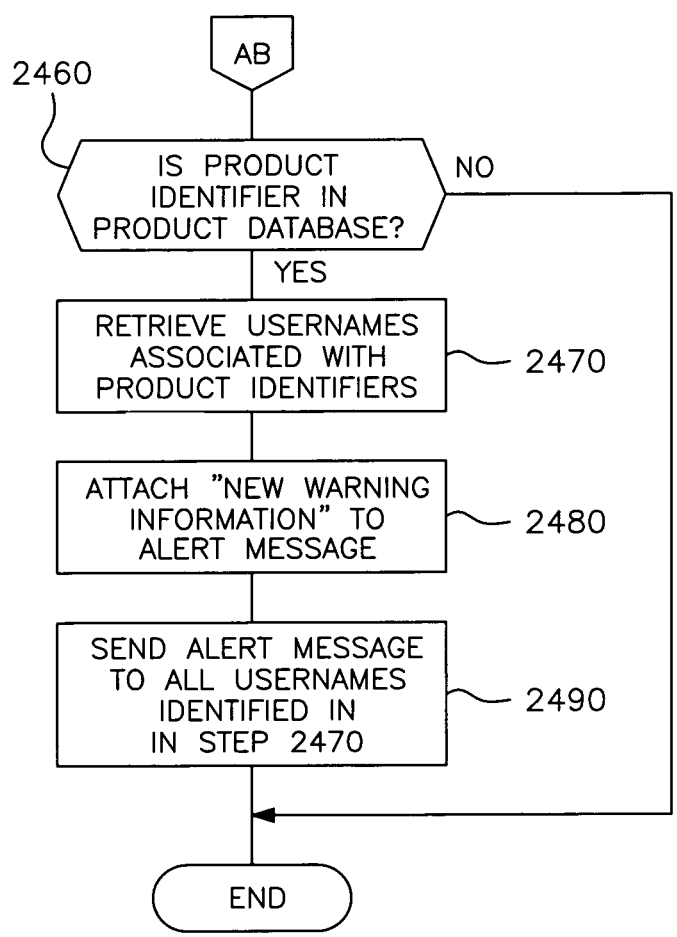

FIGS. 13A and 13B depict the flow diagram concerning acquisition of data from the RIS 60. In this exemplary embodiment, a government remote computer transfers information to alert database 790. At step 2400 the remote computer sends message to central server 10 that updated information is available. Next, after appropriate identification and authentication, central server 10 establishes connection with remote computer, step 2410. At step 2420, the remote computer 60 transfers product identifiers with associated "new warning information," which can be a recall warning, harmful warning levels 1 to 5, or a beneficial notice according to the new data acquired by the government agency. Step 2430 then stores product identifiers and "new warning information" in alert database 790. Next step 2440 disconnects remote computer from central server 10. Step 2450 then creates alert message. Step 2460 then determines if product identifiers transferred are in the product database 730. If not, the operation ends. If product identifier is in product database, step 2470 retrieves usernames associated with product identifiers. Next step 2480 attaches "new warning information" to alert message. Step 2490 then sends alert message to all usernames identified at step 2470, and operation ends.

Figure 14B:
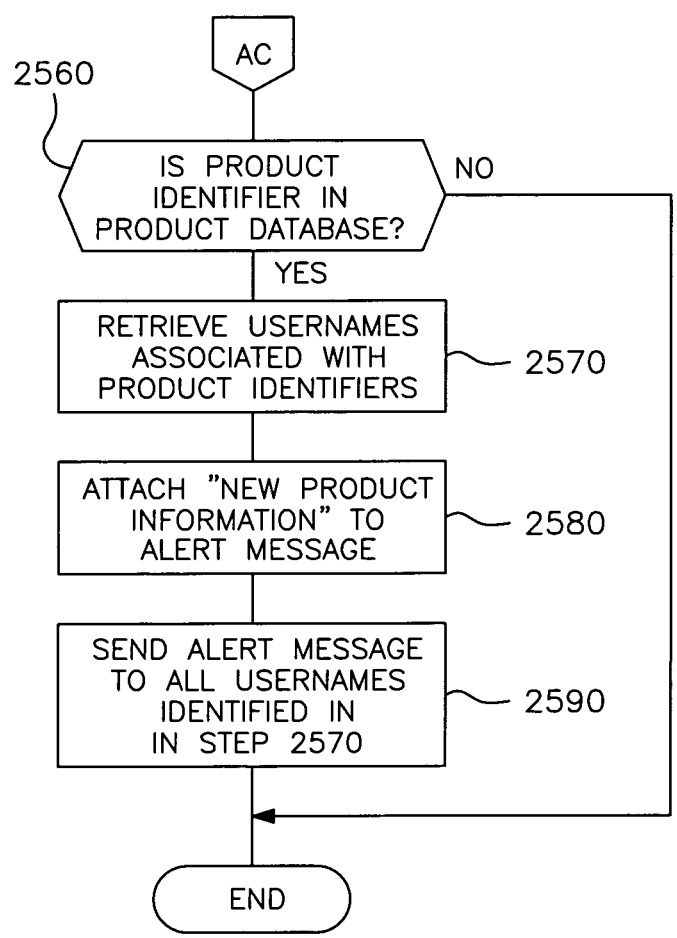
Figure 15B:
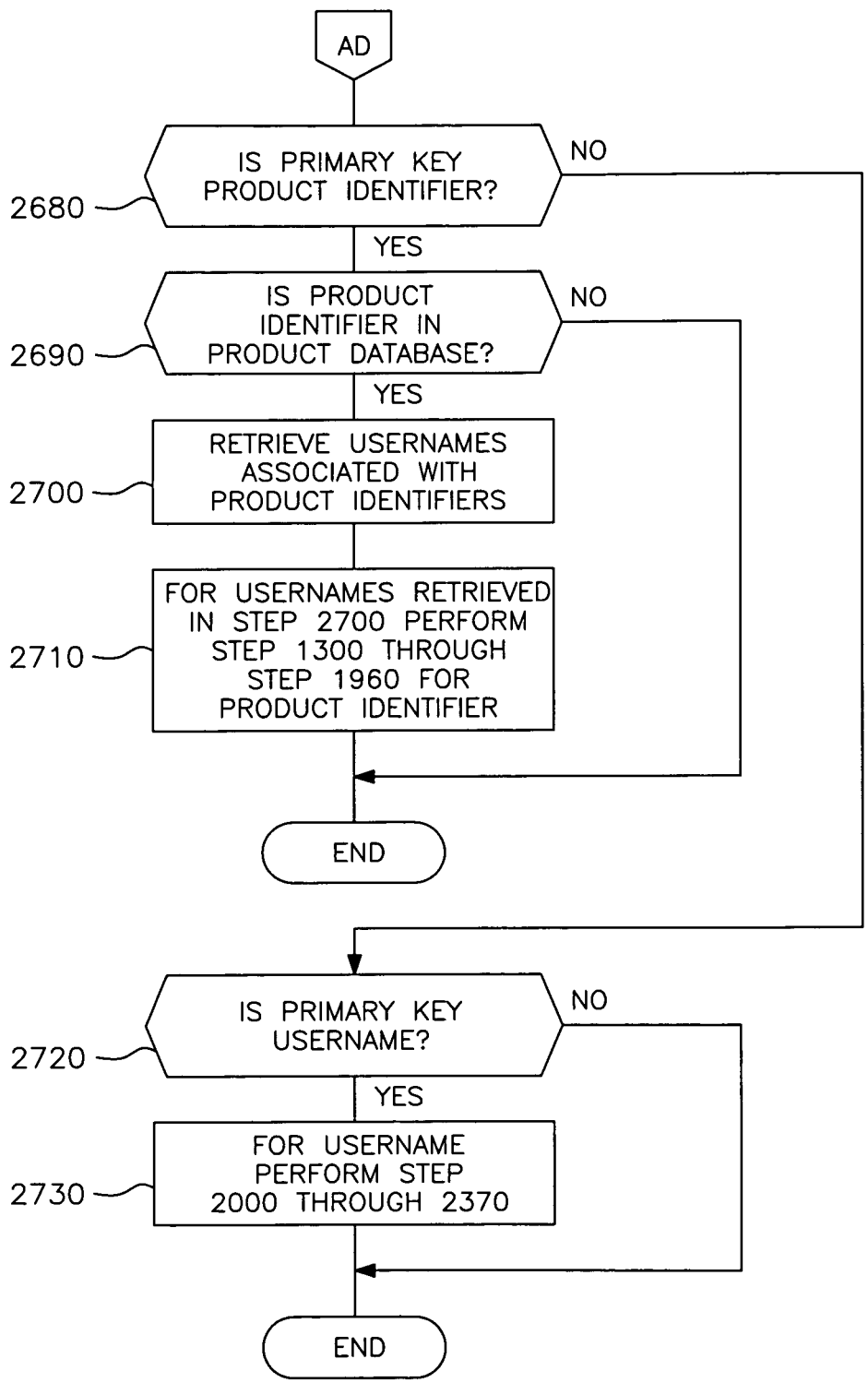

Referring now to FIGS. 14A and 14B, a similar processing as above is used, but now using the manufacturer 148 as remote computer updating product information in the product information database 760. In accordance, at step 2500 remote manufacturer computer 148 sends message to central server 10 that updated information is available. Next, at step 2510 central server 10 establishes connection with remote manufacturer computer 148. At step 2520 remote manufacturer computer 148 then sends product identifiers with associated "new product information". Next, step 2530 stores product identifiers and "new product information" in product information database 760. Next, step 2540 disconnects central server 10 from remote computer 148 and step 2550 creates alert message. Next, step 2560 determines if product identifier is in the product database 730. If not, the operation ends. If the product identifier is in the database 730, step 2570 retrieves usernames associated with product identifiers. Then step 2580 attaches "new product information" to alert message and step 2590 sends alert message to all usernames identified at step 2570, and operation ends.

For every product identifier transferred by a user, the central server 10 provides the information related to the product. When the central server 10 receives for the first time a certain product identifier from a user, the central server 10 may not have data on the product identifier transferred and will ask the user to rescan the product in 24 hours. The central server 10 then, in the next 24 hours, searches the RIS 60 for the information related to the product identifier. In accordance, and now referring to FIGS. 15A and 15B, at step 2600 central server 10 initiates connection with a remote computer 60, which can be a government agency, the manufacturer, a medical institution, a research facility, and the like. Next, step 2610 connects the central server 10 to the remote computer 60. At step 2620 the central server 10 accesses the remote computer database. Step 2630 then determines whether there is a primary key in the remote computer database. If not, the process proceeds with step 2670 and disconnection from the remote computer 60. If there is a primary key, the information associated with the primary key is retrieved, step 2640. Step 2650 then stores the retrieved information in the database of central server 10. Next, step 2660 generates a list of updated information on the primary keys and disconnects from remote computer at step 2670. Step 2680 then determines if the primary key is product identifier. If not, the process proceeds with step 2720 to determine if the primary key is a username and, if not, the operation ends. If the primary key is a username, for that username step 2730 performs step 2000 through 2370, and the operation ends.

If primary key is a product identifier, then step 2690 determines if product identifier is in product database 730. If not, the operation ends. If the product identifier is in the product database, step 2700 retrieves usernames associated with product identifiers. Next, step 2710, for usernames retrieved in step 2700, steps 1300 through 1960 are performed for product identifier, and processing ends.

Figure 16:
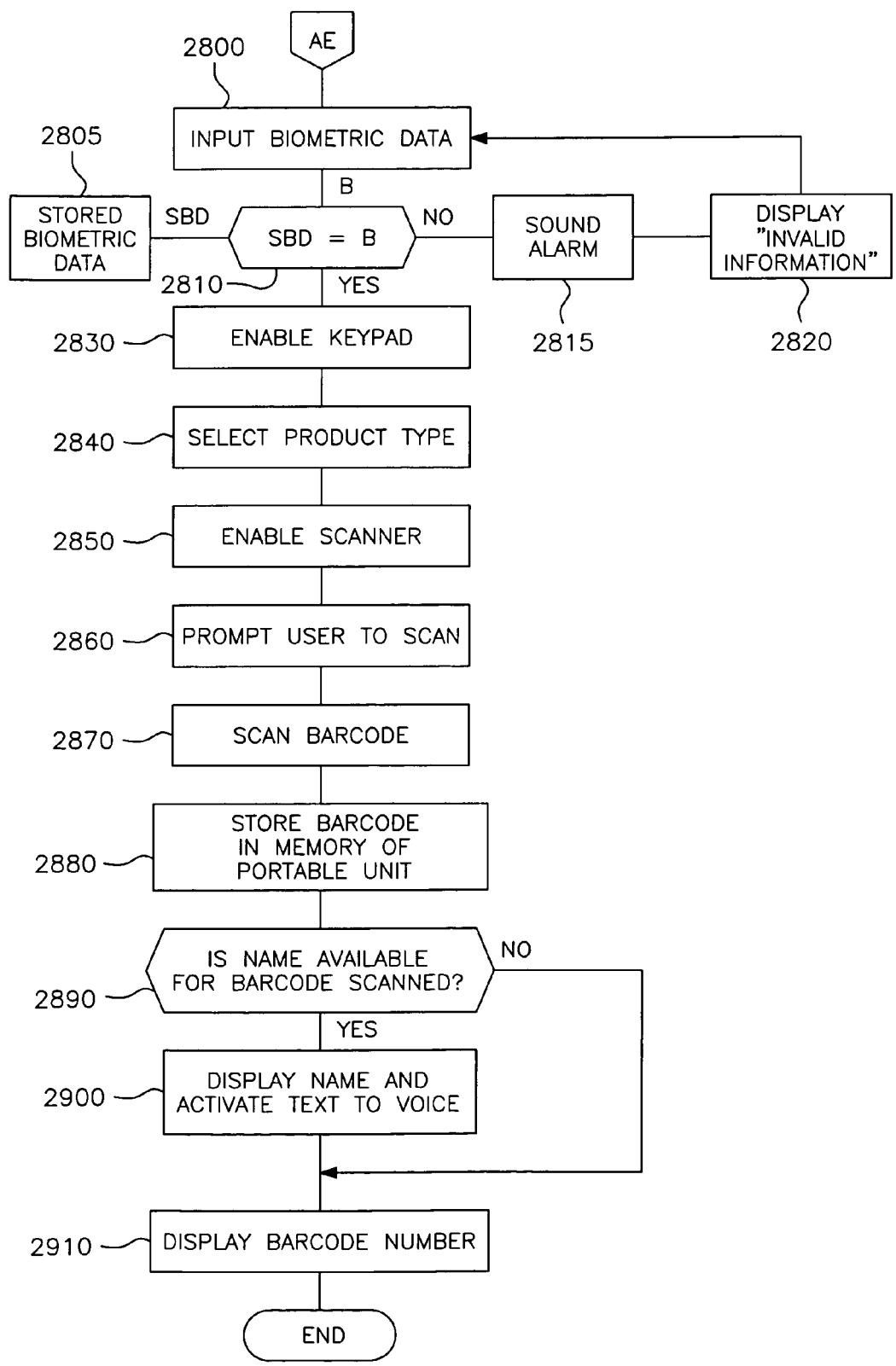
FIG. 16 is a flow chart illustrating steps that can be performed when data is acquired by the portable unit.
Figure 17B:
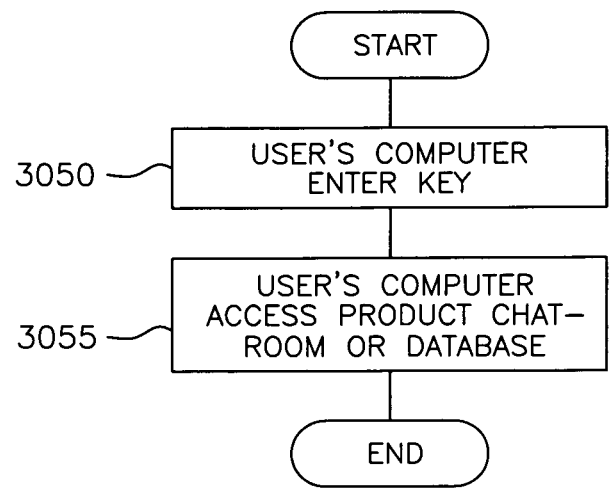
Figure 17C:
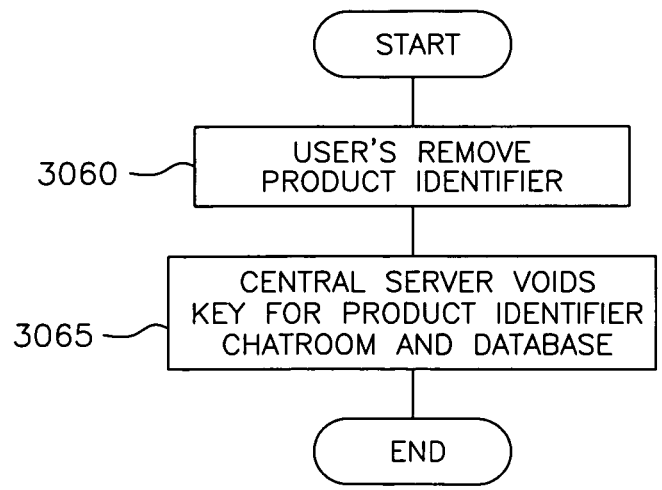

FIG. 16 depicts an exemplary function related to the use of biometric data and the visual or audio identification of products primarily for visual and hearing impaired users. In accordance therewith, entry of biometric data is the function selected (step 954 of FIG. 10). The first processing step, step 2800, is to input biometric data (for instance: iris scanning or finger print. At step 2810 the biometric data entered is then compared with the stored biometric data 2805. If there is a positive match between the entered biometric data and the stored biometric data, then step 2830 enables key pad. If there is no positive match, an alarm will sound (2815) and the display will inform the user that the biometric data is invalid, step 2820.

Once the biometric data is validated and the keypad enabled, step 2830, the user selects product type, step 2840. Step 2850 enables scanner and step 2860 prompts user to scan. Next, the user scans barcode, step 2870, and stores bar code in the memory of the portable unit 40, step 2880. Next, step 2890 determines if name is available for bar code scanned. If not, operation proceeds to step 2910 and the bar code number is displayed. If the name is available, the name of the product is presented using visual and audio means, step 2900, and the process continues with step 2900 to display bar code number, and the operation ends.

FIG. 17A shows an exemplary function related to the acquisition of a key or password by the user in order to access the database or chat room related to the product being used or illness indicated by the user's biological variables and/or injury/illness caused by a product, including chat rooms related to support groups for a certain type of illness/injury. The user can acquire a key for any condition or product of interest. In accordance, acquire key 956 (FIG. 10) is the function selected.

According to the function, in step 3000 the user transfers product identifier to central server 10 according to the principles of the invention. Then central server 10 generates a product key at step 3010. Step 3020 then transfers the key to the user and step 3030 stores the key in user's computer. At step 3040, if user is online then user's computer accesses product chat room or database, and the operation ends. Alternatively, the user can acquire the key and later access chat room. Accordingly, and now referring to FIG. 17B, at step 3050 user's computer enters the key and then accesses chat room or database at step 3055 and the operation ends.

When user deletes a product identifier (see, for example, step 4120 of FIG. 19B), then the central server 10 voids the key related to the product identifier. In accordance, and referring to FIG. 17C, anytime the user removes or deletes a product identifier, step 3060, the central server 10 voids that key for the product identifier, step 3065, and the operation ends. Alternatively, the GPI server 10 can automatically transmit a key to all of the users of the product. The key is necessary to enter a room, for example, an electronic room, board or window found on commercial on-line providers. Moreover, the users of the same recalled product who sustained harm caused by the product can communicate with each other, thus creating a support system for the victims and allowing the victims to share experiences, tips on treatment, how to personally control certain symptoms, and the like.

Figure 18A:
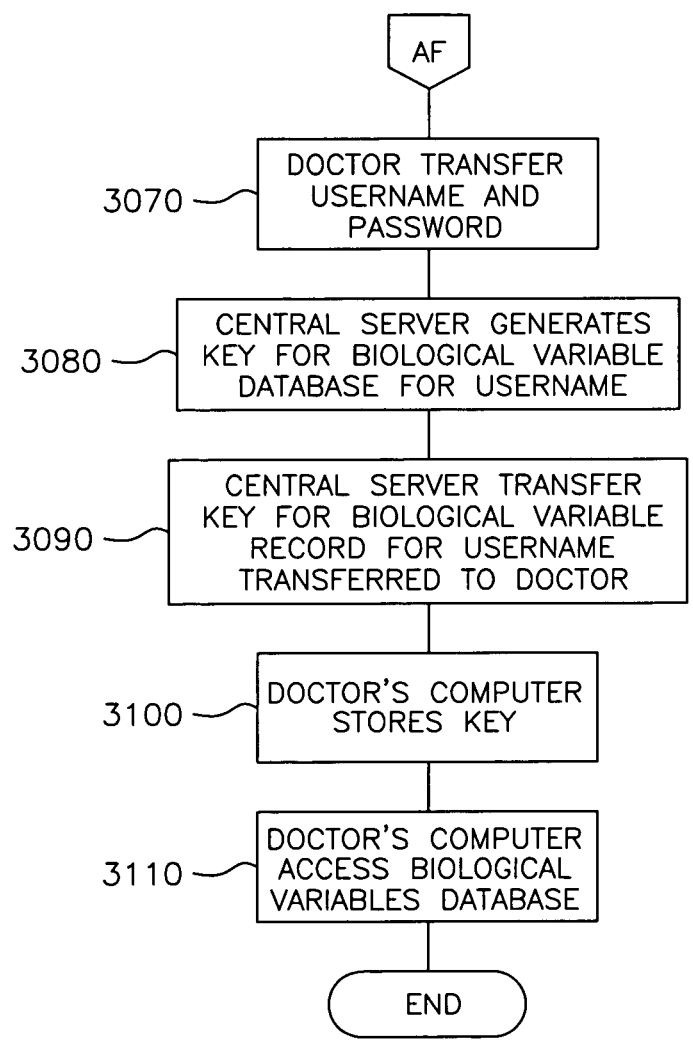
FIGS. 18A through 18C are flow charts illustrating exemplary steps that can be performed when acquiring, deleting or using biological variable data provided by the portable unit.
Figure 18B:
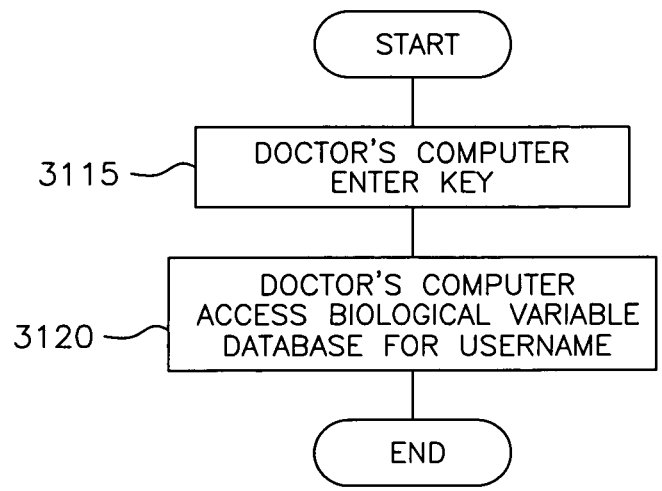

FIG. 18A shows an exemplary embodiment related to the acquisition of a key by a medical provider or authorized provider. The doctor, for example, can then access the biological variables transferred to a central database. In this embodiment the user, who may be a patient with glaucoma or diabetes, transfers his/her biological variables to a central database. The doctor then at his/her discretion can access the database and check the biological variables parameters and values for any of the doctor's patients. In accordance, operation starts and at step 3070 the doctor transfers the username and password. The password is needed so that only the doctor treating the patient or authorized provider can access the biological variable database for the patient. After proper authentication and identification according to conventional means is secured, at step 3080 the central server 10 generates the key for biological variables database for the username transferred. Next, at step 3090 central server 10 transfers key to doctor's computer for biological variable record for username. At step 3100 the doctor's computer stores the key and accesses biological variables record for the user in biological variables database, step 3110, and the operation ends.

Figure 18C:
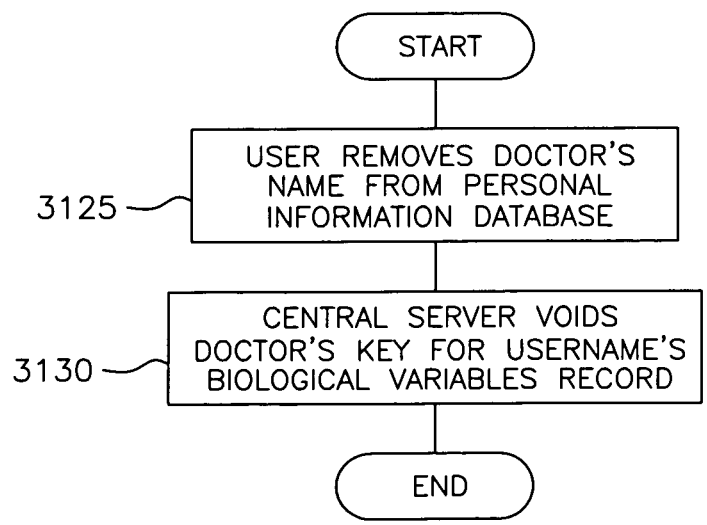

Although biological variables can be electronically transferred to a remote computer such as the doctor's computer, this can be considered as an alternative embodiment since it can flood the doctor's remote computer with vast amounts of data. According to the preferred embodiment, data remains stored in a central database that can be easily accessed by any person at any place in the world as long as the person is an authorized user. The doctor can also acquire the key and later access the patient's biological variable record or chat room. Accordingly, and referring to FIG. 18B, at step 3115 the doctor's computer enters the key and then accesses biological variables record or chat room, step 3120, and the operation ends. FIG. 18C shows a summary of processing related to voiding a key. When the doctor deletes username or preferably the user removes doctor's name 712 from personal information database at step 3125, then the central server 10 voids the doctor's key related to the username biological variable record, step 3130, and the operation ends. Alternatively, the GPI server 10 can transmit a key to the doctor who is responsible for the medical care of a certain user.

Figure 19B:
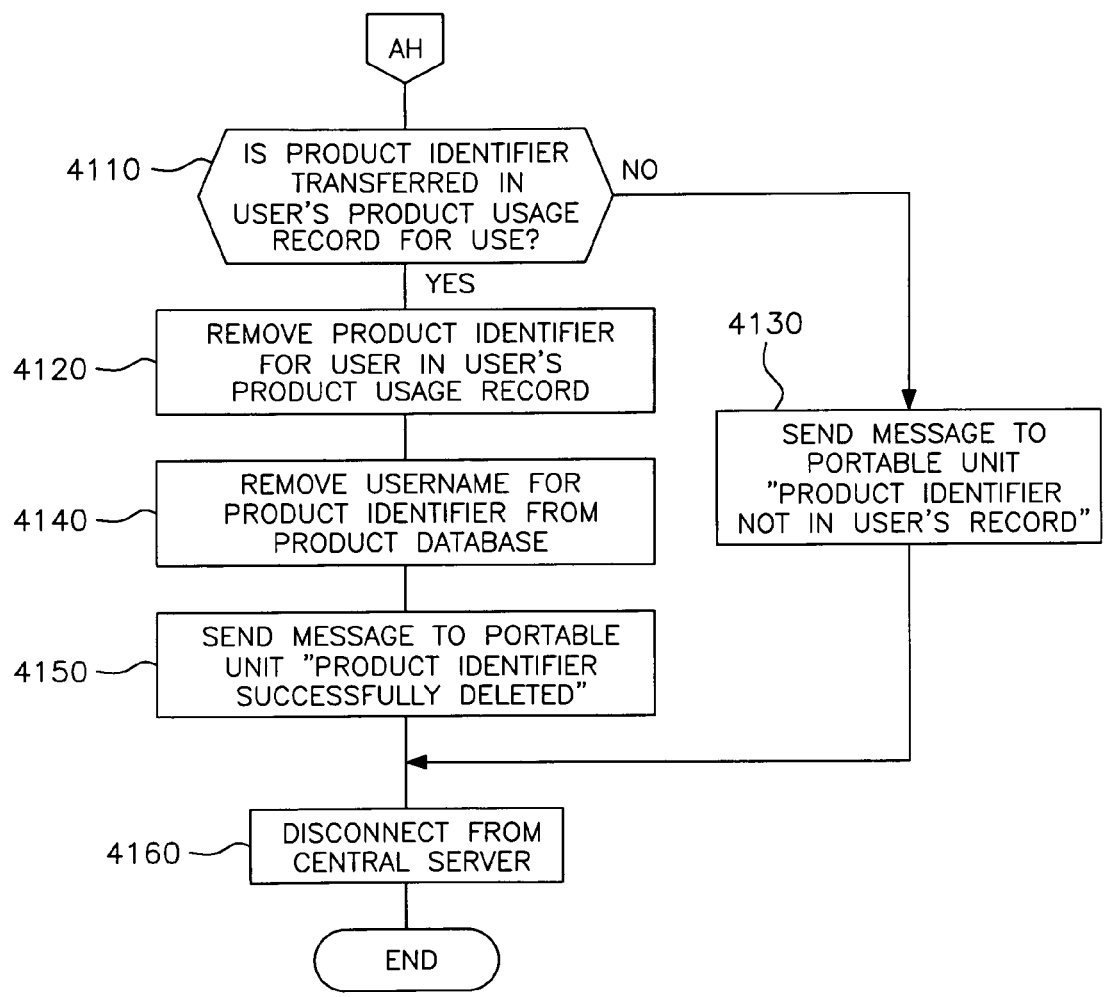

FIGS. 19A and 19B depicts an exemplary embodiment related to removal of product identifier from the database by the user. In accordance, when remove product identifier function is selected, step 960 of FIG. 10, the user can select a product type at step 4000. Upon selection of product, the scanner is enabled at step 4010 and prompts the user to scan the bar code at step 4020. The next step 4030 then determines if the product identifier is the last one to be scanned. If it is not the last product identifier, then the bar code for the product identifier is scanned at step 4040. The next operation, step 4050, determines if the bar code is valid. If it is valid, processing continues with step 4070 and the scanned unique bar code for the product is stored in the portable unit memory. If the bar code is not valid, the user is prompted to rescan, step 4060. Next, the user is prompted to scan another bar code related to a new product identifier and the process repeats until the last product identifier is scanned.

After the last product identifier is scanned, processing connects the portable unit 40 with the central server 10 at step 4080 and username and password are transferred at step 4090. Upon valid verification and authentication, the encrypted product identifier is transferred to the central server 10 at step 4100. Next, step 4110 determines if product identifier transferred is in user's product usage record for user in user's product usage database 740. If not, step 4130 sends a message to portable unit 40, "product identifier not in user's record" and then proceeds to step 4160. If the product identifier is in the user's record, step 4120 removes product identifier for user in user's product usage record. Next, step 4140 removes username for product identifier from product database. Then step 4150 sends message to portable unit 40 "product identifier successfully deleted". Step 4160 then disconnects from central server 10 and operation ends.

Figure 20A:
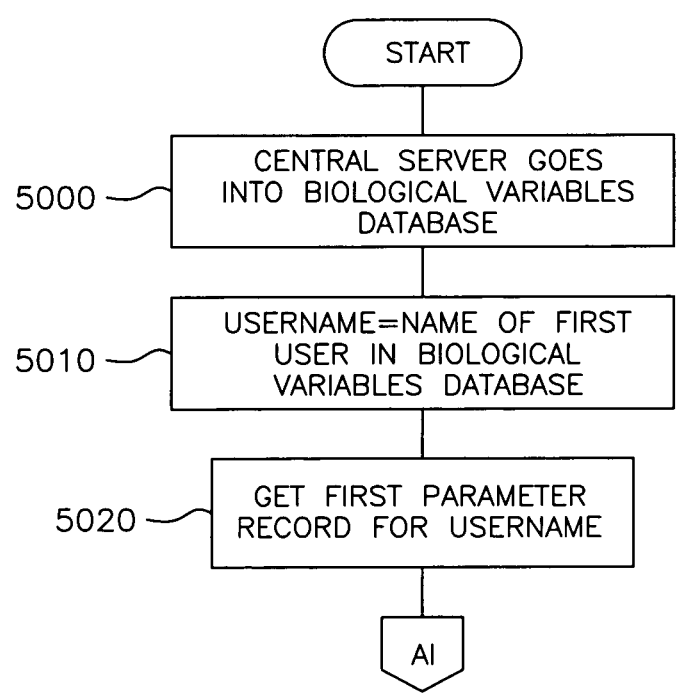
FIGS. 20A and 20B are flow charts illustrating an exemplary sequence of operating steps that can be performed when removing data via the central server according to the principles of the invention.
Figure 20B:
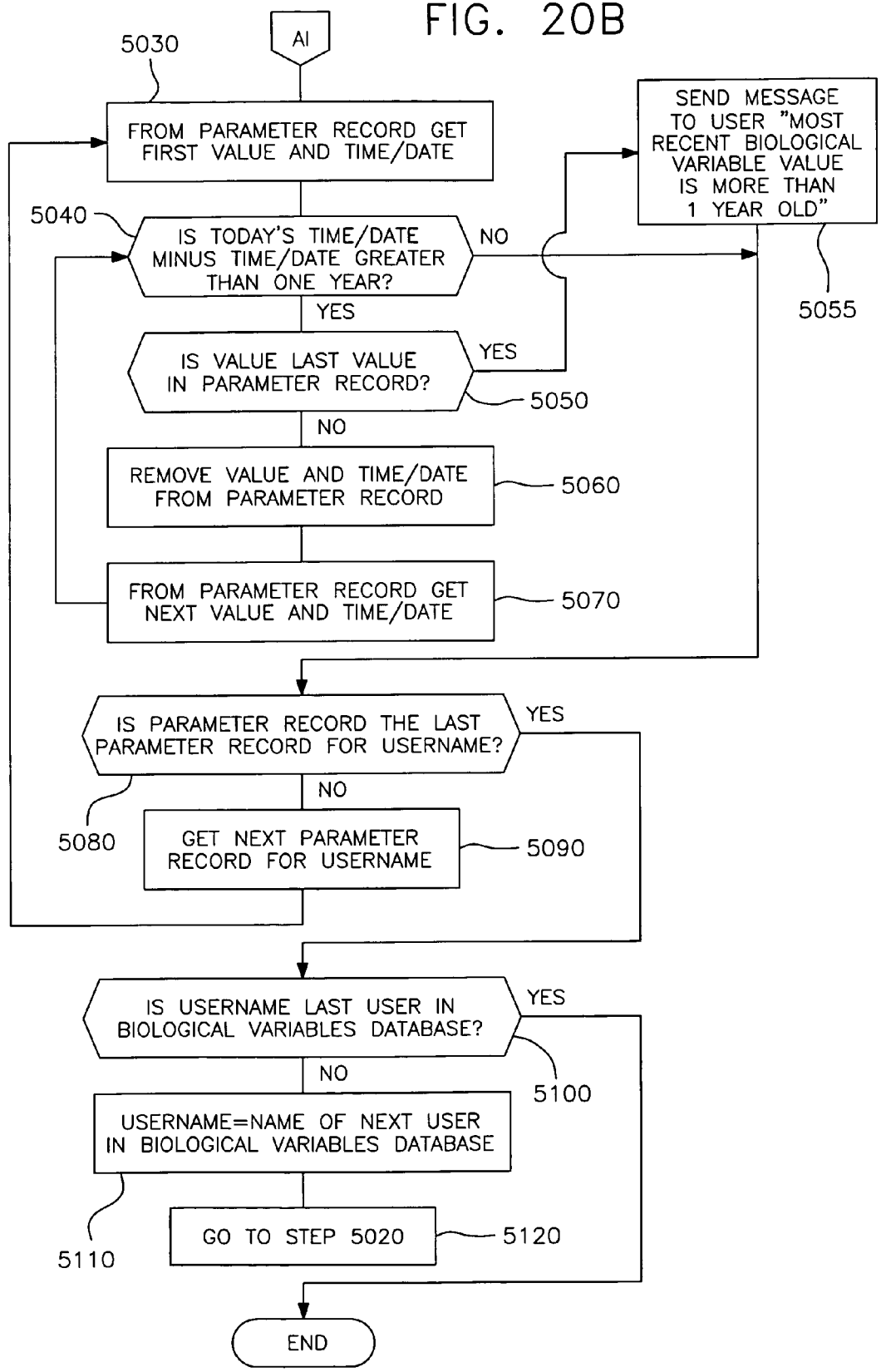

FIGS. 20A and 20B shows an exemplary embodiment related to automatically removal of biological variable values by the central server in order to avoid retention of a large amount of old data in the database. Biological variables relate to dynamic changes occurring in the human body, thus data that it is more than a year old may not be relevant to the user's present health status and thus will be automatically deleted. Biological variables acquired either at the doctor's office or at the user's domicile are automatically deleted if the data is more than a year old. However, the system will preserve at least one value since healthy individuals may go to their doctor only once every two or three years while older patients may go the doctor on a routine basis every three months. The system will preserve at least one value for each biological variable parameter transferred which can be used as a reference for the medical status of the user.

Accordingly operation starts and at step 5000 the central server 10 accesses the biological variables database 770. Then at step 5010 username equals the name of the first user in biological variables database. Next, step 5020 gets first parameter record 774 for username. Then, from parameter record 774, step 5030 gets first value 775 and time/date 776. Next step 5040 determines if today's time/date minus time/date is greater than one year. If not, operation proceeds to step 5080; otherwise, step 5050 determines if value is the last value in parameter record. If yes, step 5055 sends message to user that "most recent biological variable value is more than 1 year old" and proceeds to step 5080. If the value is not the last value, then step 5060 removes value and time/date from parameter record. Next, from parameter record, step 5070 gets next value and time/date and repeats processing, step 5040, to determine if today's time/date minus time/date is greater than 1 year. If not, processing proceeds to evaluate another biological variable parameter and step 5080 determines if parameter record is the last parameter record for the user. If the difference is greater than 1 year, the process proceeds to step 5050.

If the record is not the last parameter record, step 5090 gets next parameter record for username, and processing repeats until all values and parameters are evaluated for the username. If the record is the last, step 5100 determines if username is the last user in biological variables database. If yes, the operation ends; otherwise, at step 5110 username equals name of the next user in biological variables database, and at step 5120 go to step 5020 for further processing until biological variables for all users are evaluated.

The system can work on information locally stored, but if the information on the unique potentially harmful product transferred by the user is not located over the GPI server 10, the GPI server 10 can then connect the user to the remote site over the Internet 100 which contains the warning information on the harmful product. It is thus understood that alternative embodiments can be implemented with the information sent to the user concerning a warning or recall related to a product being used and/or interaction product-product and product-biological variable comprising also a web URL (Uniform Resource Locators), bulletin board address, direct connection with a web site, and the like as well as a voice mail address, phone number, mail address and the like, with all of these sources containing relevant information related to the product warning and/or recall and other interactions. Alternatively, the GPI server 10 can electronically connect the user of the product with the site on the Internet which contains the warning information, such as the research institution 154, or the manufacturer 148, or the FDA 130, or the CPSC 132, and the like. Information relevant only to the products associated with a unique user is transferred back to the user and the user receives selected information on only the products being utilized by the user and only on interaction product-biological variables corresponding to the health status of the single user. It is understood that advances in processing and communication mediums will allow the unique product identifiers and biological variables to be automatically, continuously, and instantaneously transferred to the GPI server 10 as the unique product identifiers and biological variables are acquired and/or selected by the user with the subsequent automated processing and transfer of alert information related to the product identifiers and biological variables back to the user related to the product identifiers and biological variables.

The user's personal information 700 can be expanded to include other information about said user. The user can include credit card information and other commonly used data linked to the user including a train schedule. For example, the user, Mr. Martin, is on a three month trip in Switzerland. The user checks his eye pressure, blood cholesterol and blood sugar using the aforementioned Abreu self-monitoring devices using a cell phone as the receiver for the signal from the monitoring devices. The data is sent to the GPI server 10 which identifies increased eye pressure and, considering that the user is using amiodarone, a harmful interaction causing eye damage is identified. The GPI server 10 also identifies a newly recalled product (Redux®) which is stored in the user's product usage database 740. A newly recalled chocolate found to have undisclosed amounts of peanuts is also identified. Since the user is allergic to peanuts an alert is generated. While the GPI server 10 had also identified a recalled crib as being used, the system notes that a successful phone alert was sent. The user has a doctor's name in Switzerland stored in his personal information database 700 and an appointment is scheduled. Since the user had his credit card information and train schedule stored in the user's personal database 700, the message delivered identifies which train to take to get to the doctor and includes a reserved ticket for the trip.

Although sequencing processing is primarily described, it is understood that other processing design known by one skilled in the art can be used. For instance, an object oriented design with parallel processing can be used. For example step 1710 to 1780 can be an alert object class applied to any product identifier or any biological variable.

Alternatively, hand-held IECLD 40 may also be used in an on-line manner using conventional communication lines such as telephone lines or electronic communications medium in which there is a link and transmission of data to and/or from the IECLD 40 to the GPI server 10 computer station. The IECLD 40 has data storage, processing and transmission capabilities and the on-line communication between the IECLD 40 and the central GPI server 10 can be done digitally using, for instance, an acoustic coupler. In this alternative embodiment, the coupling station is located at the doctor's office or at a pharmacy where the user receives or fills a prescription for the drug, or alternatively can be done by the patient at home. The patient enters a Personal Identification Number or password manually, which is then compared with a number stored in the IECLD 40 memory unit. If there is a match, the new drug can be scanned in using the bar code reader system and the data sent to the GPI server 10 using conventional communication lines. If at the time of entering, there is a warning about the drug stored in the IECLD 40, an alarm will sound and stored information will appear on the display. Although it is technically possible for the hand-held device to be updated with information from the GPI database at the time of the on-line coupling with GPI server 10 computer station, this is not the preferred way since the hand-held device would have to have very large memory capabilities to be able to store the data on the thousands of drugs and/or products stored in the GPI database. When, however, the IECLD 40 is used in this manner, any time a drug is entered, such as for instance scanning a bar code for that drug, the entered drug would automatically be evaluated against the data stored in the memory of the portable device. If the drug prescribed is found to have potentially detrimental effects, an alarm would be activated and the information on the drug displayed in the display and a flashing light activated allowing immediate recognition of the potential harmful effect before the drug was even used or even purchased. At any time of coupling the new data is transferred from the GPI server 10 station to the portable IECLD 40 and vice-versa.

FIG. 21 illustrates another exemplary embodiment in which the IECLD 40 can interface with standard telephone lines using binary data, with the binary data generated by the IECLD 40 being processed via standard encryption applications using conventional encryption algorithms available from the National Bureau of Standards. The encrypted binary data is then transmitted and demodulated and decrypted at the receiving unit with the unit being the GPI server 10 computer station, but preferably in this embodiment the receiving/transferring unit is another IECLD 40 device. The GPI system 1 thus allows secured communication not only between the GPI server 10 computer station, but also between one IECLD 40 and another suitable IECLD 40. The communication between two IECLD's 40 would be useful if a patient with one IECLD 200 wants to communicate and transmit the data on the drugs being used to a doctor who also has a IECLD 202, or to an insurance company which has a IECLD 204, or to a hospital which also has a IECLD 206, or to a pharmacy which has a IECLD 212, or to an ambulance which carries a suitable corresponding IECLD 208 and need to know precisely what drugs and devices a patient is using, or to another institution which may not have an IECLD 40 but has some device 210 able to access and decode the data being transmitted by the patient's IECLD 200, and the like. This allows the transmission of data in an accurate, time- and cost-efficient manner from one IECLD 200 to a receiving point in need of that data. For the transmission of data between two IECLD 40, the IECLD 40 #1 is used in a barter way and IECLD 40 #2 is programmed to accept data from another corresponding IECLD 40, such as IECLD 40 #1, and the data is then electronically transferred directly between the two IECLD 40s. The responding unit such as the ambulance which carries a IECLD #2 208, may then automatically and electronically receive the data from the patient's IECLD #1 200 including the biological variables measured at home by the patient such as blood pressure, eye pressure, blood glucose, temperature etc, as well as the information on the products used and drugs and medical devices used. The ambulance IECLD 208 can then send the information on the condition of the patient and treatment being administered back to the patient's IECLD 200 for storage, and also to a receiving unit at a hospital 206 and at the doctor's office 202 which then will have all of the information on previous drugs and devices previously being used by the patient as well as biological variables measured at home plus the new information on treatment that was administered on the way to the hospital in the ambulance. For a complete and reliable information system to be implemented, in this embodiment it is preferred that the patient carry with him some type of identification informing that he/she has a IECLD 200 and how to contact or access the patient's IECLD 200 because sometimes a patient will suffer a heart attack or other acute medical event and become unconscious, with paramedics and physicians not being able to learn what medications or devices are used by the patient. The knowledge of that information is sometimes the difference between life and death for that particular patient and the IECLD 200 will provide the life-saving information in a timely, inexpensive, and efficient manner.

When for instance, the communication between the IECLD 200 is established with the GPI server 10, the microprocessor is programmed to access the GPI database in the GPI server 10 after a conventional data stream is exchanged and connection established between the IECLD 200 and the GPI central server 10 computer station. The IECLD 200 then obtains any data on the drugs and products from the GPI server 10 computer related to the drugs and products which are then stored in the IECLD 200 memory unit for the user. The data is then displayed on the display of the IECLD 40 with updating of the data and new data being stored in the IECLD 200 memory unit. If the new input data relates to drug "D" for instance, which is given by the paramedics in the ambulance, the IECLD 200 will send data informing the GPI server 10 station that a particular patient Mr.XYZ was given the drug "D", and the IECLD 200 is programmed to obtain from the GPI server 10 any information available on drug "D" or any information on interactions of drug "D" with biological variables of patient Mr.XYZ. So if there is new data, the new data on drug "D" will be displayed in the display of the IECLD 200. If there is new data encoded with harmful interaction code, then a special alarm will sound to inform the user of the harmful condition caused by the harmful product being bought or prescribed or given. If a potentially harmful product is identified and coded as harmful, the user is informed and if there is a recall or potentially harmful effect, then the various points-of-sale carrying or selling the harmful product and doctors prescribing the harmful product, which can be identified by the GPI server 10, are contacted and an alert notice and information sent are to the numerous places and professionals.

In the aforementioned Abreu patent, there is described a system in which no numerical values are displayed in the display in relation to providing output related to measured biological variables. Abreu utilizes a system of lights which corresponds to the range of values for the biological variables. The portable unit IECLD 40 provides an improvement over Abreu's invention by providing an interactive display in which the user can receive information and information on how to proceed according to the level of the biological variable measured. For instance when measuring eye pressure if the pressure is within acceptable levels, the green light by Abreu would appear. In the present invention a message would appear stating that "You are fine" and "You should keep the appointment with Dr. Jones at 6 p.m. on January 1. Please bring your glasses and medications with you". Since there was a record entered by the doctor that the patient did not bring his glasses with him in the previous appointment, the IECLD 40 will remind the patient of that. A list of the medications with its schedule would subsequently appear on the screen indicating which should be the next medications to be taken and what is the dosage to be taken according to the prescription by the doctor. The patient could then interrogate the IECLD 40 in regards to the meaning of the level of the pressure measured and then receive information stored in the IECLD 40's memory in regards to what that level of pressure means for that particular patient according to the patient's specific health status. If the pressure measured was within borderline values, the yellow light by Abreu would appear. In the present invention, a message would appear stating "Your eye pressure is borderline and you should check your eye pressure again in three hours. If you experience any eye pain please press the contact office button on your screen." If the eye pressure measured is above acceptable levels, the red light by Abreu would appear. In the present invention, a message would appear stating "Your eye pressure is above acceptable limits. Please check your eye pressure again in 15 minutes. If you experience any eye pain or redness please press the contact office button on your screen." If the pressure measured is very high, which could potentially cause irreversible damage in a short period of time, the present invention would display a message stating "Please come immediately to the office for evaluation. Your pressure is well above acceptable safe limits." A warning message about the patient's condition would also be transmitted to the medical provider's office over the public network. Each IECLD 40 is calibrated according to the range of pressure which is considered safe for that particular patient and according to the overall health status of that patient. It is also understood that the above disclosed technology could be applied to any other home monitoring device such as blood sugar monitoring as described by Abreu, blood pressure measuring devices, heart monitors, pregnancy tests, and the like.

Another embodiment of the present invention relates to the transmission of biological data acquired using diagnostic or monitoring tests as described in the patents by Abreu or any diagnostic or monitoring device. The IECLD 40 interface with the various monitoring and diagnostic devices via a low power RF or IR interfaces. The IECLD 40 could be activated at prescribed intervals to store the biological data which was received from the other monitoring devices and to subsequently deliver the biological data over a public network such as the Internet and to a server 10 and then to a database. It is also understood that the IECLD 40 could be placed next to the monitoring device in order to receive the biological data at the time of measuring the biological data. The data could then be stored for later transmission or the data could be immediately transmitted over the public network to the corresponding database in the server 10.

The foregoing description of the preferred embodiments of the present invention have been provided for the purposes of illustration and description. Many modifications and variations will be apparent to those skilled in the art. The embodiments were chosen in order not to limit the scope of the invention but to best explain the principles of the invention and its practical applications.

I claim:

1. A computer-implemented method of transferring information between a user and a third party through a centralized computer having a prescription medications information database, said method comprising the steps of:
   receiving, at the centralized computer, product identification information identifying a product from a user;
   storing the product identification information in said product information database and establishing a link between said product and said user;
   receiving, at the centralized computer, the user's dynamically changing biological variables transmitted by the user from a remote location at different points in time, the biological variables being measured by health monitoring devices;
   receiving, at the centralized computer, product update information on said product from a third party;
   updating, by the centralized computer, said product information database with said product update information, wherein new information about the product is entered into the centralized computer;
   reviewing, by the centralized computer, the product information database to identify user-product links associated with said product;
   transmitting, on an automated basis, an electronic message containing said product update information of all users identified as having user-product links;
   storing, in response to a user purchase of said product, product identification information for said product under a username;
   receiving by the centralized computer, product update information on said product;
   analyzing, by the centralized computer, interaction of the product with the biological variables from the user for potential harm indicated by the measured values of the biological variables and interaction with the product;
   identifying, by said centralized computer, a point in time from the different points in time at which the dynamically changing biological variables cause a potentially harmful interaction with the product;
   reviewing, by said centralized computer, the database for product identification information correlating with said product update information;
   identifying the username as linked with the product; and
   transmitting a message to said username with said product update information and a contraindication of use of the product based upon the measured biological variables at the point in time from the different points in time.

2. The method as set forth in claim 1, further comprising, before the second step of receiving, the steps of:
   entering the product information into a remote terminal; and
   electronically transmitting the product information to the centralized computer.

3. The method as set forth in claim 1, wherein product information is entered by scanning a bar code.

4. The method as set forth in claim 1, wherein currently used products include prescribed prescriptions.

5. The method as set forth in claim 1, further comprising the steps of:
- reviewing by the centralized computer, the product information database for information relating to the product; and
- notifying the user of any information relating to the product.

6. The method as set forth in claim 1, further comprising the steps of:
- reviewing by the centralized computer, products taken by the user; and
- notifying the user of any danger or complications regarding the simultaneous use of the products.

* * * * *